US012781258B2

(12) United States Patent
Broadbent et al.

(10) Patent No.: US 12,781,258 B2
(45) Date of Patent: Nov. 3, 2026

(54) METHODS FOR NORMALIZATION AND QUANTIFICATION OF SEQUENCING DATA

(71) Applicant: BioFire Diagnostics, LLC, Salt Lake City, UT (US)

(72) Inventors: Kate Mariel Broadbent, Salt Lake City, UT (US); Robert John Crisp, Cottonwood Heights, UT (US); Ann Michelle Demogines, Salt Lake City, UT (US); Matthew Kam Jones, Sandy, UT (US); Margarita Rogatcheva, Sandy, UT (US); Usha K. Spaulding, Millcreek, UT (US)

(73) Assignee: BioFire Diagnostics, LLC, Salt Lake City, UT (US)

( * ) Notice: Subject to any disclaimer, the term of this patent is extended or adjusted under 35 U.S.C. 154(b) by 447 days.

(21) Appl. No.: 17/048,771

(22) PCT Filed: Apr. 18, 2019

(86) PCT No.: PCT/US2019/028096
§ 371 (c)(1),
(2) Date: Oct. 19, 2020

(87) PCT Pub. No.: WO2019/204588
PCT Pub. Date: Oct. 24, 2019

(65) Prior Publication Data

US 2021/0180112 A1 Jun. 17, 2021

Related U.S. Application Data

(60) Provisional application No. 62/660,460, filed on Apr. 20, 2018.

(51) Int. Cl.
*C12Q 1/689* (2018.01)
*C12Q 1/6806* (2018.01)
*G16B 30/00* (2019.01)

(52) U.S. Cl.
CPC ........... *C12Q 1/6806* (2013.01); *C12Q 1/689* (2013.01); *G16B 30/00* (2019.02); *C12Q 2525/161* (2013.01); *C12Q 2525/191* (2013.01); *C12Q 2535/122* (2013.01); *C12Q 2537/165* (2013.01); *C12Q 2545/114* (2013.01); *C12Q 2563/179* (2013.01); *C12Q 2565/514* (2013.01)

(58) Field of Classification Search
None
See application file for complete search history.

(56) References Cited

U.S. PATENT DOCUMENTS

| | | | |
|---|---|---|---|
| 6,303,305 | B1 | 10/2001 | Wittwer et al. |
| 6,645,758 | B1 | 11/2003 | Schnipelsky et al. |
| 6,780,617 | B2 | 8/2004 | Chen |
| 7,387,887 | B2 | 6/2008 | Wittwer et al. |
| 8,394,608 | B2 | 3/2013 | Ririe et al. |
| 8,895,295 | B2 | 11/2014 | Ririe et al. |
| 9,586,208 | B2 | 3/2017 | Ririe |
| 2009/0136951 | A1 | 5/2009 | Hart et al. |
| 2014/0283945 | A1 | 9/2014 | Jones et al. |
| 2014/0315725 | A1 | 10/2014 | Faham et al. |
| 2015/0118715 | A1 | 4/2015 | Wittwer et al. |
| 2015/0292001 | A1 | 10/2015 | Willey et al. |

FOREIGN PATENT DOCUMENTS

| | | | |
|---|---|---|---|
| CN | 104736722 | A | 6/2015 |
| WO | 2014039556 | A1 | 3/2014 |
| WO | 2014082032 | A1 | 5/2014 |
| WO | 2016094947 | A1 | 6/2016 |

OTHER PUBLICATIONS

Zook et al. (2012) Synthetic Spike-in Standards Improve Run-Specific Systematic Error Analysis for DNA and RNA Sequencing. PLoS ONE 7(7): e41356. doi: 10.1371/journal.pone.0041356.*
Chen et al. 2016. The overlooked fact: fundamental need for spike-in control for virtually all genome-wide analyses. Mol Cell Biol 36 :662-667. doi:10.1128/MCB.00970-14.*
Hindson et al. "High-Throughput Droplet Digital PCR System for Absolute Quantitation of DNA Copy Number" Analytical Chemistry, 83(22):8604-8610 (2011).
Locati et al. "Improving small RNA-seq by using a synthetic spike-in set for size-range quality control together with a set for data normalization" Nucleic Acids Research, 43(14):e89 (2015).
Chen et al. "The Overlooked Fact: Fundamental Need for Spike-In Control for Virtually All Genome-Wide Analyses" Molecular and Cellular Biology 36(5):662-667 (Mar. 1, 2016).
Chinese Office Action corresponding to Chinese Application No. 201980041439.X (Foreign Text, 8 Pages, English Translation Thereof, 17 Pages) (Mar. 7, 2024).
Dawei et al. "Introduction of Linearity Evaluation of Quantitative in vitro Diagnostic Products and Its Application on the Registration Testing of Quantitative Diagnostic Kit for Tumor Markers" China Pharmaceutical Affairs, No. 9 (Sep. 20, 2013).
Zook et al. "Synthetic Spike-in Standards Improve Run-Specific Systematic Error Analysis for DNA and RNA Sequencing" PLoS ONE 7(7): e41356 (Jul. 2012).
Nygren et al. "Quantification of HIV-1 Using Multiple Quantitative Polymerase Chain Reaction Standards and Bioluminometric Detection" Analytical Biochemistry, 288:28-38 (2001).

* cited by examiner

*Primary Examiner* — Joseph Woitach

(57) ABSTRACT

Methods and kits for normalization and quantification of sequencing data.

27 Claims, 15 Drawing Sheets

SAMPLE LYSIS

RECOVERY OF NUCLEIC ACIDS FROM LYSATE AND
OPTIONAL NUCLEIC ACID PURIFICATION

MULTIPLEX PCR1 USING TARGET-SPECIFIC PRIMERS WITH OVERHANGS

NUCLEIC ACID PURIFICATION

LIMITED CYCLE PCR2 USING SAMPLE-SPECIFIC SEQUENCING ADAPTER PRIMERS

NUCLEIC ACID PURIFICATION

LIBRARY POOLING AND SEQUENCING

METHODS FOR NORMALIZATION AND QUANTIFICATION OF SEQUENCING DATA

CROSS REFERENCE TO RELATED APPLICATIONS

This application claims the benefit of and priority to U.S. Prov. Pat. App. No. 62/660,460 filed Apr. 20, 2018, the entirety of which is incorporated herein by reference.

BACKGROUND

The ability to read the sequence of bases that comprise a polynucleotide has had an impact on biological research that is difficult to overstate. For the majority of the past 40 years, dideoxy DNA 'Sanger' sequencing has been used as the standard sequencing technology in many laboratories, and its acme was the completion of the human genome sequence. However, because Sanger sequencing is performed on single amplicons, the throughput of Sanger sequencing is limited, and large-scale Sanger sequencing projects are expensive and laborious.

The paradigm of DNA sequencing changed with the advent of 'Next-Generation' Sequencing (NGS) technologies, which process hundreds of thousands to millions of DNA fragments in parallel, resulting in a low cost per base of generated sequence and a throughput on the gigabase (Gb) to terabase (Tb) scale in a single sequencing run. It is remarkable to reflect on the fact that the first human genome, famously co-published in Science and Nature in 2001, required 15 years to sequence and cost nearly three billion dollars. In contrast, a modern NGS sequencer can sequence over 45 human genomes in a single day for approximately $1000 each. As a consequence, NGS can now be used to define the characteristics of entire genomes and delineate differences between them, allowing researchers to gain a deeper understanding of the full spectrum of genetic variation and to define its role in phenotypic variation and the pathogenesis of complex traits.

Nevertheless, the application of NGS to clinical and diagnostic applications may be limited by high intra-lab and inter-lab variation. These problems reduce the value of any results and have prevented the use of these sequencing methods in molecular diagnostics. For instance, the complexity and variability of NGS library preparation and sequencing reaction preparation can lead to sample-to-sample and lab-to-lab variations, which can make it difficult to determine the prevalence, for example, of genetic variations or pathogenic organisms detected in a sample.

In another instance, many of the pathogens targeted in diagnostic assays (e.g., FilmArray panels, BioFire, SLC, UT) can be found in the environment and as commensals at the site of sample collection. For example, in diseases such as pneumonia, the most frequently encountered bacterial pathogens may also exist as "normal flora" of the oropharyngeal passage which is often itself the site of sample collection (sputum and tracheal aspirates or nasopharyngeal swab (NPS)) or the route for collection of more invasive specimens such as bronchoalveolar lavage (BAL). Frequent contamination by or co-collection of normal flora is essentially unavoidable in such cases. In such a scenario the diagnostic power of NGS may be limited by the fact that clinically relevant organisms cannot be readily distinguished from commensals or contamination due to the likelihood that NGS can detect the presence of both highly and minimally concentrated organisms (i.e., NGS has an almost limitless dynamic range) without providing a great deal of inherent context to interpret the clinical relevance of detections in the sequencing data (e.g., NGS may detect the presence of a pathogen (i.e., nucleic acids from a pathogen) and its relative abundance (%) to other detected nucleic acids or organisms without providing any indication of whether or not the detected pathogen is present at a clinically relevant concentration).

The traditional practice in microbiological laboratories has been to perform semi-quantitative or quantitative cultures to distinguish pathogenic loads of bacteria from non-clinically relevant commensal carriage. Different diagnostic titer guidelines exist for different types of specimens. Similar approaches have been applied to NGS assays. By its nature, NGS provides semi-quantitative data and that, in the absence of confounding factors such as sample preparation errors or differences in sequencing efficiency, the number of sequencing reads for a target may be related to the abundance of the target. Several groups have taken advantage of this relationship to obtain relative quantification data for unknown nucleic acids in NGS. For example, the relative abundance of nucleic acids in a sample can be determined by performing a series of serial dilutions (illustratively, 10-fold dilutions) of one or more samples, sequencing the series of diluted samples, and then plotting the numbers of reads found in each. These groups have assumed that if the relationship between the number of reads in the serial diluted samples has a linear relationship (e.g., a 10-fold dilution results in an approx. 10-fold reduction in the number of sequencing reads, an approx. 100-fold dilution results in a 100-fold reduction in the number of sequencing reads, etc.), then the number of sequencing reads can be used to relatively quantify different targets present in the sample (e.g., relatively quantify high and low concentration targets). For instance, if a first sequenced nucleic acid has 10 sequencing reads and a second has 100 sequencing reads, it may be concluded in this scenario that the second nucleic acid is 10× more concentrated than the first. This may be used, for example, to detect gene duplication and/or to determine the number of copies of a gene in a genome. Nonetheless, this approach is merely relative and, as a result, it is not possible to determine the concentration of the first or the second nucleic acid because there is no nucleic acid of known absolute concentration that can be used as a reference. As a result, this approach may not be very accurate. For example, in the case of a large difference (e.g., several orders of magnitude) between high and low concentration detections, resolution may be lost at lower and/or high concentrations, resulting in lowering the fold differences between high and low compared to the true difference. This approach is also not very specific due to the fact that it is only relative, it is sample/sequencing run specific, and it does not account for intra-lab and inter-lab variations.

Another common approach to quantification is to quantify the nucleic acids in a sample used for NGS in a separate reaction. For instance, quantitative PCR (qPCR) can function for absolute quantification, frequently using a standard curve approach. In this approach, a standard curve generated from plotting the crossing point (Cp) values obtained from real-time PCR against known quantities of a single reference template provides a regression line that can be used to extrapolate the quantities of the same target gene in samples of interest. Serial dilutions (illustratively, 10-fold dilutions) of the reference template are set up alongside samples containing the specific gene target that needs to be quantified. Various separate reactions are run, usually one for each level of the reference target and one each for the samples of interest. Also, since assay-specific differences in PCR efficiencies often affect quantification, separate standard curves, with separate reference templates, may be set up for different gene targets.

However, the power of NGS lies in its massive parallelism—i.e., 10s to 100s to 1000s of samples can be processed simultaneously and in parallel. Using qPCR to quantify targets in this scenario can be challenging. Although quantification of targets from 100s to 1000s of separate nucleic acid reactions has been performed using qPCR (see, e.g., High-Throughput Droplet Digital PCR System for Absolute Quantitation of DNA Copy Number, Hindson et al., Anal Chem. 2011 Nov. 15; 83(22): 8604-8610), this approach is technically challenging and requires special equipment. Also, qPCR approaches generally assume or require the assays to have the same PCR efficiency in singleplex and multiplex reactions, which may not be the case. In addition, all standard curve-based quantification approaches published to date require setting up external reactions and the calculation of standard curves.

Another approach is to quantifying the nucleic acids in NGS uses assay-specific competitive templates (see, e.g., US 2015/0292001). Such methods aim to provide reproducibility in measurement of nucleic acid copy number in samples by relying on a proportional relationship of a native target sequence to a respective competitive internal amplification control specifically designed for that native target sequence. The competitive template described in US 2015/0292001 uses identical priming sites to a native nucleic acid template of interest but a designed (e.g., artificial) inter-primer sequence so as to mimic the kinetics of the native target in the PCR reaction, and thus control for target-specific variation in PCR efficiency. However, as a result such an approach is specific to the assay and template of interest (i.e., the competitive template is target and sample specific). In order to employ the methods described in US 2015/0292001 a new competitive internal amplification control needs to be designed for each new assay and/or template to be sequenced, which limits the general applicability of this approach. In addition, the target generally needs to be sequenced with and without the competitive template in order to deconvolute the sequencing response of the target alone from the sequencing response of the target plus the competitive template. This adds to the level of complexity of the approach and has the potential to introduce error into the calculation.

Thus, there exists a need in the art for a universal internal quantification standard and associated quantification methods for NGS. Since nucleic acid purification from a patient sample is integrated into the NGS workflow, the effect of sample-driven variability in nucleic acid extraction, as well as the effect of any sample-derived inhibitors on PCR, and thus quantification, cannot be estimated easily by an external standard curve.

BRIEF SUMMARY

This disclosure provides methods, systems, and kits for a universal internal standard that can provide simultaneous quantification of multiple target species that also takes into account the effects of assay-specific and matrix-derived variances in sequencing outcomes. Because the standard is a universal standard it is not specific to the target, sample, or assay, and, as such, the standard, methods, and kits described herein can be used in any sequencing assay (e.g., an NGS assay). This disclosure also teaches use of process controls and/or limit of detection (LOD) control(s) for assay-specific correction.

In one aspect of the present disclosure, a method for read value normalization of a sequencing assay is disclosed. The method includes providing a sample including one or more unknown nucleic acids to be sequenced; adding to the sample a known quantity of an internal quantification standard (IQS); preparing the sample including the internal quantification standard for sequencing; sequencing to generate a sequencing data set for the sample, wherein the sequencing data set includes sequencing reads observed from the unknown nucleic acid(s) and from the internal quantification standard; counting the number of sequencing reads in the sequencing data set originating from the unknown nucleic acid(s) and the internal quantification standard; and normalizing the sequencing data set, wherein the normalization (1) applies data acceptance/rejection criteria to the sequencing data set based on the presence of a minimum number of sequencing reads for the internal quantification standard for the sample (e.g., a normalized number of sequencing reads are retained) and (2) ensures that substantially the same limit of detection (LOD) is applied to all unknown nucleic acids in the sequencing assay. In one embodiment, preparing the sample including the internal quantification standard for sequencing may include introducing sequencing primer binding sites and sample-specific identification sequences into the unknown nucleic acids and the internal quantification standard in the sample. In another embodiment, preparing the sample including the internal quantification standard for sequencing may include one or more of lysis of cells in the sample, recovery of nucleic acids from the lysate, nucleic acid purification, a first multiplex PCR using target-specific primers with overhangs, a second nucleic acid purification, a second multiplex PCR using sample-specific sequencing adapter primers, a third nucleic acid purification, and pooling of multiple similarly prepared samples for sequencing. Because the standard is added at the beginning of sample preparation, the standard is carried through all steps and systematic loss and efficiency are accounted for at all steps.

In one embodiment, each unknown nucleic acid in the sample may have a concentration of about $0\text{-}10^{13}$ copies/ml—i.e., in some instances the unknown nucleic acid may not be present (there are 0 copies/ml) or the concentration of the unknown may be very high (e.g., up to $10^{13}$ copies/ml). In a typical sample, the concentration of the unknown nucleic acid may range from about $10^3\text{-}10^9$ copies/ml. In one embodiment, the known quantity of the IQS added to the sample is in the range of about $10^4\text{-}10^6$ copies/ml (e.g., about $5\times10^5$ copies/ml). More or less IQS may be added to the sample depending on the limit of detection (LOD), or in order to affect the (LOD). In one embodiment, one type of IQS may be added to the sample. In another embodiment, two or more types of IQS may be added to the sample at different input concentrations so that a standard curve may be generated for quantification with two or more reference points.

In one embodiment, a linear relationship may preferably exist between the quantity of the internal quantification standard added to the sample and the number of sequencing reads for the internal quantification standard. That is, the number of sequencing reads attributed to the internal quantification standard may not be equal to the input quantity of the internal quantification standard, but the number of reads should be linearly related to the input quantity. If the relationship is not linear, this may be interpreted as an indication of a problem in one or more of the adding the internal quantification standard, the sample preparation, or the sequencing.

In one embodiment, the normalization retains a normalized number of sequencing reads (NORM), where NORM=No. of Sequencing Reads*(F/Observed No. of Sequencing Reads Originating from the Internal Quantification Standard). 'F' is a fixed, user-set normalization coefficient that defines a minimum expected number of IQS sequencing reads. In one embodiment, the value of F may be assay specific. 'F' is a sequencing read number value set to ensure a sequencing read depth sufficient for the limit of detection (LOD) of the sequencing assay. NORM may represent a subset of the sequencing data and is the number is sequencing reads that are saved for further analysis and quantification. For example, if 'F' and the Observed No. of Sequencing Reads Originating from the Internal Quantification Standard are the same, then NORM equals the number of sequencing reads recorded. On the other hand, if the number of internal quantification standard sequencing reads in the data set is greater than 'F', then NORM downscales the data to account for the over read and to ensure that the same LOD is applied across all samples. If the number of internal quantification standard sequencing reads in the data set is less than 'F', then the data from that sample may be rejected. In one embodiment, the data may be normalized with the relationship ALPHA, wherein unknown nucleic acid reads and internal quantification standard reads are each separately normalized by the same ratio ALPHA, where ALPHA=F/Observed No. of Sequencing Reads Originating from the Internal Quantification Standard.

In one embodiment, the sequencing read depth is in a range of about 1000 internal quantification standard sequencing reads to about 100,000 internal quantification standard sequencing reads, preferably about 2000 internal quantification standard sequencing reads to about 75,000 internal quantification standard sequencing reads, more preferably about 5000 internal quantification standard sequencing reads to about 50,000 internal quantification standard sequencing reads, or most preferably at least 5000 internal quantification standard sequencing reads. If less than 'F' sequencing reads are recorded to the internal quantification standard, the data for the sample associated with the insufficient 'F' read number may be rejected.

In one embodiment, the method may include calculating an input quantity (IQT) of the unknown nucleic acid in the sample after normalization, wherein because the input quantity of the internal quantification standard is known, the input quantity (IQT) of the unknown nucleic acid can be calculated by IQT=Normalized No. of unknown nucleic acid sequencing reads attributed to the unknown nucleic acid*(Input Quantity of internal quantification standard/F). In one embodiment, the method may include calculating the input quantity of two or more unknown nucleic acids in the sample by calculating an input quantity (IQTi, IQTj, IQTk . . . IQTn) of multiple unknown nucleic acids, if present, in the sample after normalization as IQTn=Normalized No. of unknown "n" nucleic acid sequencing reads attributed to the "nth" unknown nucleic acid*(Input Quantity of internal quantification standard/F).

In one embodiment, two or more samples may be pooled prior to subjecting them to sequencing. In one embodiment, samples may be pooled after the individual samples are prepared for sequencing and before the actual sequencing. In one embodiment, 2-1000 samples may be pooled after the preparing and before the sequencing, preferably 2-500 samples may be pooled after the preparing and before the sequencing, more preferably 2-100 samples may be pooled after the preparing and before the sequencing, more preferably 2-50 samples may be pooled after the preparing and before the sequencing, or most preferably 2-32 samples may be pooled after the preparing and before the sequencing. The number of samples that can be pooled for sequencing is generally limited only by the ability to differentiate between the samples in the resultant data. For example, samples in a pool may be differentiated by sample-specific sequencing adapter primers that are used to identify sequencing data originating from a specific sample. In this example, differentiation may be limited by the length and diversity of the sequencing adapter primers.

In one embodiment, each pooled sample has associated therewith a unique set of sample-specific identification sequences such that the sequencing data from each sample in the pool can be distinguished and separated. In one embodiment, each pooled sample has its own internal quantification standard associated with its own unique set of sample-specific identification sequences, and wherein the normalization is separately applied to each sample in the pool. In one embodiment, the normalization separately (1) applies data acceptance/rejection criteria to each sample in the pool and (2) ensures that substantially the same limit of detection (LOD) is applied to all unknown nucleic acids in each sample.

In one embodiment, the method may include calculating an input quantity (IQT) of the unknown nucleic acids in each sample after the data attributed to each sample has been normalized. Because the input quantity of the internal quantification standard in each sample is known, the input quantity (IQT) of the unknown nucleic acids can be calculated. An input quantity (IQTi, IQTj, IQTk . . . IQTn) of multiple unknown nucleic acids in the pooled samples can be calculated after normalization as IQTn=Normalized No. of unknown "n" nucleic acid sequencing reads attributed to the "nth" unknown nucleic acid*(Input Quantity of internal quantification standard/F).

In one embodiment, preparing the sample(s) for sequencing may include sample lysis to generate a lysate, recovery of nucleic acids from the lysate and optionally purifying the recovered nucleic acids, and introducing primer binding sites and sample-specific identification sequences into regions of the nucleic acids to be sequenced. The attaching may include one of: amplifying the nucleic acids to be sequenced in an amplification reaction using target-specific primers having dual-indexed sequencing overhangs that include sequencing primer binding sites and sample-specific identification sequences, or fragmenting the nucleic acids to be sequenced and ligating to the fragmented nucleic acids sequencing-specific adapters that include sequencing primer binding sites and sample-specific identification sequences.

In one embodiment, amplifying the nucleic acids to be sequenced may include: performing a first multiplex PCR reaction using target-specific primers having custom overhangs, performing a first nucleic acid purification, performing a second PCR reaction using dual-indexed sequencing adapter primers that anneal or ligate to the custom overhangs introduced in the first PCR, and performing a second nucleic acid purification. In one embodiment, the dual-indexed sequencing adapter primers are target-independent and include sequencing primer binding sites and sample-specific identification sequences.

In one embodiment, the amplification may be performed to limit or compress the upper end of the dynamic range of the concentration of the nucleic acids in the sample to be sequenced. This may reduce the sequencing and data analysis burden and reduce the number of instances where only the very highly concentrated nucleic acids appear in the sequencing data set. In one embodiment, the amplifying may include limiting one or more of concentration of the target-specific primers or cycle number in the first multiplex PCR reaction to plateau amplification of nucleic acids present at concentration greater than a desired dynamic range, as an example the compression may be performed to compress the dynamic range of nucleic acids to a plateau concentration of about $10^7$ copies/ml while nucleic acids present at less than $10^7$ copies/ml are present at a range of concentrations in the exponential amplification phase. In other embodiments, amplification may be performed to limit or compress other portions of the dynamic range. If, for example, only high concentration species are of interest in a sequencing assay, amplification may be limited so that only higher concentration nucleic acids (e.g., $>10^5$ copies/ml) are observed.

In any of the foregoing method embodiments, the sequencing assay may be a next-generation sequencing assay.

In another aspect, a method for performing a quantitative Next-Generation Sequencing (NGS) assay is disclosed. The method includes providing a sample including one or more unknown nucleic acids to be sequenced, wherein the unknown nucleic acids have a concentration of about $0\text{-}10^{13}$ copies/ml; adding to the sample a known quantity of an IQS, wherein the known quantity of the IQS is in the range of about $10^4\text{-}10^6$ copies/ml (depending on the targeted dynamic range of the assay); preparing the sample including the internal quantification standard for sequencing; sequencing the unknown nucleic acids and the internal quantification standard in the sample to generate a sequencing data; counting the number of sequencing reads in the sequencing data set originating from the unknown nucleic acid(s) and the internal quantification standard; and normalizing the sequencing data set and calculating an input quantity (IQT) of the unknown nucleic acid in the by IQT=Normalized No. of unknown nucleic acid sequencing reads originating from the unknown nucleic acid*(Input Quantity of internal quantification standard/F), wherein 'F' is a fixed minimum expected number of the internal quantification standard sequencing reads.

In one embodiment, the normalizing may include retaining a normalized number of sequencing reads (NORM) where NORM=No. of Sequencing Reads*(F/Observed No. of Sequencing Reads Originating from the Internal Quantification Standard). The normalization separately (1) applies data acceptance/rejection criteria to each sample in the assay and (2) ensures that substantially the same limit of detection (LOD) is applied to all unknown nucleic acids in each sample.

In one embodiment, the unknown nucleic acids may have a concentration of about $10^1\text{-}10^{12}$ copies/ml or, preferably, about $10^1\text{-}10^9$ copies/ml. In one embodiment, 'F' is related to the LOD of the assay. For instance, if 'F' is about $10^2\text{-}10^3$ for an input concentration of IQS of about $10^5$ copies/ml, then an LOD for the unknown nucleic acid in the sample is about $10^3\text{-}10^2$ copies per ml. If 'F' is about $10^3\text{-}10^4$ for the same input concentration of IQS (i.e., the read depth is increased and the weight of each read is increased correspondingly), then an LOD for an unknown nucleic acid in the sample is about $10^2\text{-}10^1$ copies/ml. For a given input concentration of IQS, the LOD can be raised or lowered by increasing or decreasing the read depth (i.e., by increasing or decreasing the degree of 'F') and, correspondingly, increasing or decreasing the weight attributed to each individual sequencing read.

In one embodiment, the method for performing a quantitative Next-Generation Sequencing (NGS) assay may include calculating an input quantity (IQTi, IQTj, IQTk . . . IQTn) of multiple unknown nucleic acids, if present, in the sample as IQTn=Normalized No. of unknown "n" nucleic acid sequencing reads attributed to the "nth" unknown nucleic acid*(Input Quantity of internal quantification standard/F).

In one embodiment, the method for performing a quantitative Next-Generation Sequencing (NGS) assay may include pooling two or more samples and subjecting them to sequencing simultaneously, wherein the two or more samples are pooled after the preparing and before the sequencing. In one embodiment, each pooled sample may have associated therewith a unique set of sample-specific identification sequences such that the sequencing data from each sample in the pool can be distinguished and separated. In one embodiment, each pooled sample may have its own internal quantification standard associated with its own unique set of sample-specific identification sequences, and wherein quantification is separately applied to each nucleic acid from each sample in the pool. As above with multiple nucleic acids in one sample, the normalization and quantification can be applied to multiple nucleic acids in multiple samples. The method includes calculating an input quantity (IQTi, IQTj, IQTk . . . IQTn) of multiple unknown nucleic acids in the pooled samples as IQTn=Normalized No. of unknown "n" nucleic acid sequencing reads attributed to the "nth" unknown nucleic acid*(Input Quantity of internal quantification standard/F).

In one embodiment, the method for performing a quantitative Next-Generation Sequencing (NGS) assay may include providing a set of assay specific positive controls to be sequenced, wherein the positive controls include a positive control corresponding to each of the one or more unknown nucleic acids sequenced in the assay. In one embodiment, the method for performing a quantitative Next-Generation Sequencing (NGS) assay may include applying assay-specific correction factors to each of the one or more unknown nucleic acids based on the sequence read count of the assay specific positive controls. If the efficiency of PCR amplification is not perfect or if the efficiency of the target and internal standard is different, the correction factor can depend on the quantity of positive control input into the reaction. Thus, in one embodiment, the quantity of positive controls should be in the middle of the targeted dynamic range of the corresponding targets.

In yet another aspect, a kit for normalizing and quantifying an unknown nucleic acid in a Next-Generation Sequencing (NGS) assay is described. The kit may include an internal quantification standard (IQS), wherein the IQS is a nucleic acid configured to be added in a known amount to a sample including an unknown nucleic acid to be sequenced; and instructions for using the IQS for normalizing a sequencing data set and for calculating an input quantity of the unknown nucleic acid. In one embodiment, the kit may include a set of IQSs to be added at different known concentrations for generating a standard curve for quantification of unknown nucleic acids. In one embodiment, the IQS provided in the kit may be configured to be added to the sample in the range of about $10^4\text{-}10^6$ copies/ml; however, the quantity of the IQS (or the IQSs) may be increased or decreased to expand or compress the upper and lower end of the range of detection. In one embodiment, using the internal quantification standard, sequencing data is normalized to retain a normalized number of sequencing reads (NORM), where NORM=No. of Sequencing Reads*(F/Observed No. of Sequencing Reads Originating from the Internal Quantification Standard), where 'F' is a fixed minimum expected number of the internal quantification standard sequencing reads, and using the internal quantification standard, an input quantity (IQT) of the unknown nucleic acid is calculated by IQT=Normalized No. of unknown nucleic acid sequencing reads originating from the unknown nucleic acid*(Input Quantity of internal quantification standard/F).

In one embodiment, the kit further includes sequencing-specific adapters for at least the internal quantification standard that include sequencing adapter sites and sample-specific identification sequences. In one embodiment, the kit may further include target-specific primers having custom overhangs configured for amplification of the internal quantification standard and for annealing or ligation to the sequencing-specific adapters.

In yet another aspect, a method for performing a comparator study is described. The method for performing the comparator study may include: providing a first assay comprising a single or multiplex amplification and detection of one or more target nucleic acids, the first assay having a limit of detection (LOD), and providing a second assay different than the first assay for confirming the detections and LOD of the first assay. The second assay should have at least the same LOD as the first assay, but it may have a lower LOD. In one or more embodiments, the second assay may include: preparing the sample including at least one internal quantification standard for sequencing; sequencing to generate a sequencing data set for the sample, wherein the sequencing data set includes sequencing reads observed from the target nucleic acid(s) and from the internal quantification standard; counting the number of sequencing reads in the sequencing data set originating from the target nucleic acid(s) and the internal quantification standard; and normalizing the sequencing data set, wherein the normalization (1) applies data acceptance/rejection criteria to the sequencing data set based on the presence of a minimum number of sequencing reads for the internal quantification standard for the sample and (2) ensures that substantially the same limit of detection (LOD) is applied to all unknown nucleic acids in the sequencing assay, and wherein the LOD of the second assay is substantially the same as an LOD of the first assay.

In one embodiment, the first assay may be a qualitative molecular diagnostic assay. In another embodiment, the first assay may be a semi-quantitative molecular diagnostic assay. In one embodiment, the first assay may further include adding one or more internal quantification standards to the sample, and performing quantitative two-step amplification. In one embodiment, the quantitative two-step amplification may include: amplifying the sample in a first-stage multiplex amplification mixture, the amplification mixture comprising a plurality of target primers, each target primer pair configured to amplify a different target that may be present in the sample, and at least one quantification standard primer pair, the quantification standard primer pair configured to amplify internal quantification standard nucleic acids, dividing the first-stage amplification mixture into a plurality of second-stage individual reactions, a first group of the plurality of second-stage individual reactions each comprising at least one primer pair configured to further amplify one of the different targets that may be present in the sample, and a second group of the plurality of second-stage individual reactions each comprising at least one primer pair configured to further amplify one of the internal quantification standard nucleic acids, and subjecting the plurality of second-stage individual reactions to amplification conditions to generate one or more target amplicons and a plurality of quantification standard amplicons, each quantification standard amplicon having an associated quantification standard crossing point (Cp), wherein each target nucleic acid has a Cp and each internal standard has a known concentration in the first assay and a known quantification standard Cp.

In one embodiment, the method may further include: generating a standard curve from two or more quantification standard crossing points (Cps) in the first assay; and quantifying each of the one or more target nucleic acids using the standard curve. In one embodiment, each of the target nucleic acids may be quantified in the first assay using a standard curve generated using a least squares regression line fit to $$\log_{10}(\text{Concentration})=(Cp-b)/\alpha$$

where Cp is the crossing point measured for each target, b, the intercept, represents the Cp value when the $\log_{10}$(concentration) of the target is zero, and a is the slope which represents the degree to which Cp changes with a single unit change in concentration.

In one embodiment, the second assay may further include normalizing the sequencing data set to retain NORM sequencing reads where NORM=No. of Sequencing Reads*(F/Observed No. of Sequencing Reads Originating from the Internal Quantification Standard). In one embodiment, the nucleic acids in the second assay may be quantified by calculating an input quantity (IQT) of each target nucleic acid in the sample by IQT=Normalized No. of target nucleic acid sequencing reads originating from a target nucleic acid*(Input Quantity of internal quantification standard/F), wherein 'F' is a fixed minimum expected number of the internal quantification standard sequencing reads. The same principle applies to calculating the input concentration of multiple unknown nucleic acids in the sample. An input quantity (IQTi, IQTj, IQTk . . . IQTn) of multiple target nucleic acids, if present, in the sample may be calculated as IQTn=Normalized No. of unknown "n" nucleic acid sequencing reads attributed to the "nth" unknown nucleic acid*(Input Quantity of internal quantification standard/F).

In one embodiment, 'F' in the second assay may be related to a limit of detection (LOD) of the second assay. The LOD of the second assay is selected to be substantially the same as an LOD of the first assay. In one embodiment, 'F' is related to the LOD of the assay. For instance, if 'F' is about $10^3$ for an input concentration of IQS of about $10^5$ copies/ml, then an LOD for an unknown nucleic acid in the sample is about $10^2$ copies per ml. If 'F' is about $10^4$ for the same input concentration of IQS (i.e., the read depth is increased and the weight of each read is increased correspondingly), then an LOD for an unknown nucleic acid in the sample is about 10 copies per ml. For a given input concentration of IQS, the LOD can be raised or lowered by increasing or decreasing the read depth (i.e., by increasing or decreasing the degree of 'F') and, correspondingly, increasing or decreasing the weight attributed to each individual sequencing read.

In one embodiment, the method for performing a comparator study may include pooling two or more samples and subjecting them to sequencing simultaneously, wherein the two or more samples are pooled after the preparing and before the sequencing. In one embodiment, each pooled sample may have associated therewith a unique set of sample-specific identification sequences such that the sequencing data from each sample in the pool can be distinguished and separated. In one embodiment, each pooled sample may have its own internal quantification standard associated with its own unique set of sample-specific identification sequences. As was described above with multiple nucleic acids in one sample, the normalization and quantification can be applied to multiple nucleic acids in multiple pooled samples. The method includes calculating an input quantity (IQTi, IQTj, IQTk IQTn) of multiple unknown nucleic acids in the pooled samples as IQTn=Normalized No. of unknown "n" nucleic acid sequencing reads attributed to the "nth" unknown nucleic acid*(Input Quantity of internal quantification standard/F).

In any of the foregoing embodiments, the sequencing assays, methods, and kits described herein do not include performing a relative quantification. That is, the sequencing assays, methods, and kits described herein do include an internal quantification standard of known concentration so it is not necessary to rely on relative numbers of sequencing reads or relative abundance of detected nucleic acids to determine the relative concentration of unknowns.

In any of the foregoing embodiments, the sequencing assays, methods, and kits described herein do not include performing a quantification in a reaction separate from the sequencing assay. That is, the sequencing assays, methods, and kits described herein do include an internal quantification standard of known concentration so it is not necessary to perform another separate reaction (e.g., a qPCR) to determine the input concentration of the nucleic acids in the sequencing reaction.

In any of the foregoing embodiments, the sequencing assays, methods, and kits described herein do not include using an assay- or template-specific quantification standard. That is, the sequencing assays, methods, and kits described herein do include a universal internal standard that can provide simultaneous quantification of multiple target species in any sequencing assay (e.g., an NGS assay) instead of relying on a standard designed for a specific assay or for a specific target.

In any of the foregoing embodiments, the sequencing assays, methods, and kits described herein do not include using a competitive template as a quantification standard. In general, a competitive template is a specific type of an assay- or template-specific quantification standard. However, a new competitive internal amplification control needs to be designed for each new assay and/or template to be sequenced. Instead, the sequencing assays, methods, and kits described herein include a universal internal standard that can provide simultaneous quantification of multiple target species in any sequencing assay (e.g., an NGS assay).

Described herein are:

A1. A method for read value normalization of a sequencing assay, comprising:

providing a sample including one or more unknown nucleic acids to be sequenced;

adding to the sample a known quantity of an internal quantification standard;

preparing the sample including the internal quantification standard for sequencing, wherein the preparing includes introducing sequencing-specific adapter sites and sample-specific identification sequences into the unknown nucleic acids and the internal quantification standard in the sample;

sequencing to generate a sequencing data set for the sample, wherein the sequencing data set includes sequencing reads observed from the unknown nucleic acid(s) and from the internal quantification standard;

counting the number of sequencing reads in the sequencing data set originating from the unknown nucleic acid(s) and the internal quantification standard; and normalizing the sequencing data set, wherein the normalization (1) applies data acceptance/rejection criteria to the sequencing data set based on the presence of a minimum number of sequencing reads for the internal quantification standard for the sample and (2) ensures that substantially the same limit of detection (LOD) is applied to all unknown nucleic acids in the sequencing assay.

A2. The method of clause A1, wherein each unknown nucleic acid in the sample has a concentration of about $0\text{-}10^{13}$ copies/ml (e.g., about $10^2\text{-}10^9$ copies/ml).

A3. The method of at least one of clause A1 or clause A2, wherein the known quantity of the internal quantification standard added to the sample is in the range of about $10^3\text{-}10^6$ copies/ml (e.g., about $10^5\text{-}10^6$ copies/ml).

A4. The method of one or more of clauses A1-A3, wherein a linear relationship exists between the known quantity of the internal quantification standard added to the sample and the number of sequencing reads for the internal quantification standard.

A5. The method of any one or more of clauses A1-A4, wherein normalizing the sequencing data set retains NORM sequencing reads, where NORM=No. of Sequencing Reads*(F/Observed No. of Sequencing Reads Originating from the Internal Quantification Standard), and wherein 'F' is a fixed minimum expected number of the internal quantification standard sequencing reads.

A6. The method of any one or more of clauses A1-A5, wherein 'F' is a sequencing read number value set to ensure a sequencing read depth sufficient for the LOD of the sequencing assay.

A7. The method of any one or more of clauses A1-A6, wherein the sequencing read depth is in a range of about 1000 internal quantification standard sequencing reads to about 100,000 internal quantification standard sequencing reads, preferably about 2000 internal quantification standard sequencing reads to about 75,000 internal quantification standard sequencing reads, more preferably about 5000 internal quantification standard sequencing reads to about 50,000 internal quantification standard sequencing reads, or most preferably at least 5000 internal quantification standard sequencing reads.

A8. The method of any one or more of clauses A1-A7, wherein unknown nucleic acid reads and internal quantification standard reads are each separately normalized by the same ratio ALPHA, where ALPHA=F/Observed No. of Sequencing Reads Originating from the Internal Quantification Standard.

A9. The method of any one or more of clauses A1-A8, further comprising calculating an input quantity (IQT) of the unknown nucleic acid in the sample after normalization, wherein the because the input quantity of the internal quantification standard is known, the input quantity (IQT) of the unknown nucleic acid can be calculated by IQT=Normalized No. of unknown nucleic acid sequencing reads attributed to the unknown nucleic acid*(Input Quantity of internal quantification standard/F).

A10. The method of any one or more of clauses A1-A9, further comprising calculating an input quantity (IQTi, IQTj, IQTk . . . IQTn) of multiple unknown nucleic acids, if present, in the sample after normalization as IQTn=Normalized No. of unknown "n" nucleic acid sequencing reads attributed to the "nth" unknown nucleic acid*(Input Quantity of internal quantification standard/F).

A11. The method of any one or more of clauses A1-A10, wherein preparing the sample includes sample lysis, recovery of nucleic acids from the lysate and optionally purifying the recovered nucleic acids, and attaching introducing primer binding sites and sample-specific identification sequences into regions of the nucleic acids to be sequenced.

A12. The method of any one or more of clauses A1-A11, wherein the attaching includes one of:

amplifying the nucleic acids to be sequenced in a amplification reaction using target-specific primers having dual-indexed sequencing overhangs that include sequencing primer binding sites and sample-specific identification sequences, or fragmenting the nucleic acids to be sequenced and ligating to the fragmented nucleic acids sequencing-specific adapters that include sequencing primer binding sites and sample-specific identification sequences.

A13. The method of any one or more of clauses A1-A12, wherein amplifying the nucleic acids to be sequenced includes:

performing a first multiplex PCR reaction using target-specific primers having custom overhangs, performing a first nucleic acid purification, performing a second PCR reaction using dual-indexed sequencing adapter primers that anneal or ligate to the overhangs introduced in the first PCR, wherein the dual-indexed sequencing adapter primers are target-independent and include sequencing primer binding sites and sample-specific identification sequences, performing a second nucleic acid purification.

A14. The method of any one or more of clauses A1-A13, further comprising limiting one or more of concentration of the target-specific primers or cycle number in the first multiplex PCR reaction to plateau amplification of nucleic acids present at concentration greater than about $10^7$ copies/ml and to preserve nucleic acids less than about $10^7$ copies/ml in the exponential amplification phase.

A15. The method of any one or more of clauses A1-A14, further comprising pooling two or more samples and subjecting them to sequencing simultaneously, wherein the two or more samples are pooled after the preparing and before the sequencing.

A16. The method of any one or more of clauses A1-A15, wherein 2-1000 samples are pooled after the preparing and before the sequencing, preferably 2-500 samples are pooled after the preparing and before the sequencing, more preferably 2-100 samples are pooled after the preparing and before the sequencing, more preferably 2-50 samples are pooled after the preparing and before the sequencing, or most preferably 2-32 samples are pooled after the preparing and before the sequencing.

A17. The method of any one or more of clauses A1-A16, wherein each pooled sample has associated therewith a unique set of sample-specific identification sequences such that the sequencing data from each sample in the pool can be distinguished and separated.

A18. The method of any one or more of clauses A1-A17, wherein each pooled sample has its own internal quantification standard associated with its own unique set of sample-specific identification sequences, and wherein the normalization is separately applied to each sample in the pool.

A19. The method of any one or more of clauses A1-A18, wherein the normalization separately (1) applies data acceptance/rejection criteria to each sample in the pool and (2) ensures that substantially the same limit of detection (LOD) is applied to all unknown nucleic acids in each sample.

A20. The method of any one or more of clauses A1-A19, further comprising calculating an input quantity (IQTi, IQTj, IQTk . . . IQTn) of multiple unknown nucleic acids in the pooled samples after normalization as IQTn=Normalized No. of unknown "n" nucleic acid sequencing reads attributed to the "nth" unknown nucleic acid*(Input Quantity of internal quantification standard/F).

A21. The method of any one or more of clauses A1-A20, wherein the sequencing assay is a next-generation sequencing assay.

A22. The method of any one or more of clauses A1-A21, wherein the sequencing assay does not include performing a relative quantification.

A23. The method of any one or more of clauses A1-A22, wherein the sequencing assay does not include performing a quantification in a reaction separate from the sequencing assay.

A24. The method of any one or more of clauses A1-A23, wherein the sequencing assay does not include using an assay- or template-specific quantification standard.

A25. The method of any one or more of clauses A1-A24, wherein the sequencing assay does not include using a competitive template as a quantification standard.

B1. A method for performing a quantitative Next-Generation Sequencing (NGS) assay, comprising:

providing a sample including one or more unknown nucleic acids to be sequenced;

adding to the sample a known quantity of an internal quantification standard;

preparing the sample including the internal quantification standard for sequencing;

sequencing the unknown nucleic acids and the internal quantification standard in the sample to generate a sequencing data;

counting the number of sequencing reads in the sequencing data set originating from the unknown nucleic acid(s) and the internal quantification standard; and normalizing the sequencing data set and calculating an input quantity (IQT) of the unknown nucleic acid in the by IQT=Normalized No. of unknown nucleic acid sequencing reads originating from the unknown nucleic acid*(Input Quantity of internal quantification standard/F), wherein 'F' is a fixed minimum expected number of the internal quantification standard sequencing reads.

B2. The method of clause B1, wherein each unknown nucleic acid in the sample has a concentration of about $0\text{-}10^{13}$ copies/ml (e.g., about $10^2\text{-}10^9$ copies/ml).

B3. The method of at least one of clause B1 or clause B2, wherein the known quantity of the internal quantification standard added to the sample is in the range of about $10^4\text{-}10^6$ copies/ml (e.g., about $10^5\text{-}10^6$ copies/ml).

B4. The method of any one or more of clauses B1-B3, further comprising normalizing the sequencing data set by NORM=No. of Sequencing Reads*(F/Observed No. of Sequencing Reads Originating from the Internal Quantification Standard).

B5. The method of any one or more of clauses B1-B4, wherein the normalization separately (1) applies data acceptance/rejection criteria to each sample in the assay and (2) ensures that substantially the same limit of detection (LOD) is applied to all unknown nucleic acids in each sample across multiple samples pooled together used across multiple users, days, etc.

B6. The method of any one or more of clauses B1-B5, wherein the unknown nucleic acids have a concentration of about $10^2$-$10^{10}$ copies/ml or, preferably, about $10^2$-$10^9$ copies/ml.

B7. The method of any one or more of clauses B1-B6, wherein 'F' is related to a limit of detection (LOD) of the NGS assay, and wherein if 'F' is about $1\times10^3$-$5\times10^3$ then an LOD for the unknown nucleic acid is about $10^2$-$10^3$ copies per ml.

B8. The method of any one or more of clauses B1-B7, wherein 'F' is related to a limit of detection (LOD) of the NGS assay, and wherein if 'F' is about $1\times10^4$-$5\times10^4$ then an LOD for the unknown nucleic acid is about $10^1$-$10^2$ copies per ml.

B9. The method of any one or more of clauses B1-B8, further comprising calculating an input quantity (IQTi, IQTj, IQTk . . . IQTn) of multiple unknown nucleic acids, if present, in the sample as IQTn=Normalized No. of unknown "n" nucleic acid sequencing reads attributed to the "nth" unknown nucleic acid*(Input Quantity of internal quantification standard/F).

B10. The method of any one or more of clauses B1-B9, further comprising pooling two or more samples and subjecting them to sequencing simultaneously, wherein the two or more samples are pooled after the preparing and before the sequencing.

B11. The method of any one or more of clauses B1-B10, wherein each pooled sample has associated therewith a unique set of sample-specific identification sequences such that the sequencing data from each sample in the pool can be distinguished and separated.

B12. The method of any one or more of clauses B1-B11, wherein each pooled sample has its own internal quantification standard associated with its own unique set of sample-specific identification sequences, and wherein quantification is separately applied to each nucleic acid from each sample in the pool.

B13. The method of any one or more of clauses B1-B12, further comprising calculating an input quantity (IQTi, IQTj, IQTk . . . IQTn) of multiple unknown nucleic acids in the pooled samples as IQTn=Normalized No. of unknown "n" nucleic acid sequencing reads attributed to the "nth" unknown nucleic acid*(Input Quantity of internal quantification standard/F).

B14. The method of any one or more of clauses B1-B13, further comprising providing a set of assay specific positive controls to be sequenced in the sample, wherein the positive controls include a positive control corresponding to each of the one or more unknown nucleic acids sequenced in the assay.

B15. The method of any one or more of clauses B1-B14, further comprising applying assay-specific correction factors to each of the one or more unknown nucleic acids based on the sequencing of the assay specific positive controls.

B16. The method of any one or more of clauses B1-B15, wherein performing the quantitative NGS assay does not include performing a relative quantification.

B17. The method of any one or more of clauses B1-B16, wherein performing the quantitative NGS assay does not include performing a quantification in a reaction separate from the sequencing assay.

B18. The method of any one or more of clauses B1-B17, wherein performing the quantitative NGS assay does not include using an assay- or template-specific quantification standard.

B19. The method of any one or more of clauses B1-B18, wherein performing the quantitative NGS assay does not include using a competitive template as a quantification standard.

C1. A kit for normalizing and quantifying an unknown nucleic acid in a Next-Generation Sequencing (NGS) assay, comprising:

an internal quantification standard, wherein the internal quantification standard is a nucleic acid configured to be added in a known amount to a sample including an unknown nucleic acid to be sequenced; and instructions for using the internal quantification standard for normalizing a sequencing data set and for calculating an input quantity of the unknown nucleic acid, wherein the internal quantification standard is configured to be added to the sample in the range of about $10^4$-$10^6$ copies/ml, wherein, using the internal quantification standard, sequencing data is normalized by NORM=No. of Sequencing Reads*(F/Observed No. of Sequencing Reads Originating from the Internal Quantification Standard), where 'F' is a fixed minimum expected number of the internal quantification standard sequencing reads, and wherein, using the internal quantification standard, an input quantity (IQT) of the unknown nucleic acid is calculated by IQT=Normalized No. of unknown nucleic acid sequencing reads originating from the unknown nucleic acid*(Input Quantity of internal quantification standard/F).

C2. The kit of clause C1, further comprising sequencing-specific adapters for at least the internal quantification standard that include sequencing primer binding sites and sample-specific identification sequences.

C3. The kit of at least one of clause C1 or clause C2, further comprising target-specific primers having custom overhangs configured for amplification of the internal quantification standard and for annealing or ligation to the sequencing-specific adapters.

C4. The kit of at least one of clauses C1-C3, further comprising two or more internal quantification standards, wherein the each of the two or more internal quantification standards are configured to be added to the sample at different known concentrations for generating a standard curve for quantification of unknown nucleic acids.

D1. A method for performing a comparator study, comprising providing a first assay comprising multiplex amplification and detection of one or more target nucleic acids, the first assay having a limit of detection (LOD);

providing a second assay different than the first assay for confirming the detections and LOD of the first assay, wherein the second assay includes:

preparing the sample including at least one internal quantification standard for sequencing;

sequencing to generate a sequencing data set for the sample, wherein the sequencing data set includes sequencing reads observed from the target nucleic acid(s) and from the internal quantification standard;

counting the number of sequencing reads in the sequencing data set originating from the target nucleic acid(s) and the internal quantification standard; and normalizing the sequencing data set, wherein the normalization (1) applies data acceptance/rejection criteria to the sequencing data set based on the presence of a minimum number of sequencing reads for the internal quantification standard for the sample and (2) ensures that substantially the same limit of detection (LOD) is applied to all unknown nucleic acids in the sequencing assay, and wherein the LOD of the second assay is substantially the same as an LOD of the first assay.

D2. The method of clause D1, wherein the first assay further comprises adding one or more internal quantification standards to the sample, and performing quantitative two-step amplification on the sample, the quantitative two-step amplification comprising:

amplifying the sample in a first-stage multiplex amplification mixture, the amplification mixture comprising a plurality of target primers, each target primer configured to amplify a different target that may be present in the sample, and at least one quantification standard primer, the quantification standard primer configured to amplify internal quantification standard nucleic acids, dividing the first-stage amplification mixture into a plurality of second-stage individual reactions, a first group of the plurality of second-stage individual reactions each comprising at least one primer configured to further amplify one of the different targets that may be present in the sample, and a second group of the plurality of second-stage individual reactions each comprising at least one primer configured to further amplify one of the internal quantification standard nucleic acids, and subjecting the plurality of second-stage individual reactions to amplification conditions to generate one or more target amplicons and a plurality of quantification standard amplicons, each quantification standard amplicon having an associated quantification standard Cp, wherein each target nucleic acid has a crossing point (Cp) and each internal standard has a known concentration in the first assay and a known quantification standard Cp.

D3. The method of at least one of clause D1 or clause D2, further comprising generating a standard curve from the quantification standard Cps; and quantifying each of the one or more target nucleic acids using the standard curve.

D4. The method of any one or more of clauses D1-D3, wherein each of the target nucleic acids is quantified using a standard curve generated using a least squares regression line fit to $$\log_{10}(\text{Concentration})=(Cp-b)/a$$

where Cp is the crossing point measured for each target, b, the intercept, represents the Cp value when the $\log_{10}$ (concentration) of the target is zero, and a is the slope which represents the degree to which Cp changes with a single unit change in concentration.

D5. The method of any one or more of clauses D1-D4, further comprising normalizing the sequencing data set in the second assay by NORM=No. of Sequencing Reads*(F/Observed No. of Sequencing Reads Originating from the Internal Quantification Standard).

D6. The method of any one or more of clauses D1-D5, calculating an input quantity (IQT) of each target nucleic acid in the sample by IQT=Normalized No. of target nucleic acid sequencing reads originating from a target nucleic acid*(Input Quantity of internal quantification standard/F), wherein 'F' is a fixed minimum expected number of the internal quantification standard sequencing reads.

D7. The method of any one or more of clauses D1-D6, wherein 'F' is related to a limit of detection (LOD) of the second assay, and wherein the LOD of the second assay is selected to be substantially the same as an LOD of the first assay.

D8. The method of any one or more of clauses D1-D7, wherein if 'F' is about $1\times10^3$-$5\times10^3$ then the LOD for detection of the target nucleic acid(s) in the second assay is about $10^2$-$10^3$ copies per ml.

D9. The method of any one or more of clauses D1-D, wherein if 'F' is about $1\times10^4$-$5\times10^4$ then the LOD for detection of the target nucleic acid(s) in the second assay is about $10^1$-$10^2$ copies per ml.

D10. The method of any one or more of clauses D1-D9, further comprising calculating an input quantity (IQTi, IQTj, IQTk . . . IQTn) of multiple target nucleic acids, if present, in the sample as IQTn=Normalized No. of unknown "n" nucleic acid sequencing reads attributed to the "nth" unknown nucleic acid*(Input Quantity of internal quantification standard/F).

D11. The method of any one or more of clauses D1-D10, further comprising pooling two or more samples and subjecting them to sequencing simultaneously in the second assay, wherein the two or more samples are pooled after the preparing and before the sequencing.

D12. The method of any one or more of clauses D1-D11, wherein each pooled sample has associated therewith a unique set of sample-specific identification sequences such that the sequencing data from each sample in the pool can be distinguished and separated.

D13. The method of any one or more of clauses D1-D12, wherein each pooled sample has its own internal quantification standard associated with its own unique set of sample-specific identification sequences, and wherein quantification is separately applied to each nucleic acid from each sample in the pool.

D14. The method of any one or more of clauses D1-D13, further comprising calculating an input quantity (IQTi, IQTj, IQTk . . . IQTn) of multiple unknown nucleic acids in the pooled samples as IQTn=Normalized No. of unknown "n" nucleic acid sequencing reads attributed to the "nth" unknown nucleic acid*(Input Quantity of internal quantification standard/F).

D15. The method of any one or more of clauses D1-D14, wherein the quantification standard nucleic acids and the target nucleic acids all have similar amplification efficiencies and sequencing efficiencies.

D16. The method of any one or more of clauses D1-D15, wherein the second assay is a next-generation sequencing assay.

D17. The method of any one of clauses D1-D16, wherein the second assay does not include performing a relative quantification, D18. The method of any one of clauses D1-D17, wherein the second assay does not include performing a quantification in a reaction separate from the sequencing assay, D19. The method of any one of clauses D1-D18, wherein the second assay does not include using an assay- or template-specific quantification standard, D20. The method of any one of clauses D1-D19, wherein the second assay does not include using a competitive template as a quantification standard.

In any of the foregoing embodiments of the method for performing a comparator study, the second assay may be a next-generation sequencing assay.

This summary is provided to introduce a selection of concepts in a simplified form that are further described below in the Drawings and the Detailed Description. This Summary is not intended to identify key features or essential features of the claimed subject matter, nor is it intended to be used as an aid in determining the scope of the claimed subject matter.

Additional features and advantages will be set forth in the description that follows, and in part will be clear based on the description, or may be learned by the practice of the invention. These and other features will become more fully apparent from the following description and appended claims, or may be learned by the practice of the invention as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION

Figure 1:
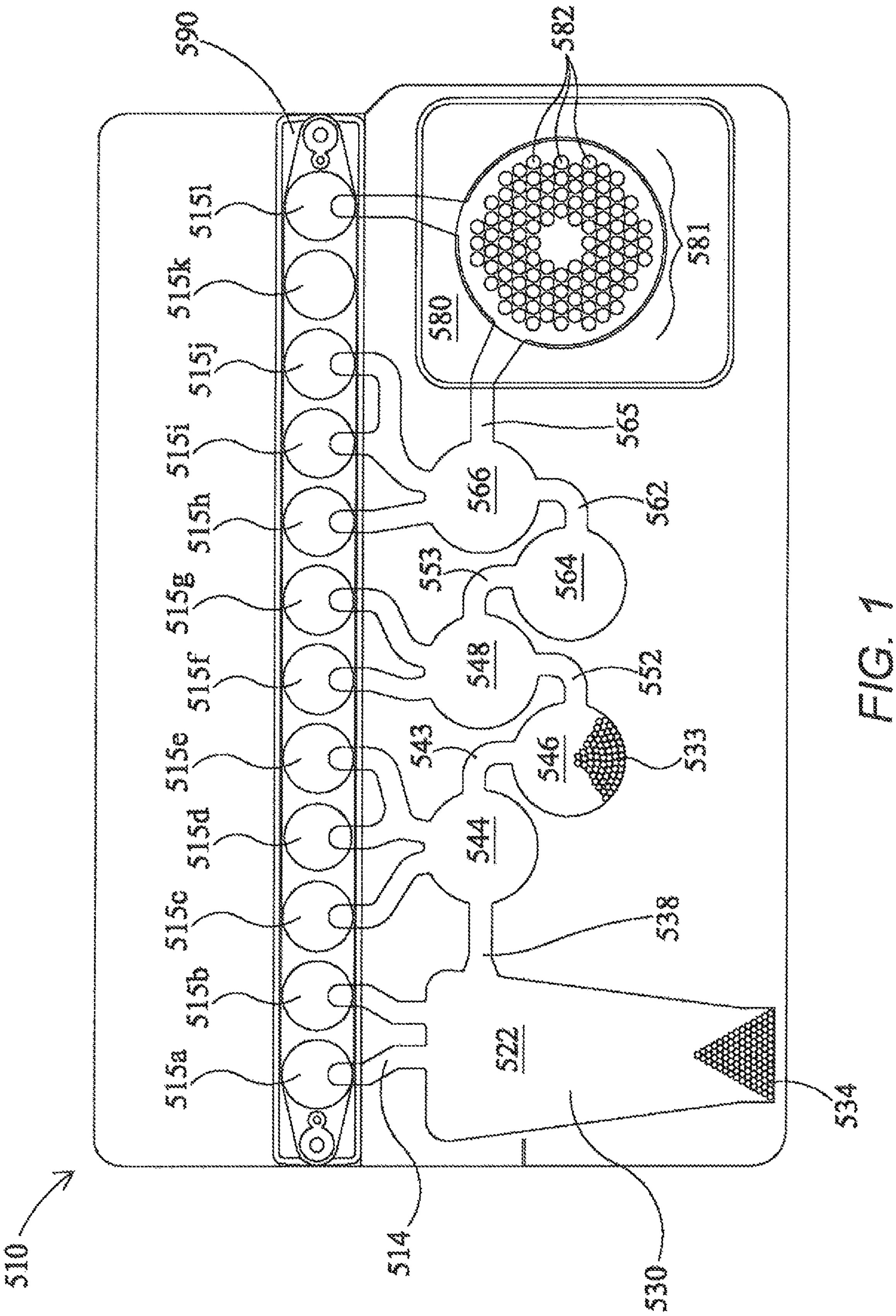
FIG. 1 shows a flexible pouch according to one embodiment of the present invention.

Example embodiments are described below with reference to the accompanying drawings. Many different forms and embodiments are possible without deviating from the spirit and teachings of this disclosure and so the disclosure should not be construed as limited to the example embodiments set forth herein. Rather, these example embodiments are provided so that this disclosure will be thorough and complete, and will convey the scope of the disclosure to those skilled in the art. In the drawings, the sizes and relative sizes of layers and regions may be exaggerated for clarity. Like reference numbers refer to like elements throughout the description.

Unless defined otherwise, all terms (including technical and scientific terms) used herein have the same meaning as commonly understood by one of ordinary skill in the art to which the present disclosure pertains. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. While a number of methods and materials similar or equivalent to those described herein can be used in the practice of the present disclosure, only certain exemplary materials and methods are described herein.

All publications, patent applications, patents or other references mentioned herein are incorporated by reference in their entirety. In case of a conflict in terminology, the present specification is controlling.

Various aspects of the present disclosure, including devices, systems, methods, etc., may be illustrated with reference to one or more exemplary implementations. As used herein, the terms “exemplary” and “illustrative” mean “serving as an example, instance, or illustration,” and should not necessarily be construed as preferred or advantageous over other implementations disclosed herein. In addition, reference to an “implementation” or “embodiment” of the present disclosure or invention includes a specific reference to one or more embodiments thereof, and vice versa, and is intended to provide illustrative examples without limiting the scope of the invention, which is indicated by the appended claims rather than by the following description.

It will be noted that, as used in this specification and the appended claims, the singular forms “a,” “an,” and “the” include plural referents unless the content clearly dictates otherwise. Thus, for example, reference to “a tile” includes one, two, or more tiles. Similarly, reference to a plurality of referents should be interpreted as comprising a single referent and/or a plurality of referents unless the content and/or context clearly dictate otherwise. Thus, reference to "tiles" does not necessarily require a plurality of such tiles. Instead, it will be appreciated that independent of conjugation; one or more tiles are contemplated herein.

As used throughout this application the words "can" and "may" are used in a permissive sense (i.e., meaning having the potential to), rather than the mandatory sense (i.e., meaning must). Additionally, the terms "including," "having," "involving," "containing," "characterized by," variants thereof (e.g., "includes," "has," "involves," "contains," etc.), and similar terms as used herein, including the claims, shall be inclusive and/or open-ended, shall have the same meaning as the word "comprising" and variants thereof (e.g., "comprise" and "comprises"), and do not exclude additional, un-recited elements or method steps, illustratively.

As used herein, directional and/or arbitrary terms, such as "top," "bottom," "left," "right," "up," "down," "upper," "lower," "inner," "outer," "internal," "external," "interior," "exterior," "proximal," "distal," "forward," "reverse," and the like can be used solely to indicate relative directions and/or orientations and may not be otherwise intended to limit the scope of the disclosure, including the specification, invention, and/or claims.

It will be understood that when an element is referred to as being "coupled," "connected," or "responsive" to, or "on," another element, it can be directly coupled, connected, or responsive to, or on, the other element, or intervening elements may also be present. In contrast, when an element is referred to as being "directly coupled," "directly connected," or "directly responsive" to, or "directly on," another element, there are no intervening elements present.

Example embodiments of the present inventive concepts are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments of the present inventive concepts should not be construed as limited to the particular shapes of regions illustrated herein but are to include deviations in shapes that result, for example, from manufacturing. Accordingly, the regions illustrated in the figures are schematic in nature and their shapes are not intended to illustrate the actual shape of a region of a device and are not intended to limit the scope of example embodiments.

It will be understood that although the terms "first," "second," etc. may be used herein to describe various elements, these elements should not be limited by these terms. These terms are only used to distinguish one element from another. Thus, a "first" element could be termed a "second" element without departing from the teachings of the present embodiments.

It is also understood that various implementations described herein can be utilized in combination with any other implementation described or disclosed, without departing from the scope of the present disclosure. Therefore, products, members, elements, devices, apparatus, systems, methods, processes, compositions, and/or kits according to certain implementations of the present disclosure can include, incorporate, or otherwise comprise properties, features, components, members, elements, steps, and/or the like described in other implementations (including systems, methods, apparatus, and/or the like) disclosed herein without departing from the scope of the present disclosure. Thus, reference to a specific feature in relation to one implementation should not be construed as being limited to applications only within said implementation.

The headings used herein are for organizational purposes only and are not meant to be used to limit the scope of the description or the claims. To facilitate understanding, like reference numerals have been used, where possible, to designate like elements common to the figures. Furthermore, where possible, like numbering of elements have been used in various figures. Furthermore, alternative configurations of a particular element may each include separate letters appended to the element number.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 5%. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

The word "or" as used herein means any one member of a particular list and also includes any combination of members of that list.

By "sample" is meant an animal; a tissue or organ from an animal; a cell (either within a subject, taken directly from a subject, or a cell maintained in culture or from a cultured cell line); a cell lysate (or lysate fraction) or cell extract; a solution containing one or more molecules derived from a cell, cellular material, or viral material (e.g., a polypeptide or nucleic acid); or a solution containing a non-naturally occurring nucleic acid illustratively a cDNA or next-generation sequencing library, which is assayed as described herein. A sample may also be any body fluid or excretion (for example, but not limited to, blood, urine, stool, saliva, tears, bile, or cerebrospinal fluid) that may or may not contain host or pathogen cells, cell components, or nucleic acids.

The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU), modified or treated bases and non-phosphodiester internucleoside linkages (e.g., peptide nucleic acid (PNA) or thiodiester linkages). In particular, nucleic acids can include, without limitation, DNA, cDNA, gDNA, ssDNA, dsDNA, RNA, including all RNA types such as miRNA, mtRNA, rRNA, including coding or non-coding regions, or any combination thereof.

By "probe," "primer," or "oligonucleotide" is meant a single-stranded nucleic acid molecule of defined sequence that can base-pair to a second nucleic acid molecule that contains a complementary sequence (the "target"). The stability of the resulting hybrid depends upon the length, GC content, and the extent of the base-pairing that occurs. The extent of base-pairing is affected by parameters such as the degree of complementarity between the probe and target molecules and the degree of stringency of the hybridization conditions. The degree of hybridization stringency is affected by parameters such as temperature, salt concentration, and the concentration of organic molecules such as formamide, and is determined by methods known to one skilled in the art. Probes, primers, and oligonucleotides may be detectably-labeled, either radioactively, fluorescently, or non-radioactively, by methods well-known to those skilled in the art. dsDNA binding dyes may be used to detect dsDNA. It is understood that a “primer” is specifically configured to be extended by a polymerase, whereas a “probe” or “oligonucleotide” may or may not be so configured. As a probe, the oligonucleotide could be used as part of many fluorescent PCR primer- and probe-based chemistries that are known in the art, including those sharing the use of fluorescence quenching and/or fluorescence resonance energy transfer (FRET) configurations, such as 5'nuclease probes (TaqMan® probes), dual hybridization probes (HybProbes®), or Eclipse® probes or molecular beacons, or Amplifluor® assays, such as Scorpions®, LUX® or QZyme® PCR primers, including those with natural or modified bases.

By “dsDNA binding dyes” is meant dyes that fluoresce differentially when bound to double-stranded DNA than when bound to single-stranded DNA or free in solution, usually by fluorescing more strongly. While reference is made to dsDNA binding dyes, it is understood that any suitable dye may be used herein, with some non-limiting illustrative dyes described in U.S. Pat. No. 7,387,887, herein incorporated by reference. Other signal producing substances may be used for detecting nucleic acid amplification and melting, illustratively enzymes, antibodies, etc., as are known in the art.

By “specifically hybridizes” is meant that a probe, primer, or oligonucleotide recognizes and physically interacts (that is, base-pairs) with a substantially complementary nucleic acid (for example, a sample nucleic acid) under high stringency conditions, and does not substantially base pair with other nucleic acids.

By “high stringency conditions” is meant at about melting temperature (Tm) minus 5° C. (i.e., 5° below the Tm of the nucleic acid). Functionally, high stringency conditions are used to identify nucleic acid sequences having at least 80% sequence identity.

While PCR is the amplification method used in the examples herein, it is understood that any amplification method that uses a primer may be suitable. Such suitable procedures include polymerase chain reaction (PCR) of any type (single-step, two-steps, or others); strand displacement amplification (SDA); nucleic acid sequence-based amplification (NASBA); cascade rolling circle amplification (CRCA), loop-mediated isothermal amplification of DNA (LAMP); isothermal and chimeric primer-initiated amplification of nucleic acids (ICAN); target based-helicase dependent amplification (HDA); transcription-mediated amplification (TMA), Next-Generation Sequencing (NGS) techniques, and the like. Therefore, when the term PCR is used, it should be understood to include other alternative amplification methods, including amino acid quantification methods. For amplification methods without discrete cycles, reaction time may be used where measurements are made in cycles or Cp, and additional reaction time may be added where additional PCR cycles are added in the embodiments described herein. It is understood that protocols may need to be adjusted accordingly.

As used herein, the term “crossing point” (Cp) (or, alternatively, cycle threshold (Ct), quantification cycle (Cq), or a synonymous term used in the art) refers to the number of cycles of PCR required to obtain a fluorescence signal above some threshold value for a given PCR product (e.g., target or internal standard(s)), as determined experimentally. The cycle where each reaction rises above the threshold is dependent on the amount of target (i.e., reaction template) present at the beginning of the PCR reaction. The threshold value may typically be set at the point where the product’s fluorescence signal is detectable above background fluorescence; however, other threshold values may be employed. As an alternative to setting a somewhat arbitrary threshold value, Cp may be determined by calculating the point for a reaction at which a first, second, or nth order derivative has its maximum value, which determines the cycle at which the curvature of the amplification curve is maximal. An illustrative derivative method was taught in U.S. Pat. No. 6,303,305, herein incorporated by reference in its entirety. Nevertheless, it usually does not matter much where or how the threshold is set, so long as the same threshold is used for all reactions that are being compared. Other points may be used as well, as are known in the art, and any such point may be substituted for Cp, Ct, or Cq in any of the methods discussed herein.

By “sample processing control” is meant a pathogen, microorganism, cell, whether living or not, nucleic acid, or any particle, natural or synthetic, possessing the ability to mimic a pathogen or a portion of it, or a nucleic acid, and its behavior during the workflow of the sample. A sample processing control is often included in the device in a known amount to control some or all of the steps of the workflow followed by the sample, illustratively to ensure that the sample has been correctly lysed, the nucleic acids of the potentially infecting target pathogens have been correctly extracted and purified, and that correct amplification and detection of specific sequences of target pathogens has taken place.

Illustratively, a microorganism (illustratively *Schizosaccharomyces pombe* (*S. pombe*)) that is used as sample processing control mimics as closely as possible the target microorganisms to be detected and quantified. The sample processing control particle may reproduce the structure (such as membrane(s) and/or capsid and/or envelop) of the pathogens to be detected, allowing it to mimic the behavior of the pathogen and its target nucleic acids along the workflow. The goal of the sample process control is to ensure that the lysis and nucleic acid extraction yield of the target are similar to the yield of the sample processing control, and that the purified nucleic acids are processed appropriately to ensure an optimal amplification/detection. For qualitative results, a pathogen can be reported as positive or negative, or may be reported as undetermined if a run control failed. The sample processing control may be one of several run controls and should be positive, and perhaps be within a specified range, to validate the run, since some inhibitory conditions can decrease the yield of extraction, purification, or PCR amplification/detection. The sample processing control can be used to monitor this kind of inhibition, the reduction of the yield being similar between the sample processing control and the target pathogen. For qualitative results, such inhibition, if undetected, can lead to a false negative result. For quantitative results, an inhibition of one of the steps of the workflow can provide an underestimated quantification result. Therefore, several illustrative embodiments of the present invention use at least one sample processing control (SPC) for at least two goals:

1) to control and validate the workflow: the classic role of the SPC as described above, and 2) to aid in the quantification of a targeted nucleic acid(s) in a tested sample: a new role of the SPC that is also used as quantification standard.

Illustratively, the SPC follows some or all of the process to which the sample is subjected. Thus, the SPC may be added prior to or during the step of lysis of the sample. The sample processing control may be chosen based on the type of target pathogen(s). For example, a bacteriophage as the PhiX 174 can be chosen for an assay focused on viruses, a bacteriophage being a good candidate to mimic the target viruses, or a yeast, such as *S. pombe*, for use in a broad bacteria and yeast quantification assay.

If a single pathogen is to be detected, the two amplification assays, illustratively PCR assays (target pathogen and sample processing control used as a quantification standard) can be designed to reach the same or similar thermodynamics characteristics and enable an accurate quantification (as in Example 5) using a synthetic quantification standard.

For the quantification of multiple pathogens (i.e., multiplex amplification), it can be difficult to fit the amplification protocols, illustratively the PCR design, of the sample processing control, with the protocol of the amplification assay, illustratively a PCR assay for each pathogen, to obtain the same thermodynamics characteristics, illustratively because of sequence variability and amplicon length. As a consequence, the PCR efficiencies of the different target pathogens may be different. For this purpose, a correction factor can be calculated for each pathogen that correlates the quantification obtained with the quantification standard and the imported standard curve.

In an alternative to the synthetic quantification standard, the calibration could be performed against a known natural microorganism with known concentrations or against other naturally occurring nucleic acid templates.

In another embodiment of the invention, it is also possible to have reliable quantification of a pathogen in any amplification system with at least two different, illustratively three or four different sample processing controls, provided that these sample processing controls could be identified via a known technique of identification such as sequence-specific probes that are labeled fluorescently, radioactively, chemiluminescently, enzymatically, or the like, as are known in the art.

While various examples herein reference human targets and human pathogens, these examples are illustrative only. Methods, kits, and devices described herein may be used to detect and sequence a wide variety of nucleic acid sequences from a wide variety of samples, including, human, veterinary, industrial, and environmental.

Various embodiments disclosed herein use a self-contained nucleic acid analysis pouch to assay a sample for the presence of various biological substances, illustratively antigens and nucleic acid sequences, illustratively in a single closed system. Such systems, including pouches and instruments for use with the pouches, are disclosed in more detail in U.S. Pat. Nos. 8,394,608; and 8,895,295; and U.S. Patent Application No. 2014-0283945, herein incorporated by reference. However, it is understood that such instruments and pouches are illustrative only, and the nucleic acid preparation and amplification reactions discussed herein may be performed in any of a variety of open or closed system sample vessels as are known in the art, including 96-well plates, plates of other configurations, arrays, carousels, and the like, using a variety of nucleic acid purification and amplification systems, as are known in the art. While the terms "sample well", "amplification well", "amplification container", or the like are used herein, these terms are meant to encompass wells, tubes, and various other reaction containers, as are used in these amplification systems. Such amplification systems may include a single multiplex step in an amplification container and may optionally include a plurality of second-stage individual or lower-order multiplex reactions in a plurality of individual reaction wells. In one embodiment, the pouch is used to assay for multiple pathogens. The pouch may include one or more blisters used as sample wells, illustratively in a closed system. Illustratively, various steps may be performed in the optionally disposable pouch, including nucleic acid preparation, primary large volume multiplex PCR, dilution of primary amplification product, and secondary PCR, culminating with optional real-time detection or post-amplification analysis such as melting-curve analysis. Further, it is understood that while the various steps may be performed in pouches of the present invention, one or more of the steps may be omitted for certain uses, and the pouch configuration may be altered accordingly.

FIG. 1 shows an illustrative pouch 510 that may be used in various embodiments, or may be reconfigured for various embodiments. Pouch 510 is similar to FIG. 15 of U.S. Pat. No. 8,895,295, with like items numbered the same. Fitment 590 is provided with entry channels 515*a* through 515*l*, which also serve as reagent reservoirs or waste reservoirs. Illustratively, reagents may be freeze dried in fitment 590 and rehydrated prior to use. Blisters 522, 544, 546, 548, 564, and 566, with their respective channels 514, 538, 543, 552, 553, 562, and 565 are similar to blisters of the same number of FIG. 15 of U.S. Pat. No. 8,895,295. Second-stage reaction zone 580 of FIG. 1 is similar to that of U.S. Pat. No. 8,895,295, but the second-stage wells 582 of high density array 581 are arranged in a somewhat different pattern. The more circular pattern of high density array 581 of FIG. 1 eliminates wells in corners and may result in more uniform filling of second-stage wells 582. As shown, the high density array 581 is provided with 102 second-stage wells 582. Pouch 510 is suitable for use in the FilmArray® instrument (BioFire Diagnostics, LLC, Salt Lake City, UT). However, it is understood that the pouch embodiment is illustrative only.

While other containers may be used, illustratively, pouch 510 is formed of two layers of a flexible plastic film or other flexible material such as polyester, polyethylene terephthalate (PET), polycarbonate, polypropylene, polymethylmethacrylate, and mixtures thereof that can be made by any process known in the art, including extrusion, plasma deposition, and lamination. Metal foils or plastics with aluminum lamination also may be used. Other barrier materials are known in the art that can be sealed together to form the blisters and channels. If plastic film is used, the layers may be bonded together, illustratively by heat sealing. Illustratively, the material has low nucleic acid binding capacity.

For embodiments employing fluorescent monitoring, plastic films that are adequately low in absorbance and auto-fluorescence at the operative wavelengths are preferred. Such material could be identified by testing different plastics, different plasticizers, and composite ratios, as well as different thicknesses of the film. For plastics with aluminum or other foil lamination, the portion of the pouch that is to be read by a fluorescence detection device can be left without the foil. For example, if fluorescence is monitored in second-stage wells 582 of the second-stage reaction zone 580 of pouch 510, then one or both layers at wells 582 would be left without the foil. In the example of PCR, film laminates composed of polyester (Mylar, DuPont, Wilmington DE) of about 0.0048 inch (0.1219 mm) thick and polypropylene films of 0.001-0.003 inch (0.025-0.076 mm) thick perform well. Illustratively, pouch 510 is made of a clear material capable of transmitting approximately 80%-90% of incident light.

In the illustrative embodiment, the materials are moved between blisters by the application of pressure, illustratively pneumatic pressure, upon the blisters and channels. Accordingly, in embodiments employing pressure, the pouch material illustratively is flexible enough to allow the pressure to have the desired effect. The term "flexible" is herein used to describe a physical characteristic of the material of pouch. The term "flexible" is herein defined as readily deformable by the levels of pressure used herein without cracking, breaking, crazing, or the like. For example, thin plastic sheets, such as Saran™ wrap and Ziploc® bags, as well as thin metal foil, such as aluminum foil, are flexible. However, only certain regions of the blisters and channels need be flexible, even in embodiments employing pneumatic pressure. Further, only one side of the blisters and channels need to be flexible, as long as the blisters and channels are readily deformable. Other regions of the pouch 510 may be made of a rigid material or may be reinforced with a rigid material.

Illustratively, a plastic film is used for pouch 510. A sheet of metal, illustratively aluminum, or other suitable material, may be milled or otherwise cut, to create a die having a pattern of raised surfaces. When fitted into a pneumatic press (illustratively A-5302-PDS, Janesville Tool Inc., Milton WI), illustratively regulated at an operating temperature of 195° C., the pneumatic press works like a printing press, melting the sealing surfaces of plastic film only where the die contacts the film. Various components, such as PCR primers (illustratively spotted onto the film and dried), antigen binding substrates, magnetic beads, and zirconium silicate beads may be sealed inside various blisters as the pouch 510 is formed. Reagents for sample processing can be spotted onto the film prior to sealing, either collectively or separately. In one embodiment, nucleotide tri-phosphates (NTPs) are spotted onto the film separately from polymerase and primers, essentially eliminating activity of the polymerase until the reaction is hydrated by an aqueous sample. If the aqueous sample has been heated prior to hydration, this creates the conditions for a true hot-start PCR and reduces or eliminates the need for expensive chemical hot-start components.

Pouch 510 may be used in a manner similar to that described in U.S. Pat. No. 8,895,295. In one illustrative embodiment, a 300 μl mixture comprising the sample to be tested (100 μl) and lysis buffer (200 μl) is injected into an injection port (not shown) in fitment 590 near entry channel 515*a*, and the sample mixture is drawn into entry channel 515*a*. Water is also injected into a second injection port (not shown) of the fitment 590 adjacent entry channel 515*l*, and is distributed via a channel (not shown) provided in fitment 590, thereby hydrating up to eleven different reagents, each of which were previously provided in dry form at entry channels 515*b* through 515*l*. These reagents illustratively may include freeze-dried PCR reagents, DNA extraction reagents, wash solutions, immunoassay reagents, or other chemical entities. Illustratively, the reagents are for nucleic acid extraction, first-stage multiplex PCR, dilution of the multiplex reaction, and preparation of second-stage PCR reagents, as well as control reactions. In the embodiment shown in FIG. 1, all that need be injected is the sample solution in one injection port and water in the other injection port. After injection, the two injection ports may be sealed. For more information on various configurations of pouch 510 and fitment 590, see U.S. Pat. No. 8,895,295, already incorporated by reference.

After injection, the sample is moved from injection channel 515*a* to lysis blister 522 via channel 514. Lysis blister 522 is provided with beads or particles 534, such as ceramic beads, and is configured for vortexing via impaction using rotating blades or paddles provided within the FilmArray® instrument. Bead-milling, by shaking or vortexing the sample in the presence of lysing particles such as zirconium silicate (ZS) beads 534, is an effective method to form a lysate. It is understood that, as used herein, terms such as "lyse," "lysing," and "lysate" are not limited to rupturing cells, but that such terms include disruption of non-cellular particles, such as viruses.

Figure 2:
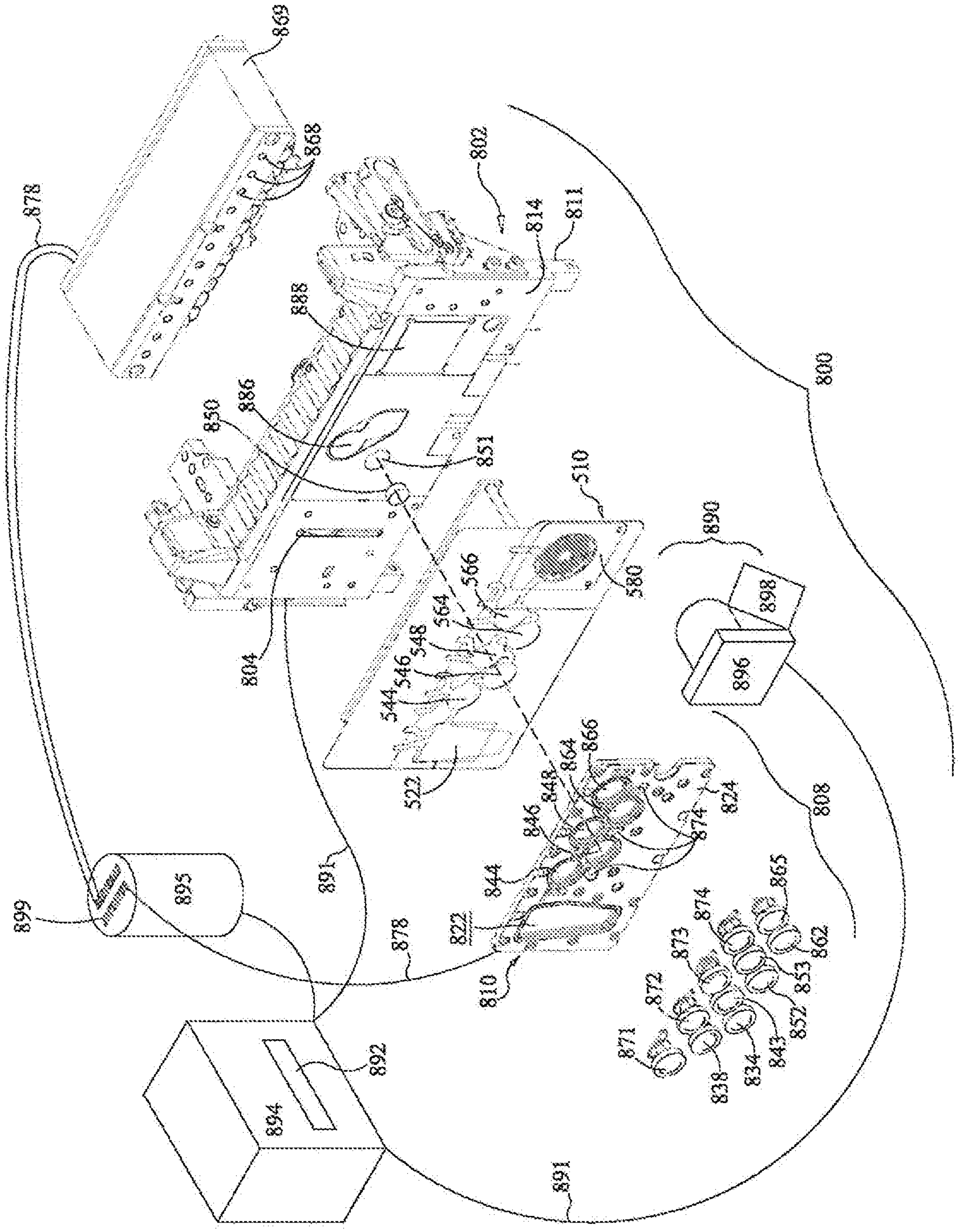
FIG. 2 together form an exploded perspective view of an instrument for use with the pouch of FIG. 1, including the pouch of FIG. 1, according to an example embodiment of the present invention.
Figure 4:
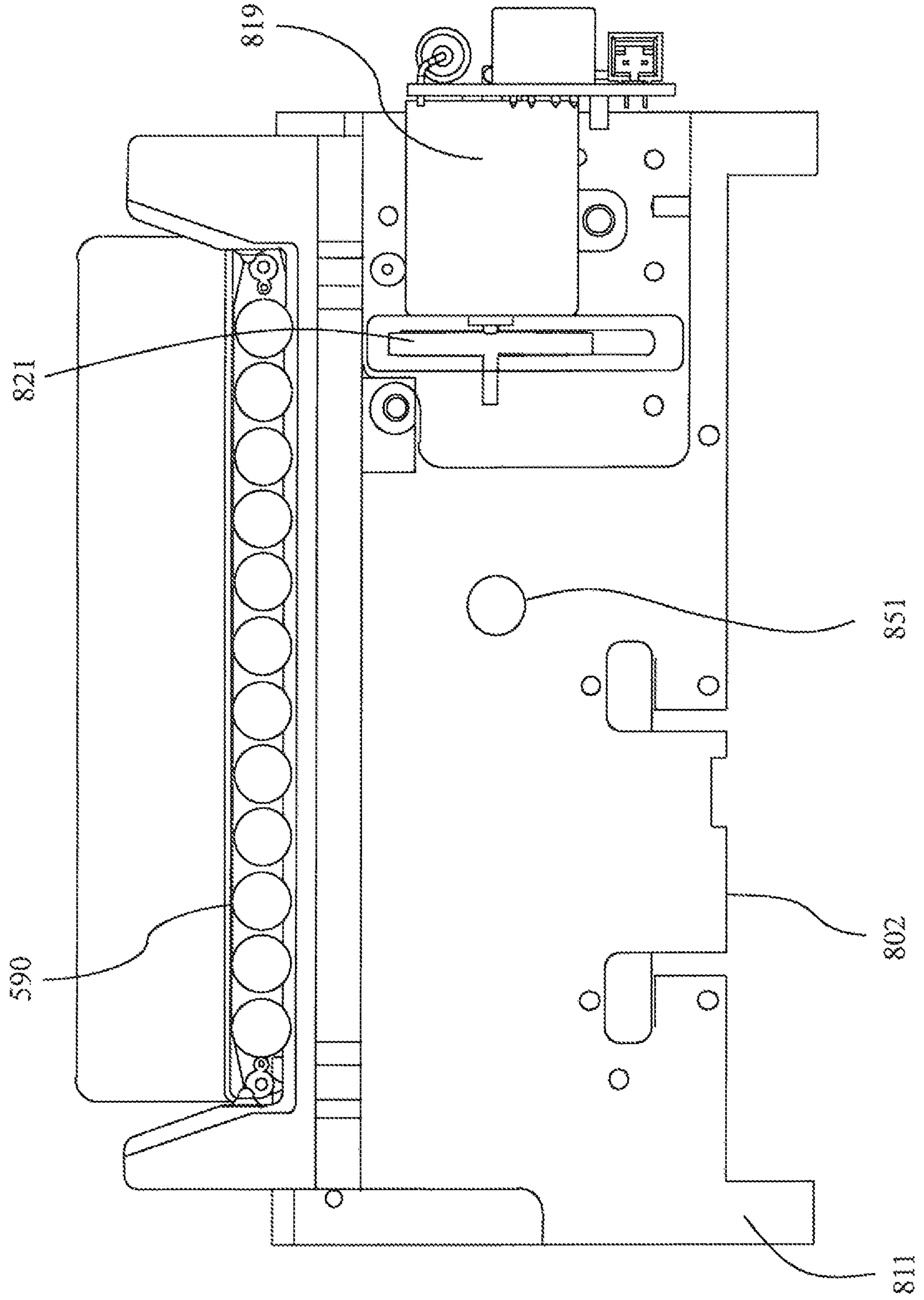
FIG. 4 shows a motor used in one illustrative embodiment of the instrument of FIG. 2.

FIG. 4 shows a bead beating motor 819, comprising blades 821 that may be mounted on a first side 811 of support member 802, of instrument 800 shown in FIG. 2. Blades may extend through slot 804 to contact pouch 510. It is understood, however, that motor 819 may be mounted on other structures of instrument 800. In one illustrative embodiment, motor 819 is a Mabuchi RC-280SA-2865 DC Motor (Chiba, Japan), mounted on support member 802. In one illustrative embodiment, the motor is turned at 5,000 to 25,000 rpm, more illustratively 10,000 to 20,000 rpm, and still more illustratively approximately 15,000 to 18,000 rpm. For the Mabuchi motor, it has been found that 7.2V provides sufficient rpm for lysis. It is understood, however, that the actual speed may be somewhat slower when the blades 821 are impacting pouch 510. Other voltages and speeds may be used for lysis depending on the motor and paddles used. Optionally, controlled small volumes of air may be provided into the bladder 822 adjacent lysis blister 522. It has been found that in some embodiments, partially filling the adjacent bladder with one or more small volumes of air aids in positioning and supporting lysis blister during the lysis process. Alternatively, other structure, illustratively a rigid or compliant gasket or other retaining structure around lysis blister 522, can be used to restrain pouch 510 during lysis. It is also understood that motor 819 is illustrative only, and other devices may be used for milling, shaking, or vortexing the sample.

Once the cells have been adequately lysed, the sample is moved through channel 538, blister 544, and channel 543, to blister 546, where the sample is mixed with a nucleic acid-binding substance, such as silica-coated magnetic beads 533. The mixture is allowed to incubate for an appropriate length of time, illustratively approximately 10 seconds to 10 minutes. A retractable magnet located within the instrument adjacent blister 546 captures the magnetic beads 533 from the solution, forming a pellet against the interior surface of blister 546. The liquid is then moved out of blister 546 and back through blister 544 and into blister 522, which is now used as a waste receptacle. One or more wash buffers from one or more of injection channels 515*c* to 515*e* are provided via blister 544 and channel 543 to blister 546. Optionally, the magnet is retracted and the magnetic beads 533 are washed by moving the beads back and forth from blisters 544 and 546 via channel 543. Once the magnetic beads 533 are washed, the magnetic beads 533 are recaptured in blister 546 by activation of the magnet, and the wash solution is then moved to blister 522. This process may be repeated as necessary to wash the lysis buffer and sample debris from the nucleic acid-binding magnetic beads 533.

After washing, elution buffer stored at injection channel 515*f* is moved to blister 548, and the magnet is retracted. The solution is cycled between blisters 546 and 548 via channel

552, breaking up the pellet of magnetic beads 533 in blister 546 and allowing the captured nucleic acids to dissociate from the beads and come into solution. The magnet is once again activated, capturing the magnetic beads 533 in blister 546, and the eluted nucleic acid solution is moved into blister 548.

First-stage PCR master mix from injection channel 515*g* is mixed with the nucleic acid sample in blister 548. Optionally, the mixture is mixed by forcing the mixture between 548 and 564 via channel 553. After several cycles of mixing, the solution is contained in blister 564, where a pellet of first-stage PCR primers is provided, at least one set of primers for each target, and first-stage multiplex PCR is performed. If RNA targets are present, a reverse-transcription (RT) step may be performed prior to or simultaneously with the first-stage multiplex PCR. First-stage multiplex PCR temperature cycling in the FilmArray® instrument is illustratively performed for 15-30 cycles, although other levels of amplification may be desirable, depending on the requirements of the specific application. The first-stage PCR master mix may be any of various master mixes, as are known in the art. In one illustrative example, the first-stage PCR master mix may be any of the chemistries disclosed in US2015/0118715, herein incorporated by reference, for use with PCR protocols taking 20 seconds or less per cycle.

After first-stage PCR has proceeded for the desired number of cycles, the sample may be diluted, illustratively by forcing most of the sample back into blister 548, leaving only a small amount in blister 564, and adding second-stage PCR master mix from injection channel 515*i*. Alternatively, a dilution buffer from 515*i* may be moved to blister 566 then mixed with the amplified sample in blister 564 by moving the fluids back and forth between blisters 564 and 566. If desired, dilution may be repeated several times, using dilution buffer from injection channels 515*j* and 515*k*, or injection channel 515*k* may be reserved for sequencing or for other post-PCR analysis, and then adding second-stage PCR master mix from injection channel 515*h* to some or all of the diluted amplified sample. It is understood that the level of dilution may be adjusted by altering the number of dilution steps or by altering the percentage of the sample discarded prior to mixing with the dilution buffer or second-stage PCR master mix comprising components for amplification, illustratively a polymerase, dNTPs, and a suitable buffer, although other components may be suitable, particularly for non-PCR amplification methods. If desired, this mixture of the sample and second-stage PCR master mix may be pre-heated in blister 564 prior to movement to second-stage wells 582 for second-stage amplification. Such preheating may obviate the need for a hot-start component (antibody, chemical, or otherwise) in the second-stage PCR mixture.

The illustrative second-stage PCR master mix is incomplete, lacking primer pairs, and each of the 102 second-stage wells 582 is pre-loaded with a specific PCR primer pair (or sometimes multiple pairs of primers). If desired, second-stage PCR master mix may lack other reaction components, and these components may be pre-loaded in the second-stage wells 582 as well. Each primer pair may be similar to or identical to a first-stage PCR primer pair or may be nested within the first-stage primer pair. Movement of the sample from blister 564 to the second-stage wells 582 completes the PCR reaction mixture. Once high density array 581 is filled, the individual second-stage reactions are sealed in their respective second-stage blisters by any number of means, as is known in the art. Illustrative ways of filling and sealing the high density array 581 without cross-contamination are discussed in U.S. Pat. No. 8,895,295, already incorporated by reference. Illustratively, the various reactions in wells 582 of high density array 581 are simultaneously thermal cycled, illustratively with one or more Peltier devices, although other means for thermal cycling are known in the art.

In certain embodiments, second-stage PCR master mix contains the dsDNA binding dye LCGreen® Plus (BioFire Diagnostics, LLC) to generate a signal indicative of amplification. However, it is understood that this dye is illustrative only, and that other signals may be used, including other dsDNA binding dyes and probes that are labeled fluorescently, radioactively, chemiluminescently, enzymatically, or the like, as are known in the art. Alternatively, wells 582 of array 581 may be provided without a signal, with results reported through subsequent processing.

Figure 3:
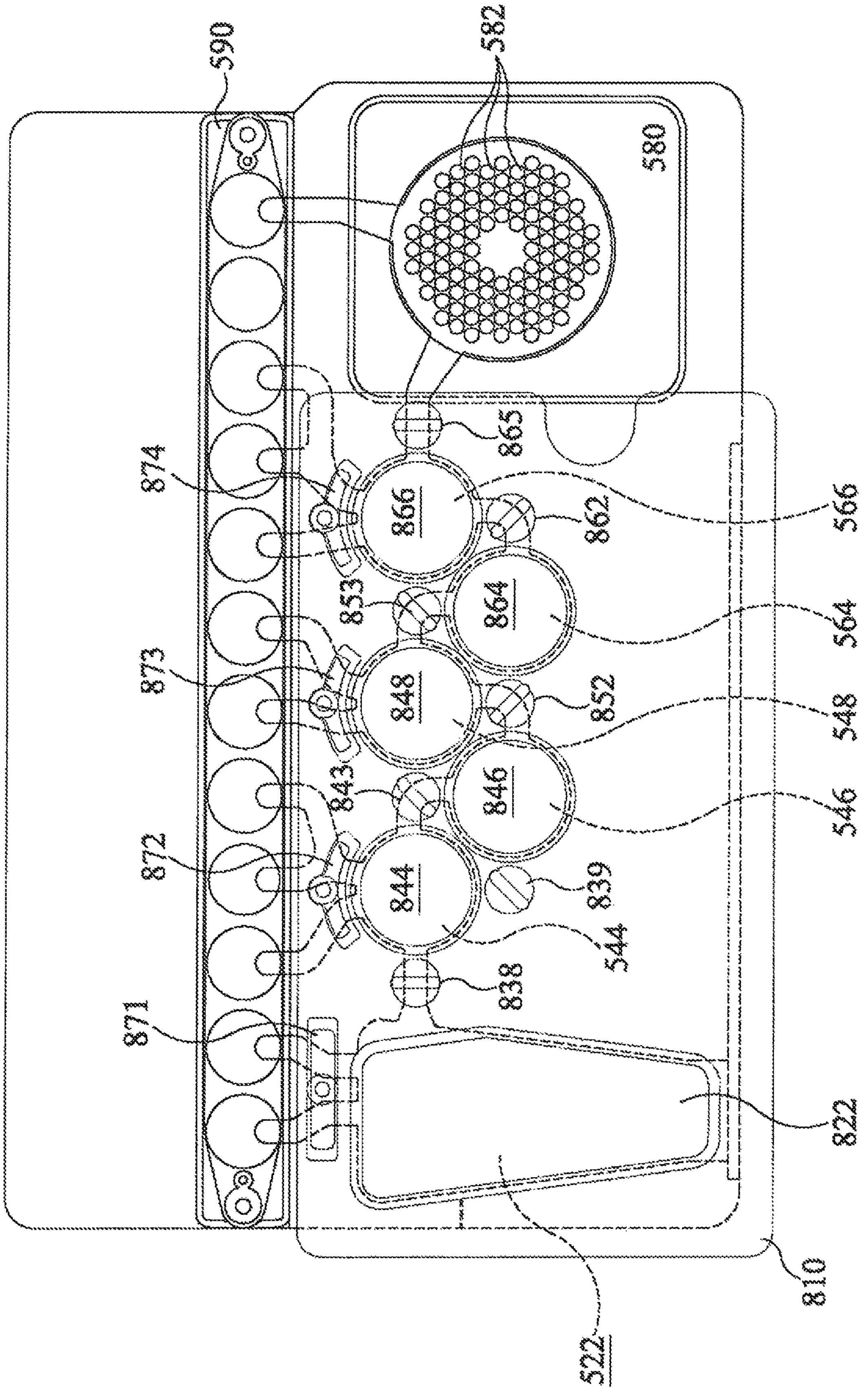
FIG. 3 shows a partial cross-sectional view of the instrument of FIG. 2, including the bladder components of FIG. 2, with the pouch of FIG. 1 shown in dashed lines, according to an example embodiment of the present invention.

When pneumatic pressure is used to move materials within pouch 510, in one embodiment a "bladder" may be employed. The bladder assembly 810, a portion of which is shown in FIGS. 2 and 3, includes a bladder plate 824 housing a plurality of inflatable bladders 822, 844, 846, 848, 864, and 866, each of which may be individually inflatable, illustratively by a compressed gas source. Because the bladder assembly 810 may be subjected to compressed gas and used multiple times, the bladder assembly 810 may be made from tougher or thicker material than the pouch. Alternatively, bladders 822, 844, 846, 848, 864, and 866 may be formed from a series of plates fastened together with gaskets, seals, valves, and pistons. Other arrangements are within the scope of this invention.

Success of the secondary PCR reactions is dependent upon template generated by the multiplex first-stage reaction. Typically, PCR is performed using DNA of high purity. Methods such as phenol extraction or commercial DNA extraction kits provide DNA of high purity. Samples processed through the pouch 510 may require accommodations be made to compensate for a less pure preparation. PCR may be inhibited by components of biological samples, which is a potential obstacle. Illustratively, hot-start PCR, higher concentration of taq polymerase enzyme, adjustments in $MgCl_2$ concentration, adjustments in primer concentration, and addition of adjuvants (such as DMSO, TMSO, or glycerol) optionally may be used to compensate for lower nucleic acid purity. While purity issues are likely to be more of a concern with first-stage amplification and single-stage PCR, it is understood that similar adjustments may be provided in the second-stage amplification as well.

When pouch 510 is placed within the instrument 800, the bladder assembly 810 is pressed against one face of the pouch 510, so that if a particular bladder is inflated, the pressure will force the liquid out of the corresponding blister in the pouch 510. In addition to bladders corresponding to many of the blisters of pouch 510, the bladder assembly 810 may have additional pneumatic actuators, such as bladders or pneumatically-driven pistons, corresponding to various channels of pouch 510. FIGS. 2 and 3 show an illustrative plurality of pistons or hard seals 838, 843, 852, 853, and 865 that correspond to channels 538, 543, 553, and 565 of pouch 510, as well as seals 871, 872, 873, 874 that minimize backflow into fitment 590. When activated, hard seals 838, 843, 852, 853, and 865 form pinch valves to pinch off and close the corresponding channels. To confine liquid within a particular blister of pouch 510, the hard seals are activated over the channels leading to and from the blister, such that the actuators function as pinch valves to pinch the channels shut. Illustratively, to mix two volumes of liquid in different blisters, the pinch valve actuator sealing the connecting channel is activated, and the pneumatic bladders over the blisters are alternately pressurized, forcing the liquid back and forth through the channel connecting the blisters to mix the liquid therein. The pinch valve actuators may be of various shapes and sizes and may be configured to pinch off more than one channel at a time. While pneumatic actuators are discussed herein, it is understood that other ways of providing pressure to the pouch are contemplated, including various electromechanical actuators such as linear stepper motors, motor-driven cams, rigid paddles driven by pneumatic, hydraulic or electromagnetic forces, rollers, rocker-arms, and in some cases, cocked springs. In addition, there are a variety of methods of reversibly or irreversibly closing channels in addition to applying pressure normal to the axis of the channel. These include kinking the bag across the channel, heat-sealing, rolling an actuator, and a variety of physical valves sealed into the channel such as butterfly valves and ball valves. Additionally, small Peltier devices or other temperature regulators may be placed adjacent the channels and set at a temperature sufficient to freeze the fluid, effectively forming a seal. Also, while the design of FIG. 1 is adapted for an automated instrument featuring actuator elements positioned over each of the blisters and channels, it is also contemplated that the actuators could remain stationary, and the pouch 510 could be transitioned in one or two dimensions such that a small number of actuators could be used for several of the processing stations including sample disruption, nucleic-acid capture, first and second-stage PCR, and other applications of the pouch 510 such as immuno-assay and immuno-PCR. Rollers acting on channels and blisters could prove particularly useful in a configuration in which the pouch 510 is translated between stations. Thus, while pneumatic actuators are used in the presently disclosed embodiments, when the term "pneumatic actuator" is used herein, it is understood that other actuators and other ways of providing pressure may be used, depending on the configuration of the pouch and the instrument.

Other prior art instruments teach PCR within a sealed flexible container. See, e.g., U.S. Pat. Nos. 6,645,758, 6,780,617, and 9,586,208, herein incorporated by reference. However, including the cell lysis within the sealed PCR vessel can improve ease of use and safety, particularly if the sample to be tested may contain a biohazard. In the embodiments illustrated herein, the waste from cell lysis, as well as that from all other steps, remains within the sealed pouch. However, it is understood that the pouch contents could be removed for further testing.

FIG. 2 show an illustrative instrument 800 that could be used with pouch 510. Instrument 800 includes a support member 802 that could form a wall of a casing or be mounted within a casing. Instrument 800 may also include a second support member (not shown) that is optionally movable with respect to support member 802, to allow insertion and withdrawal of pouch 510. Illustratively, a lid may cover pouch 510 once pouch 510 has been inserted into instrument 800. In another embodiment, both support members may be fixed, with pouch 510 held into place by other mechanical means or by pneumatic pressure.

In the illustrative example, heaters 886 and 888 are mounted on support member 802. However, it is understood that this arrangement is illustrative only and that other arrangements are possible. Bladder plate 810, with bladders 822, 844, 846, 848, 864, 866, hard seals 838, 843, 852, 853, seals 871, 872, 873, 874 form bladder assembly 808 may illustratively be mounted on a moveable support structure that may be moved toward pouch 510, such that the pneumatic actuators are placed in contact with pouch 510. When pouch 510 is inserted into instrument 800 and the movable support member is moved toward support member 802, the various blisters of pouch 510 are in a position adjacent to the various bladders of bladder assembly 810 and the various seals of assembly 808, such that activation of the pneumatic actuators may force liquid from one or more of the blisters of pouch 510 or may form pinch valves with one or more channels of pouch 510. The relationship between the blisters and channels of pouch 510 and the bladders and seals of assembly 808 is illustrated in more detail in FIG. 3.

Each pneumatic actuator is connected to compressed air source 895 via valves 899. While only several hoses 878 are shown in FIG. 2, it is understood that each pneumatic fitting is connected via a hose 878 to the compressed gas source 895. Compressed gas source 895 may be a compressor, or, alternatively, compressed gas source 895 may be a compressed gas cylinder, such as a carbon dioxide cylinder. Compressed gas cylinders are particularly useful if portability is desired. Other sources of compressed gas are within the scope of this invention.

Assembly 808 is illustratively mounted on a movable support member, although it is understood that other configurations are possible.

Several other components of instrument 810 are also connected to compressed gas source 895. A magnet 850, which is mounted on a second side 814 of support member 802, is illustratively deployed and retracted using gas from compressed gas source 895 via hose 878, although other methods of moving magnet 850 are known in the art. Magnet 850 sits in recess 851 in support member 802. It is understood that recess 851 can be a passageway through support member 802, so that magnet 850 can contact blister 546 of pouch 510. However, depending on the material of support member 802, it is understood that recess 851 need not extend all the way through support member 802, as long as when magnet 850 is deployed, magnet 850 is close enough to provide a sufficient magnetic field at blister 546, and when magnet 850 is retracted, magnet 850 does not significantly affect any magnetic beads 533 present in blister 546. While reference is made to retracting magnet 850, it is understood that an electromagnet may be used and the electromagnet may be activated and inactivated by controlling flow of electricity through the electromagnet. Thus, while this specification discusses withdrawing or retracting the magnet, it is understood that these terms are broad enough to incorporate other ways of withdrawing the magnetic field. It is understood that the pneumatic connections may be pneumatic hoses or pneumatic air manifolds, thus reducing the number of hoses or valves required.

The various pneumatic pistons 868 of pneumatic piston array 869 are also connected to compressed gas source 895 via hoses 878. While only two hoses 878 are shown connecting pneumatic pistons 868 to compressed gas source 895, it is understood that each of the pneumatic pistons 868 are connected to compressed gas source 895. Twelve pneumatic pistons 868 are shown.

A pair of heating/cooling devices, illustratively Peltier heaters, are mounted on a second side 814 of support 802. First-stage heater 886 is positioned to heat and cool the contents of blister 564 for first-stage PCR. Second-stage heater 888 is positioned to heat and cool the contents of second-stage blisters 582 of pouch 510, for second-stage PCR. It is understood, however, that these heaters could also be used for other heating purposes, and that other heaters may be use, as appropriate for the particular application. Other configurations are possible.

When fluorescent detection is desired, an optical array 890 may be provided. As shown in FIG. 2, optical array 890 includes a light source 898, illustratively a filtered LED light source, filtered white light, or laser illumination, and a camera 896. Camera 896 illustratively has a plurality of photodetectors each corresponding to a second-stage well 582 in pouch 510. Alternatively, camera 896 may take images that contain all of the second-stage wells 582, and the image may be divided into separate fields corresponding to each of the second-stage wells 582. Depending on the configuration, optical array 890 may be stationary, or optical array 890 may be placed on movers attached to one or more motors and moved to obtain signals from each individual second-stage well 582. It is understood that other arrangements are possible.

As shown, a computer 894 controls valves 899 of compressed air source 895, and thus controls all of the pneumatics of instrument 800. Computer 894 also controls heaters 886 and 888, and optical array 890. Each of these components is connected electrically, illustratively via cables 891, although other physical or wireless connections are within the scope of this invention. It is understood that computer 894 may be housed within instrument 800 or may be external to instrument 800. Further, computer 894 may include built-in circuit boards that control some or all of the components, may calculate amplification curves, melting curves, Cps, Cts, standard curves, and other related data, and may also include an external computer, such as a desktop or laptop PC, to receive and display data from the optical array. An interface, illustratively a keyboard interface, may be provided including keys for inputting information and variables such as temperatures, cycle times, etc. Illustratively, a display 892 is also provided. Display 892 may be an LED, LCD, or other such display, for example.

Example 1—High Density PCR

In one example, it is known that standard commercial immunofluorescence assays for the common respiratory viruses can detect seven viruses: adenovirus, PIV1, PIV2, PIV3, RSV, Influenza A, and Influenza B. A more complete panel illustratively would include assays for other viruses including: coronavirus, human metapneumovirus, rhinovirus, and non-HRV enterovirus. For highly variable viruses such as Adenovirus or HRV, it is desirable to use multiple primers to target all of the branches of the virus' lineage (illustratively 4 outer and 4 inner primer sets respectively). For other viruses such as coronavirus, there are 4 distinct lineages (229E, NL63, OC43, HKU1) that do not vary from one season to another, but they have diverged sufficiently enough that separate primer sets are required. The FilmArray® Respiratory Panel (BioFire Diagnostics, LLC of Salt Lake City, UT) includes Adenovirus, Coronavirus HKU1, Coronavirus NL63, Coronavirus 229E, Coronavirus OC43, Human Metapneumovirus, Human Rhinovirus/Enterovirus, Influenza A, Influenza A/H1, Influenza A/H3, Influenza A/H1-2009, Influenza B, Parainfluenza Virus 1, Parainfluenza Virus 2, Parainfluenza Virus 3, Parainfluenza Virus 4, and Respiratory Syncytial Virus. In addition to these viruses, the FilmArray® Respiratory Panel includes three bacteria: *Bordetella pertussis, Chlamydophila pneumoniae*, and *Mycoplasma pneumoniae*. The high density array 581 is able to accommodate such a panel in a single pouch 510. Other panels are available for the FilmArray®, each assaying for at least 20 pathogens.

The illustrative second-stage PCR master mix contains the dsDNA binding dye LCGreen® Plus to generate a signal indicative of amplification. However, it is understood that this dye is illustrative only, and that other signals may be used, including other dsDNA binding dyes, and probes that are labeled fluorescently, radioactively, chemiluminescently, enzymatically, or the like, as are known in the art.

The illustrative FilmArray instrument is programmed to make positive or negative calls for each second-stage reaction based on a post-PCR melt. The melt curve must produce a melt peak (first derivative maximum or negative first derivative maximum) within a pre-defined temperature range, for the call to be positive. It is understood that this method of calling each second-stage reaction is illustrative only, and that calls could be made using real-time amplification data or by other means, as are known in the art.

Example 2—Designing Quantification Standards for Multiplex PCR

In systems such as the FilmArray where a single multiplex PCR is performed in one reaction chamber, it is not convenient to generate standard curves using 10-fold dilutions of a single reference template, since the individual levels cannot be distinguished easily. For example, if a single reference template is added into the single first-stage reaction chamber at concentrations of 10 copies, 100 copies and 1000 copies, the final concentration of the reference template in that chamber will be 1110 copies, and absent some other label, the individual dilutions are not distinguishable. Furthermore, in a two-step multiplex PCR system, standard curves generated solely in the nested second-stage PCR may be of limited value for quantification, as single-plex standard template amplification reactions may not accurately reflect all of the upstream manipulations that the sample undergoes or may not be amplified with similar efficiencies, and, therefore, may not be reflective of the entire process.

In this illustrative example, different nucleic acid templates (illustratively varying in sequence and/or length), illustratively synthetic quantification standards, are used to represent different levels of a dilution series. In one illustrative embodiment, assays for all of the synthetic quantification standards have similar amplification efficiency and produce the same or similar Cp values at each given dilution point in the multiplex setting. Illustratively, all target assays, are optimized for the same performance characteristics, including efficiency, although corrections may be applied to adjust for assay-specific variation in efficiency.

In one illustrative example, outer and inner amplicon sizes for the quantification standards may be representative of amplicon sizes for the quantitative target assays. Also, the sequence or GC content may be the same or similar in between the priming regions. Illustratively, the sequences may be identical with an exception of at least one inner priming region, which should be different enough to avoid cross-reactivity between inner assays. If sequences differ only by inner primer binding region, then the same PCR1 primers may be used to amplify all quantification standards, thus minimizing potential differences in the PCR1 assay performances. Moreover, if labels are used, the sequences may be identical, and if labels are not used, even a slight difference in sequence can provide for detection, illustratively in a second-stage single-plex reaction. However, it is understood that these parameters are illustrative only, and other means for detection and controlling amplification efficiencies are possible. It is understood that quantification standards present in the multiplex reaction should be designed to match reaction parameters, such as $Mg^{2+}$, primer concentration, Tm, and cycling conditions. It is also understood that it is desirable to minimize non-specific amplification of the synthetic templates in the multiplex PCR reaction.

Figure 5:
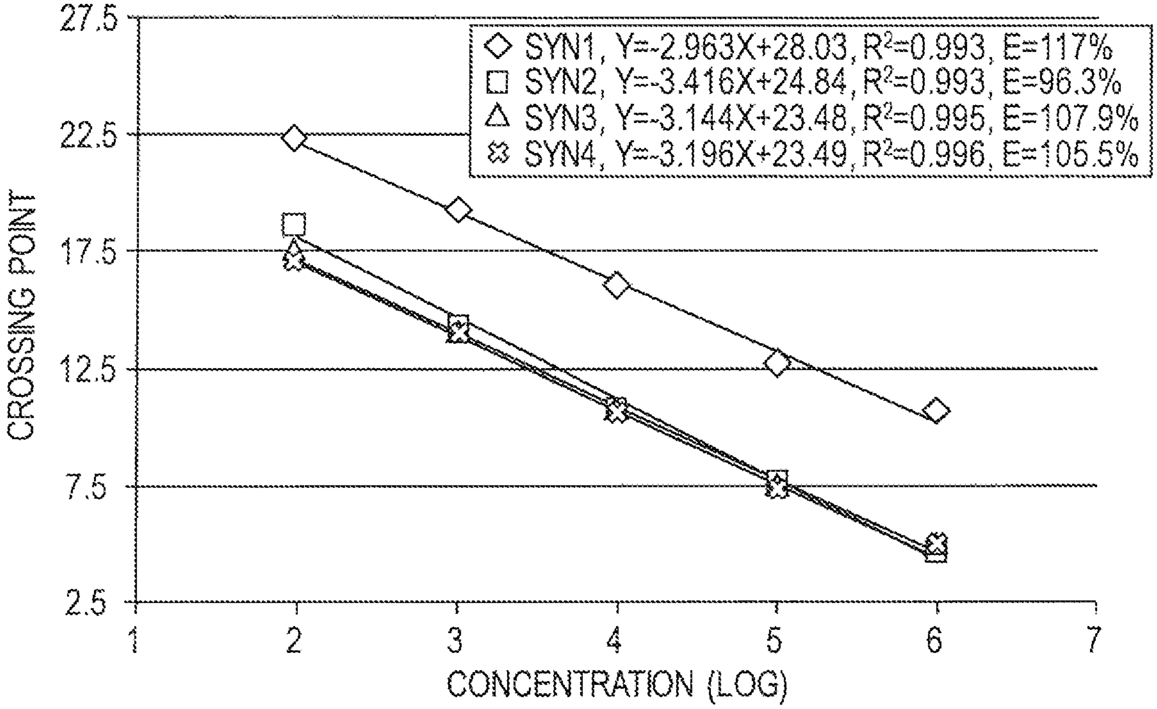
FIG. 5 shows the Cp across five dilutions of four different prospective synthetic quantification standards.

FIG. 5 shows Cp vs. concentration of four prospective internal quantification standards. In this illustrative embodiment, the internal quantification standards have synthetic sequences. In this illustrative example, for the second-stage inner reaction, the four quantification standards all share one common primer and each has one unique specific primer. They were also designed to share both outer primers for first-stage PCR. Thus, each of the second-stage wells used for detecting the quantification standards would be spotted with the common primer and the primer for that quantification standard, such that only one quantification standard should amplify in each such well. However, it is understood that this is an illustrative example only, and that other configurations are possible. Syn2, Syn3, and Syn4 each have similar amplification efficiencies and were chosen for additional study. Syn1 behaves differently and was omitted from further work. Thus, in one embodiment it is desirable to have multiple quantification standards that have similar amplification efficiencies.

In this illustrative example, amplification was detected using the dsDNA binding dye LCGreen Plus. However, this is illustrative only and other dsDNA binding dyes, probes, signals, or other ways of detecting amplification are within the scope of this invention.

It is understood that there are various ways of designing quantification standards that have similar amplification efficiencies. In one embodiment, the quantification standards have the same sequence between the inner primers and differ only in inner primer binding sequence. In another embodiment, the quantification standards are all of substantially the same length and substantially the same GC content. In yet another embodiment, the sequences are of differing lengths but also differ in GC content to compensate. Other ways of designing nucleic acids with similar amplification efficiencies are known in the art.

In one embodiment, illustratively when the quantification standards are used in a two-step nested multiplex PCR reaction, the quantification standards may all use the same outer primers in the first-stage PCR reaction, potentially even sharing identical regions surrounding primers to avoid differences due to the secondary structure formations. The quantification standards may then be distinguished by using different inner primers in the individual second-stage PCR reactions, either with each calibrator having a unique pair of inner primers, or, as above, sharing one inner primer and having one unique inner primer. Such an embodiment has advantages in that each of the quantification standards binds to its first-stage primers with the same kinetics, and the complexity of the first-stage multiplex PCR reaction may be minimized.

While reference is made to two-step PCR, the same principle can be used in a single-step multiplex PCR. In this case, the quantification standards may have different forward or reverse primers or the same forward and reverse primers and illustratively each has a specific fluorescent probe or other identifiable label, such as chemiluminescence, bioluminescence, radioluminescence, electroluminescence, electrochemiluminescence, mechanoluminescence, crystalloluminescence, thermoluminescence, sonoluminescence, phosphorescence and other forms of photoluminescence, enzymatic, radioactive, and the like are contemplated herein. The application is only limited by the number of detection channels available in any system or other methods for distinguishing the labels, as are known in the art. Some labels may require post-amplification processing. Further, it is understood that labeled quantification standards may be used in a two-step PCR wherein the same or different primer sequences may be used and the label is used to detect in the second-stage PCR. In such an embodiment, the labeled quantification standards optionally may be multiplexed in the second-stage PCR and distinguished by the label.

While synthetic quantification standards are used in this example, it is understood that the sequences used for quantification standards may be natural occurring. For example, if yeast is used as the SPC, yeast sequences may be used for one or more of the quantification standard sequences. For the fission yeast *Schizosaccharomyces pombe*, the Tf2-type retrotransposable element/transposon is present in 13 copies while the ribosomal RNA genes is repeated 47 times. In another example, gene sequences that exist in different copy numbers may be used. Illustratively, fungal pathogens have 50 to 200 copies of the ribosomal RNA gene per nuclear genome. These pathogens also have transposons that vary between five and 20 copies per genome. Bacterial pathogens have between 1 and 15 copies per genome but most have more than 5 copies. Other naturally occurring or synthetic templates may be used, such as bacteriophages for viruses and synthetic particles able to mimic membrane and/or capsid and/or envelope structures. Moreover, while three quantification standards are used in many of the examples herein, it is understood that only two quantification standards are needed to define a linear standard curve, and more quantification standards may be desired in embodiments where a wide range of target concentrations is expected or where a non-linear standard curve is expected. Illustratively, the number of quantification standards may be chosen based on the dynamic range of the system and the requirements of the assay.

Alternatively, as shown in Example 5, it is also possible to use only one quantification standard (see the sample processing control (SPC) discussed in Example 5) in each experimental run and to rely on an imported standard curve for the quantification previously generated with a quantification standard range, illustratively with at least 3 quantification standards (named QS in Example 5) which may be included in software for this analysis.

Example 3—Multiplex Calibration

Figure 6A:
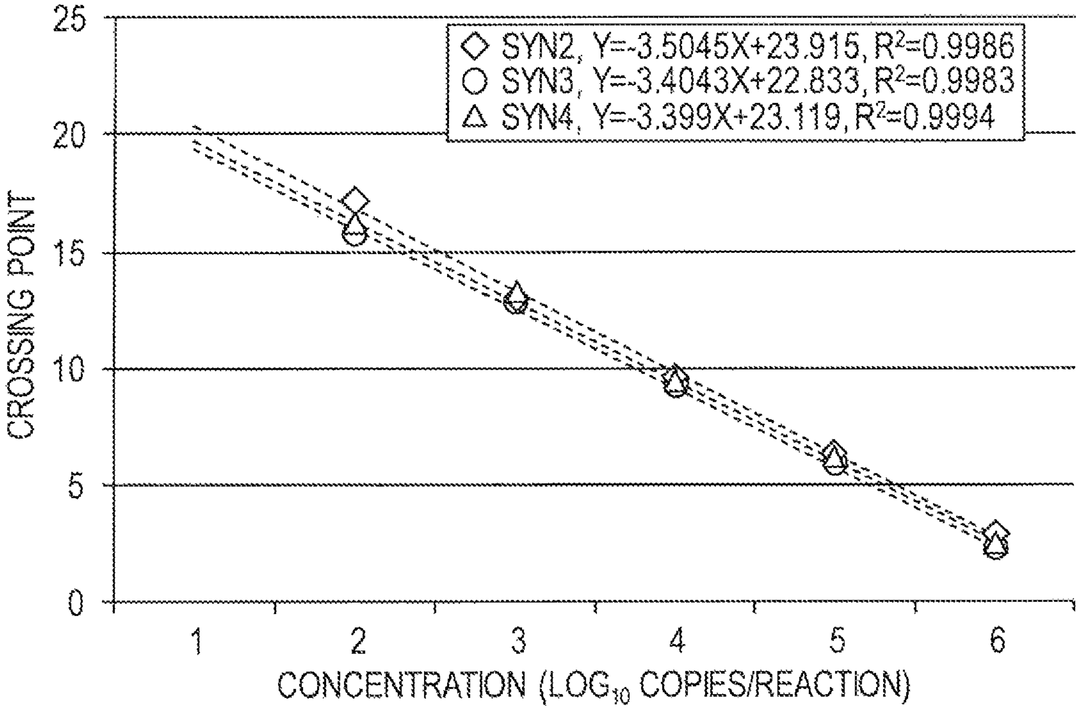
FIG. 6A is similar to FIG. 5, but showing data for only three of the quantification standards.
Figure 6B:
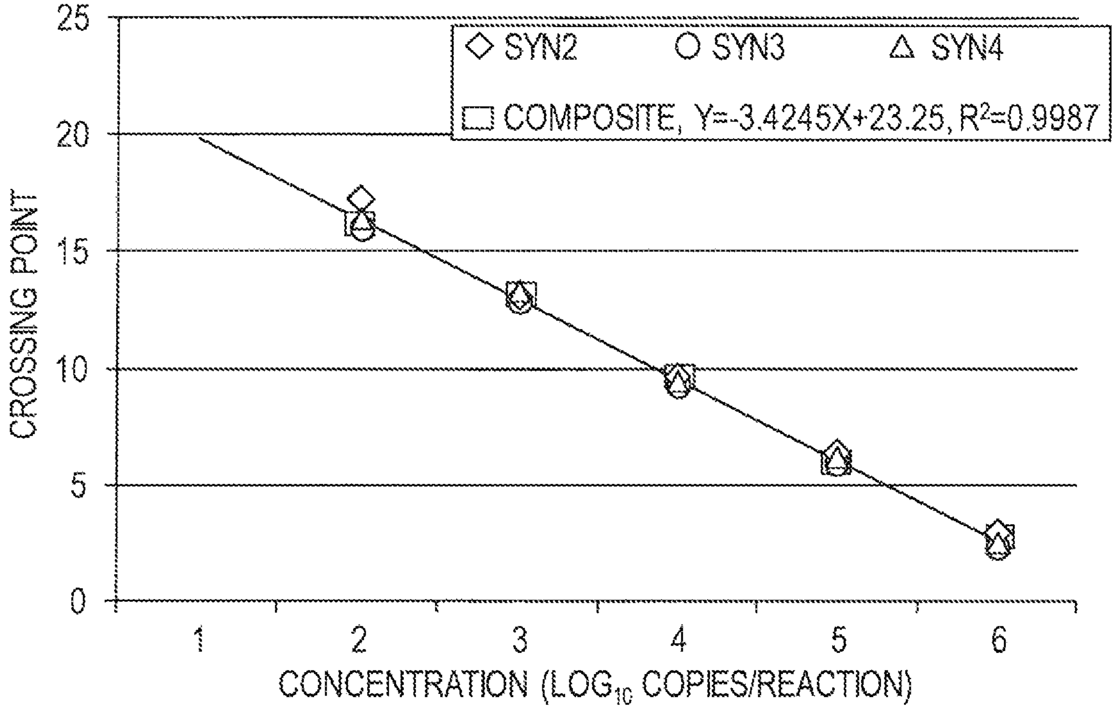
FIG. 6B shows a single curve using the data from all three of the quantification standards.

FIG. 6A is similar to FIG. 5, but showing data only from the three chosen calibrator sequences. FIG. 6A demonstrates the linearity and nearly identical amplification efficiencies for the three illustrative quantification standards. FIG. 6B shows a composite standard curve generated from the combination of three points each of the three quantification standards over a total of five dilutions.

Figure 7:
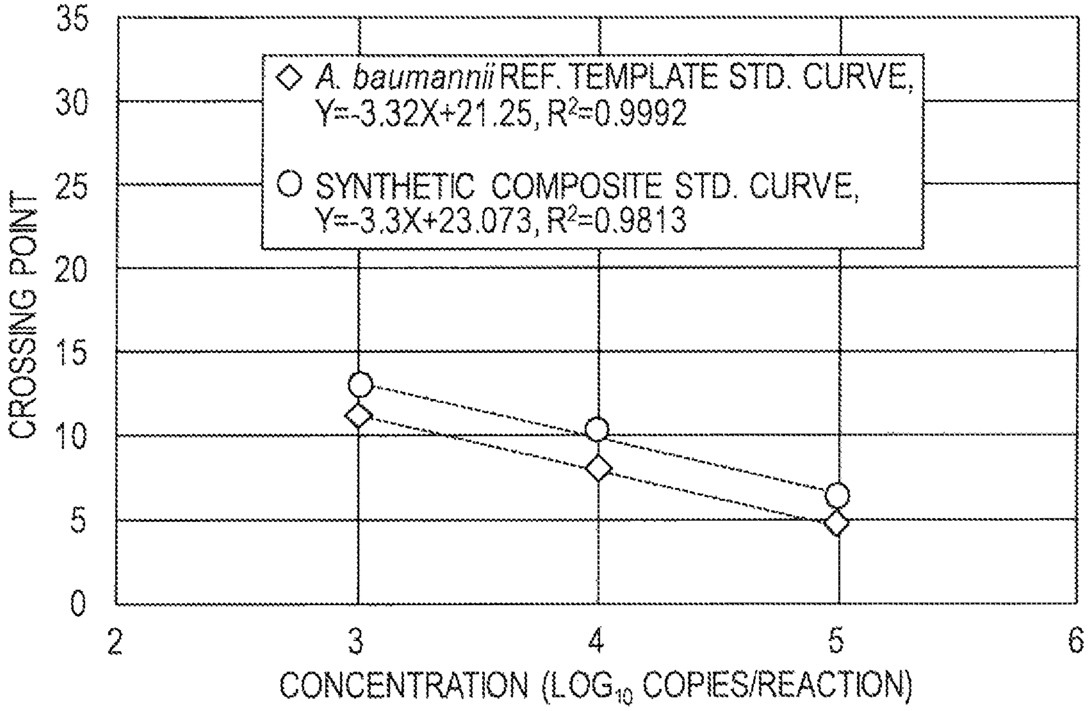
FIG. 7 shows a standard curve for *A. baumannii* plotted along with a curve generated from the three quantification standards. The x-axis is the amount of *A. baumannii* or quantification standards included in the reaction, and the y-axis is the Cp.

Now that the illustrative calibration plot has been generated, a standard curve using assay-specific reference templates for each target assay may be generated. FIG. 7 compares the externally generated standard curve using a well-quantified synthetic reference template for *Acinetobacter baumannii* with a composite internal standard curve generated using the quantification standards. Here the three "Syn" templates were pre-mixed before addition to the reaction tube; Syn4 was added at $10^3$ copies, Syn2 was added at $10^4$ copies, and Syn3 was added at $10^5$ copies per reaction. The Cp values from these templates were used to generate a composite internal standard curve for each reaction. An external standard curve was generated using a synthetic reference template *A. baumannii* reference template, also tested at the same concentrations as the "Syn" templates. The composite internal standard curve and the *A. baumannii* standard curves are very similar. The similar slope shows that the efficiencies are similar. It is expected that an unknown starting concentration of an *A. baumannii* sample can be predicted using the internal standard curve. However, because the y-intercept is shifted between the two curves, quantification of *A. baumannii* may benefit from a correction factor when using this internal standard curve.

Thus, the concentration of target organisms can be computed using the composite internal standard curve. Note that the internal standards are each at different known concentrations and are amplified in the same process as the target organisms. The methods illustratively employ cycle threshold (Ct) values (or alternatively a Cp value or other similar methods), which is the number of cycles of PCR required to obtain a fluorescence signal above the background fluorescence, for the target and internal standard, as determined experimentally. Other points may be used as well, such as using a first, second, or nth order derivative, illustratively as taught in U.S. Pat. No. 6,303,305, herein incorporated by reference in its entirety. Other points may be used as well, as are known in the art, and any such point may be substituted for Cp or Ct in any of the methods discussed herein. Illustratively, in a two-step multiplex system, the Cp value is determined in the nested second-stage reactions. However, in other embodiments, it is understood that the Cp may be determined as is appropriate for the amplification system. For example Cp may be determined in a single multiplex reaction or in a subsequent second-stage reaction by using oligonucleotide probes, each of which are specific for a quantification standard sequence and have a distinguishable fluorescent signal.

In an illustrative example where a single internal standard is used, the concentration of the target organism may be computed using the Cp of the target organism ($Cp_t$), the concentration and Cp of the internal standard ($Concentration_s$, $Cp_s$), and the target organism's efficiency ($Efficiency_t$) according to the following formula.

$$\text{Concentration}_t = \text{Concentration}_s * \text{Efficiency}_t^{(Cp_s - Cp_t)}, \quad \text{[Equation 1]}$$

where the subscripts s and t represent the internal quantification standard and target organism, respectively, and $$Efficiency_t = 1 + \frac{\text{Efficiency as a percent}}{100}. \quad \text{[Equation 2]}$$

For example, the Efficiency variable for a target with 100% amplification each PCR cycle would equal 2. Note that the Efficiency is assumed to be predetermined and constant across a dynamic range. As discussed above, the efficiencies of the internal calibrators should all be similar, illustratively within 1%, within 2%, within 5%, or within 10% of each other. Similarly, the efficiencies of the targets should each be similar to that of the calibrators, illustratively within 2%, within 5%, within 10% or within 12% of the calibrators. It is understood that for precise quantification, efficiencies within a narrower range, illustratively within 1%, within 2%, or within 5% is desirable. However, for semi-quantitative or "binning" results (see below), a larger variation in efficiencies may be tolerated.

When two or more quantification standards are used, a standard quantification curve may be generated, illustratively using a least-squares regression line fit to the (Cp, $\log_{10}$(Concentration)) data for the internal quantification standards, as illustrated in FIGS. 6A-6B. Illustratively, the regression fit is of the form:

$$\log_{10}(\text{Concentration}) = (Cp - b)/a \quad \text{[Equation 3]},$$

where b is the intercept and represents the value of Cp when $\log_{10}$(Concentration) is zero, and a is the slope which represents the degree to which Cp changes with a single unit change in template concentration (a function of efficiency). Given a computed Cp value for an unknown target, this formula gives the target concentration in $\text{Log}_{10}$ units. Other algorithms or equations may be applied, as needed, to improve the precision and accuracy of quantification. These may include adjustments required for platform-specific, matrix-specific, or assay-specific biases in extraction and/or amplification. These may also include algorithms that can account for differences in assay efficiencies in the separate steps of any multi-step amplification process. In some embodiments, the quantification standard curve may be non-linear, or may be linear only within a certain dynamic range. Illustratively, if there is a concentration-dependent variable slope, a sigmoidal dose-response curve may be used. Other non-linear curves are within the scope of this invention.

The method described above can be used for a target organism with an unknown concentration based on observed Cp values for the target and the regression equation for the standard curve generated using internal quantification standards. Ideally, all targets that are being quantified using this approach should have assays that have equivalent or similar PCR efficiencies as the internal quantification standards assays. However, there may be some variations in the slopes or intercepts of target assays standards curves. Given that target assays may have different amplification characteristics from the internal standards, assay specific correction factors can be used to adjust for systematic assay-specific bias to improve the accuracy of computed concentration of the unknown target. Illustratively, when a linear quantification curve is used, a may be corrected with a correction factor indicative of a different assay-specific efficiency (which changes the slope) or b may be corrected due to lack of optimal PCR conditions for a specific target that causes the target Cp to be delayed. Both corrections may be used where appropriate. In another example, illustratively when nested PCR is used, differences in b observed in PCR2 may be result of total outcome of the PCR1 assays, due to variations in the PCR1 efficiencies. In this case, the correction factor might be calculated as a function of the Cp values or be a constant depending on the desired quantification accuracy.

For example, a set of controlled experiments may be run with a known target organism concentration. If multiple replicates at a single concentration are used, then the assay specific correction factor may be computed as the average difference of the known concentration and the computed concentrations in $\text{Log}_{10}$ units. Illustratively, to obtain the corrected log concentration of the target organism, the assay specific correction factor may be added to the log concentration of the target organism (as computed above by the internal quantification standards method). Each target sequence in the multiplex assay illustratively will have its own correction (or no correction at all, if very similar to the composite standard curve).

Figure 8A:
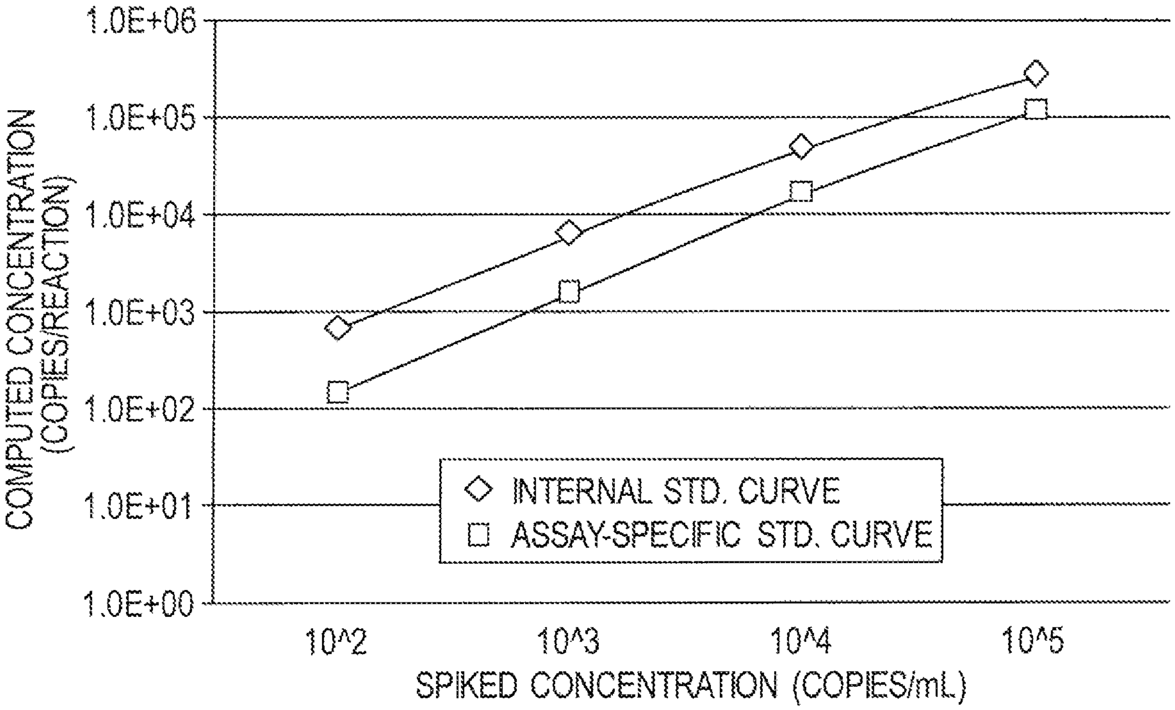
FIG. 8A shows the composite standard curve from quantification standards and the external standard curve specific for *A. baumannii*, without correction.
Figure 8B:
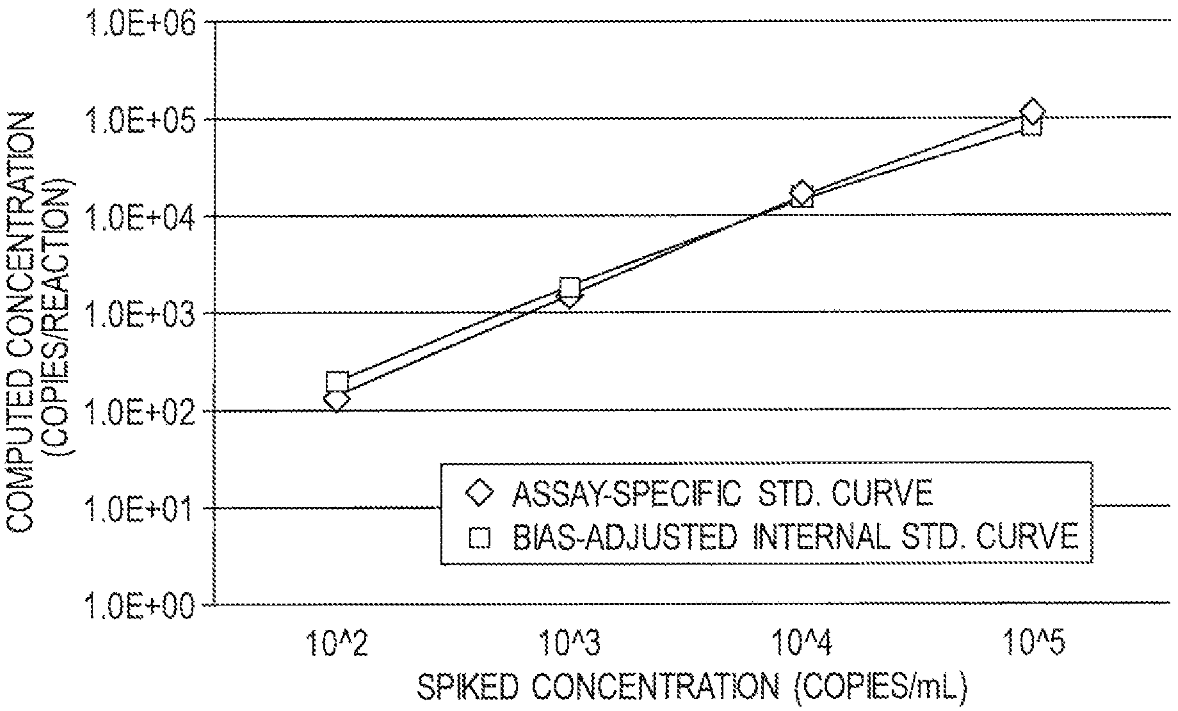
FIG. 8B shows the same data as FIG. 8A, with an assay-specific correction factor.

An experiment was set-up to compare quantification of a target organism computed by assay-specific standard curve to that computed by the composite internal standard curve. In this experiment, 10-fold serial dilutions of known quantities of *A. baumannii* genomic nucleic acid were multiplexed with internal quantification standards in bench-top reactions. An external assay-specific standard curve was also set-up as described above in reference to in FIG. 7. FIG. 8A shows the results of using the composite standard curve from quantification standards and the external standard curve specific for *A. baumannii*. If the composite standard curve is used without correction, there is an apparent systematic over-quantification (~0.5 log copy units) of the target organism (*A. baumannii*), whereas when the 0.5 log copy units correction is applied, the corrected assay-specific standard curve gives a fairly accurate estimate of the *A. baumannii* titer in the sample. FIG. 8B shows how this systematic bias in quantification can be corrected by applying an average assay-specific correction factor, generated as described above, to quantities computed by the internal standard curve method. Similar corrections may be made for each assay in the multiplex reaction.

In many embodiments, absolute quantification is not necessary, and semi-quantitative results may be sufficient. Results may be reported as absolute concentrations (with or without system error (illustratively 95% prediction interval)), or may be binned into one of a plurality of ranges, illustratively reporting a "high", "medium", or "low" concentration, each covering one or more orders of magnitude. It is understood that the number of bins may vary, as is appropriate with a specific assay, and any number of bins may be used. Also, the range of binning (orders of magnitude or other measures) for semi-quantitative results may be adjusted, as is appropriate for the specific example.

Example 4—Methods for Normalizing and Quantifying Sequencing Data

In addition to or in lieu of the assay methods and systems described in Examples 1-3, a Next-Generation Sequencing (NGS) method. NGS may, for example, be used for to detection, identification, and quantification of potentially pathogenic organisms in a sample. In another example, NGS may be used as a so-called 'comparator' to confirm the performance of another assay, such as one of the assay methods and systems described in Examples 1-3. In a specific example, NGS includes PCR followed by Next-Generation Sequencing.

Modern sequencing instruments (e.g., NGS instruments) can generate a large amount of data that can be computationally taxing to analyze. In addition, the sequencing process (e.g., sample type, sample preparation, amplification, and sequencing) and the data obtained may include a number of confounding factors that can make the data difficult to analyze and/or to compare data from experiment to experiment, lab to lab, etc. For instance, samples may not be uniformly prepared for sequencing due to human (i.e., random) and systematic errors. In another instance, samples may not be uniformly sequenced due to the presence of nucleic acids or multiple length ranges from multiple organisms at a variety of concentrations. For example, sputum is a particularly rich sample type that can have organism loads ranging from approximately 0-$10^{13}$ organisms/ml of sample, with approximately $10^3$-$10^9$ organisms/ml being fairly typical. Other clinical samples like feces or blood culture media may have similar organism loads. Likewise, clinical samples can include large amounts of host DNA (e.g., human DNA). In addition, sequencing libraries from multiple samples may be pooled together prior to sequencing, which shortens the time needed for sequencing because multiple samples are analyzed simultaneously, but it can dramatically increase the amount of data that is collected in a single sequencing run. In addition, individual samples in a pool of samples may not be prepared uniformly due to the factors described above. Data from individual pooled samples is typically separated in the data set for individual alignment and analysis.

To address these and other similar issues, it was discovered that a known quantity of a reference DNA sequence, referred to herein as quantification standard material (QSM) or an internal quantification standard, could be added to samples intended for sequencing prior to sample preparation (e.g., prior to nucleic acid extraction and amplification) and before sequencing; the internal quantification standard is then carried through all sample processing and sequencing steps. Because the internal quantification standard is added at the beginning of sample processing, the number of sequencing reads for the standard sequenced (i.e., the number of molecules of the standard sequenced) accurately reflects all of the manipulations and systematic losses that the sample can undergo through steps such as, but not limited to, sample preparation, amplification, nucleic acid recovery, purification, and sequencing. Likewise, because an internal quantification standard is added separately to each sample prior to extraction, library preparation and pooling, the standard added to each sample can accurately reflect all of the processing steps that each sample is subjected to. In one embodiment, the internal quantification standard added separately to each sample in a pool of samples is the same. In one embodiment, each amplified sequence in a pool has its own sample-specific identification sequence (e.g., a DNA barcode) that allows the nucleic acids from each sample to be tracked, separated, and normalized by sample.

The internal quantification standard (i.e., the reference DNA sequence) can be essentially any natural or synthetic nucleic acid sequence provided that it is distinguishable from the other nucleic acids in the sample that may be sequenced. For instance, the internal quantification standard may be a naturally occurring or engineered plasmid, a naturally occurring or synthesized linear DNA fragment, or the like. Since the efficiency of sample preparation, DNA amplification, purification, and sequencing are all affected by the size of the DNA, the internal quantification standard should be in the approximate size range as the unknown sequences in the sample. For instances, if the fragments of the DNA to be sequenced have a size in a range of 200-500 base pairs, then the internal quantification standard should also have a size in a range of 200-500 base pairs. In addition, the composition (e.g., relative G-C content) of the internal quantification standard should also be relatively similar to the composition of the DNAs to be sequenced.

In one embodiment, a known quantity of the internal quantification standard may be added to the sample to be sequenced. If multiple samples are to be sequenced, the internal quantification standard may be separately added to each sample. In one embodiment, the known quantity of the internal quantification standard is determined based on the assay. For instance, the quantity of the internal quantification standard sufficient for the assay may depend on factors such as, but not limited to, the desired resolution of the assay, the nucleic acid extraction efficiency, the concentration range of the nucleic acids to be sequenced, the prevalence of genetic mutations to be detected, or the desired sequencing read depth. In one embodiment, known quantity of the internal quantification standard may be added in an amount within the linear range of the assay that is, for example, above the lower limit of detection (LOD) and below the maximum concentration expected for the assay. For instance, in the specific examples discussed herein, the linear range of DNA copies/ml that can be sequenced and distinguished in the sequencing assay is about $10^2$ to about $10^7$-$10^8$ copies/ml and, in this instance, the internal quantification standard may be added in an amount of about $10^4$-$10^6$ copies/ml. As will be explained in greater detail below, the amount of the internal quantification standard added and the sequencing read depth are related to the LOD of the assay.

To sequence the nucleic acids in the samples, RNA or DNA is extracted from sample tissue/cells and fragmented. RNA is converted to cDNA by reverse transcription. Preparing the sample including the internal quantification standard for sequencing includes the generation of DNA fragments, which are converted into a 'library' by annealing or ligation to sequencing adapters that include specific sequences designed to interact with the sequencing platform and sample-specific identification sequences (e.g., DNA 'barcodes') that can be used to identify the sequencing data originating from the specific sample. If two or more samples are to be pooled and sequenced in parallel, each sample has its own sample-specific identification sequence or 'barcode' that can be used to separate the data originating from each sample. This procedure is primarily compatible with Illumina sequencing technology. However, it should be noted that almost all of the principles discussed herein can be applied with minimal modification to NGS platforms developed by Life Technologies, Roche, Pacific Biosciences, and others.

The next step involves sequencing the DNAs. The precise method of sequencing is dependent on the sequencing platform, but all modern massively parallel sequencing technologies are somewhat similar and generate similar data.

Following sequencing, reads originating from the internal quantification standard are then counted in each sample, and each sample's NGS data set may be normalized. As an initial check, a linear relationship should exist between the quantity of the internal quantification standard added to the sample and the number of sequencing reads observed for the internal quantification standard. In addition, a minimum number of internal quantification standard sequencing reads ('F') should be recorded. The normalization (1) applies data acceptance/rejection criteria to the sequencing data set based on the presence of a minimum number of sequencing reads for the internal quantification standard for the sample and (2) ensures that substantially the same limit of detection (LOD) is applied to all unknown nucleic acids in the sequencing assay. If samples are pooled, the normalization ensures that all samples are read to a sufficient depth, that all samples retain the same number of QSM read pairs, and ensures that substantially the same limit of detection (LOD) is applied to all unknown nucleic acids in all samples in the sequencing assay.

Assuming that the linear relationship exists and that 'F' internal quantification standard/QSM reads are recorded, the sequencing data may be processed to retain a normalized number of sequencing reads according to Equation 4:

$$\text{NORM}=\text{No. of Sequencing Reads}*(F/\text{Observed No. of Sequencing Reads Originating from the Internal Quantification Standard}) \quad \text{[Equation 4]}$$

'F' is a fixed, user-set minimum expected number of the internal quantification standard sequencing reads that is specific to the assay. For instance, 'F' is a sequencing read number value set to ensure a sequencing read depth sufficient in order to detect nucleic acids at or near the limit of detection (LOD) of the sequencing assay.

NORM may represent a subset of the sequencing data and is the number of sequencing reads that are saved for further analysis and quantification. As can be seen from Equation 4, if 'F' and the Observed No. of Sequencing Reads Originating from the Internal Quantification Standard are the same, then the quantity in the parentheses reduced to '1' and NORM then equals the number of sequencing reads recorded. On the other hand, if the number of internal quantification standard sequencing reads in the data set is greater than 'F', then the quantity in the parentheses is <1 and the NORM equation downscales the data to account for the over reading and to ensure that the same LOD is applied across all samples. If the number of internal quantification standard sequencing reads in the data set is less than 'F', then the data from that sample may be rejected and the sample may be submitted for further sequencing until 'F' internal quantification standards reads are recorded.

The number 'F' of QSM reads to retain is a parameter selected during assay development and is related to read depth and to the limit of detection (LOD) of the assay. This effect is illustrated in Table 1 below.

TABLE 1

| Analyte X concentration | Expected Number of X Reads when QSM added to Sample at 5 × $10^5$ copies/ml | | |
|---|---|---|---|
| in the Sample | 'F' = 500 | 'F' = 5000 | 'F' = 50000 |
| $10^9$ copies/ml | 1000000 | 10000000 | 100000000 |
| $10^8$ copies/ml | 100000 | 1000000 | 10000000 |
| $10^7$ copies/ml | 10000 | 100000 | 1000000 |
| $10^6$ copies/ml | 1000 | 10000 | 100000 |
| 5 × $10^5$ copies/ml | 500 | 5000 | 50000 |
| $10^5$ copies/ml | 100 | 1000 | 10000 |
| $10^4$ copies/ml | 10 | 100 | 1000 |
| $10^3$ copies/ml | 1 | 10 | 100 |
| $10^2$ copies/ml | <1 | 1 | 10 |
| $10^1$ copies/ml | <1 | <1 | 1 |
| 1 copy/ml | <1 | <1 | <1 |

For example, if the internal quantification standard is added to the sample at a concentration of 5×$10^5$ copies/ml, then different numbers of QSM reads need to be recorded in order to ensure that all unknown nucleic acids at or above the LOD are sufficiently sequenced and detected. This is referred to as the sequencing read depth. For instance, if the internal quantification standard/QSM is added to the sample at 5×$10^5$ copies/ml and 'F' is 500, then the LOD for the assay for the detection of an unknown nucleic acid will be not less than $10^3$ copies/ml (typically, in the range of $10^3$-$10^4$ copies/nil); if 'F is 5000, then the LOD of the assay will be not less than $10^2$ copies/ml (typically, in the range of $10^2$-$10^3$ copies/ml); or if 'F is 50,000, then the LOD of the assay will be not less than 10 copies/ml (typically, in the range of 10-$10^2$ copies/nil). So it can be seen that the LOD of the assay can be lowered by increasing the read depth of the assay (i.e., increasing 'F'). However, it does not make sense to set 'F' arbitrarily high because the sequencing burden also increases. For instance, if the LOD of the assay is not less than 10 copies/ml ('F'=50,000) and the most prevalent species is present at $10^9$ copies/ml, which is not uncommon, then the most prevalent target that entered at $10^9$ copies/ml will be sequenced 100 million times in order to achieve just 1-10 (e.g., 4) reads of a target present in a range of $10^1$ to $10^2$ copies/ml. This may not be practical.

In the examples described herein, 'F' is typically set at 5000 QSM reads because this is sufficient to reproducibly ensure detection of nucleic acids present in a range of $10^3$-$10^7$ copies/ml or greater. For more or less stringent assays, ‘F’ may be set differently. Thus, in one embodiment, sequencing read depth (i.e., ‘F’) may be as low as 100-1000 QSM reads, or in a range of about 1000 internal quantification standard sequencing reads to about 100,000 internal quantification standard sequencing reads, preferably about 2000 internal quantification standard sequencing reads to about 75,000 internal quantification standard sequencing reads, more preferably about 5000 internal quantification standard sequencing reads to about 50,000 internal quantification standard sequencing reads, or most preferably at least 5000 internal quantification standard sequencing reads.

Figure 9:
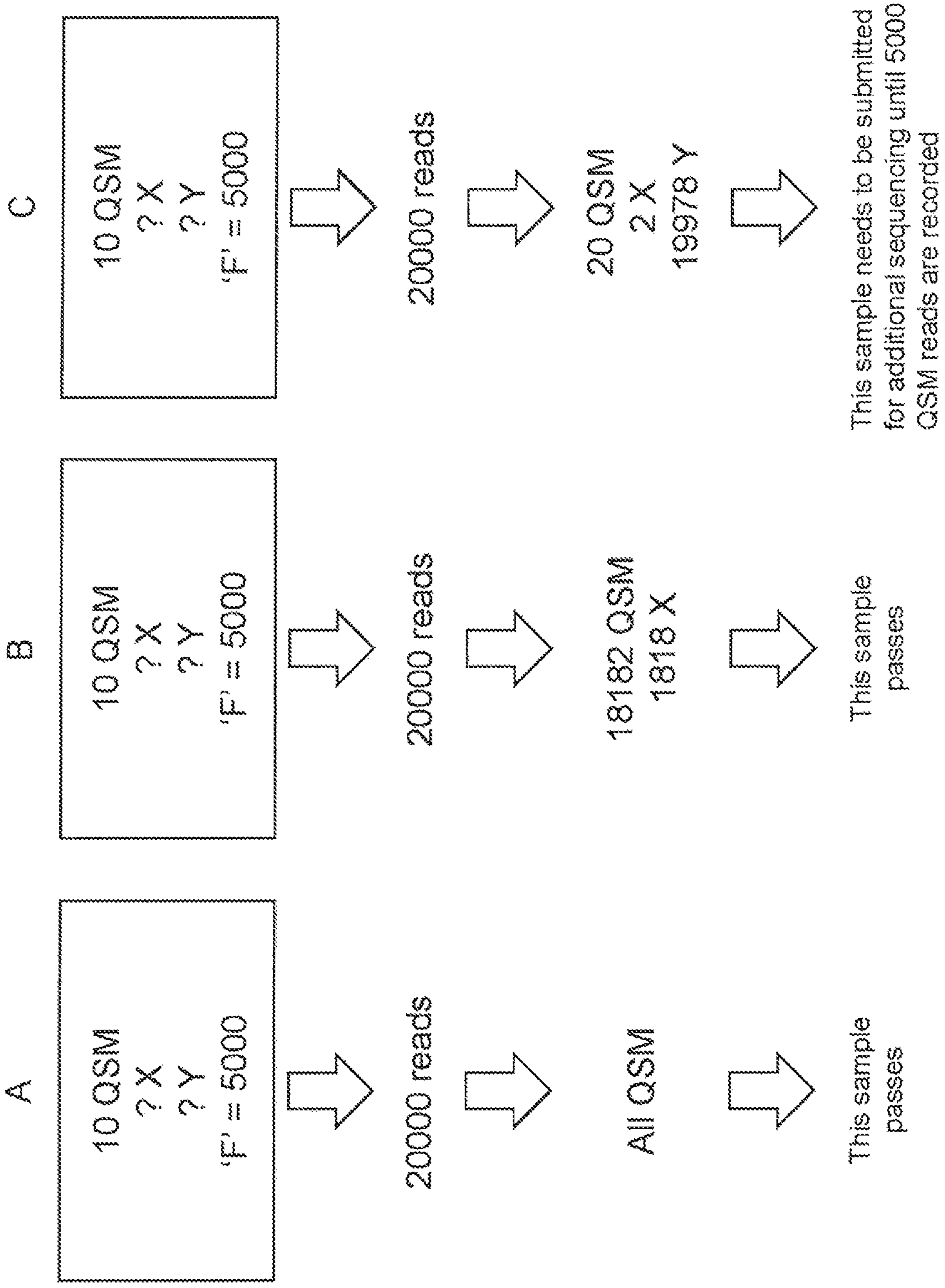
FIG. 9 illustrates a hypothetical sequencing data set for three samples A, B, and C.

The power of the internal standard and the value of ‘F’ is further illustrated in reference to FIG. 9. FIG. 9 illustrates a hypothetical case of a sequencing data set for three samples, A, B, and C. Each sample was spiked with 10 QSM copies and each sample contained unknown amounts of nucleic acids X and Y. In each sample, 20,000 sequencing reads were collected. In sample A, the sample apparently contained no X or Y and all 20,000 reads were attributed to the QSM. Of the 20,000 reads in sample B, 18182 were attributed to QSM and 1818 were attributed to X and no reads were attributed to Y. Sample C illustrates a different case. Of the 20,000 reads in sample C, 20 were attributed to QSM, 2 were attributed to X, and 19978 were attributed to Y. From the initial read attribution, it can be seen that sample C has a very high concentration of Y and relatively little X. Nevertheless, sample C has fewer than 5000 QSM reads, so the sample must be submitted for additional sequencing until at least 5000 QSM reads are recorded. However, in the case of sample C, that does mean that Y will be sequenced almost 5 million times in order to achieve minimum QSM coverage. This may seem burdensome compared to the industry standard, which may set a minimum total read value for each sample (e.g., 20,000 reads or 200,000 reads or 2 million reads) and then assume that all detectable nucleic acids are sequenced if this total is achieved, but the methods described herein ensure that the same read depth is achieved across all three samples A, B, and C and ensure that the sequencing has an equal chance of detecting a rare nucleic acid in each sample. In the case of sample C, the sample would still be ‘under read’ even if 2 million total reads were recorded, which seems like it should be a sufficient number, but, in this case, 2 million reads would still yield an insufficient number of QSM reads and the sample would be under read for the LOD of the assay. However, when sequencing actual clinical specimens with unknown amounts of nucleic acids, it may not be possible to know at what point sufficient read depth is achieved without an internal quantification standard. That is, the unknown nucleic acids in a sample (e.g., X and Y in sample C) are not given an equal chance to be detected at the LOD until the QSM read is sufficient. Also, with 2 million or even 200,000 reads, it should be possible to detect X and Y, but without QSM, it may not be possible to quantify X and Y, and it may not be possible to determine when sufficient read depth is achieved to detect all rare nucleic acids in the sample. In samples A and B, more than 5000 reads were attributed to QSM, so the ‘F’ requirement is met, and samples A and B pass. Thus, it can be seen from the foregoing hypothetical cases that the internal quantification standard discussed herein is a powerful tool.

Returning further to FIG. 9, ‘F’ is a fixed, assay-set minimum expected number of the internal quantification standard sequencing reads and NORM [Equation 4] may yield a subset of the sequencing reads that are saved for further analysis and quantification. If ‘F’ and the Observed No. of Sequencing Reads Originating from the Internal Quantification Standard are the same, then NORM equals the number of sequencing reads recorded. In contrast, if the samples are ‘over read’ (as in samples A and B of FIG. 9), then NORM downscales the data to to account for the over reading and to ensure that the same LOD is applied across all samples. For instance, in sample A there were 20,000 reads attributed to the QSM; this sample is ‘over read’ for QSM and NORM=20,000*(5000/20,000)=5000. I.e., only one quarter of the data in sample A would be saved for further analysis. Similarly, in sample B, NORM=20,000*(5000/18182)=5500. Sample C is ‘under read’ for QSM, so it is not normalized or further analyzed and is instead submitted for additional sequencing.

Figure 10:
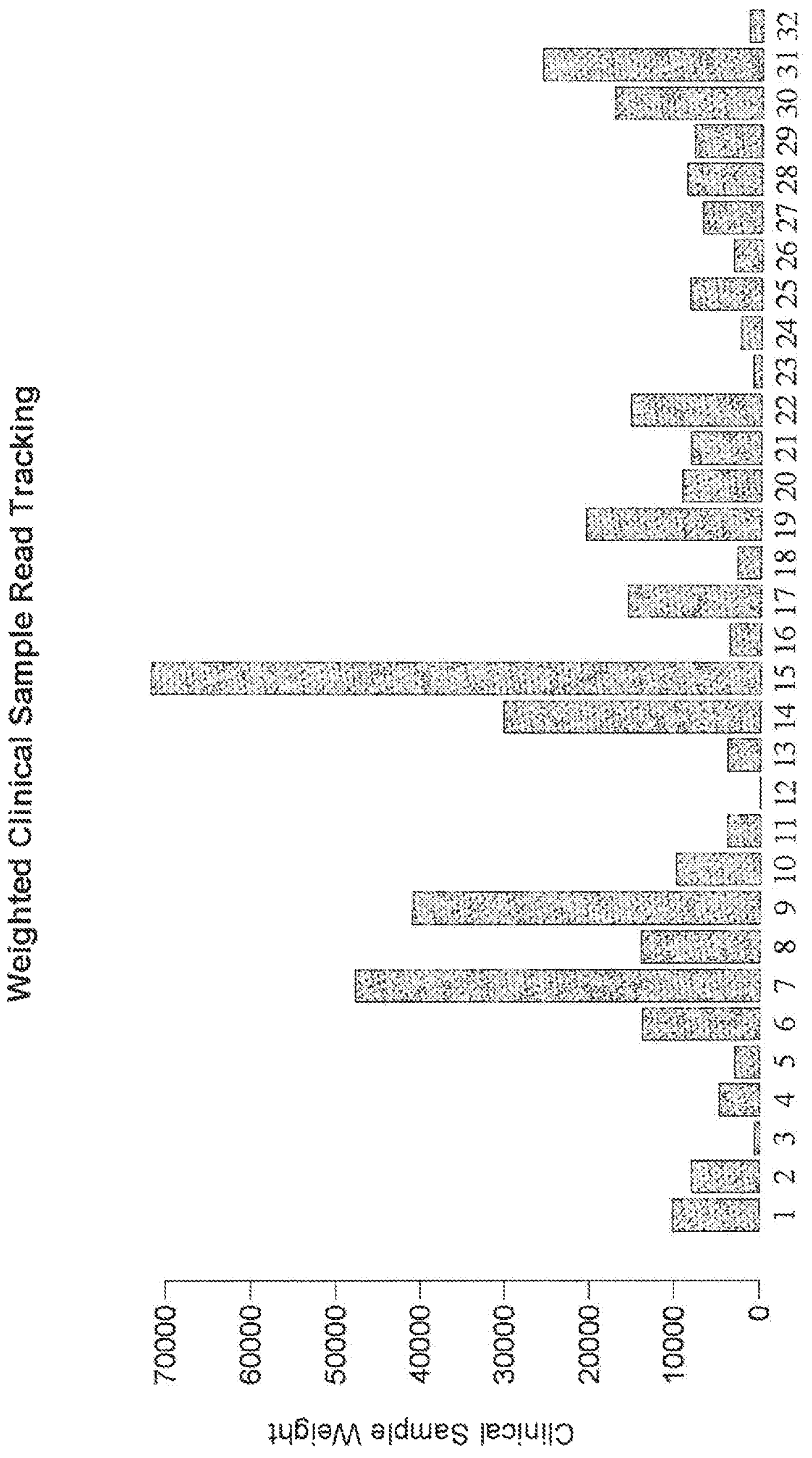
FIG. 10 shows raw sequencing counts for a pooled set of samples.
Figure 11:
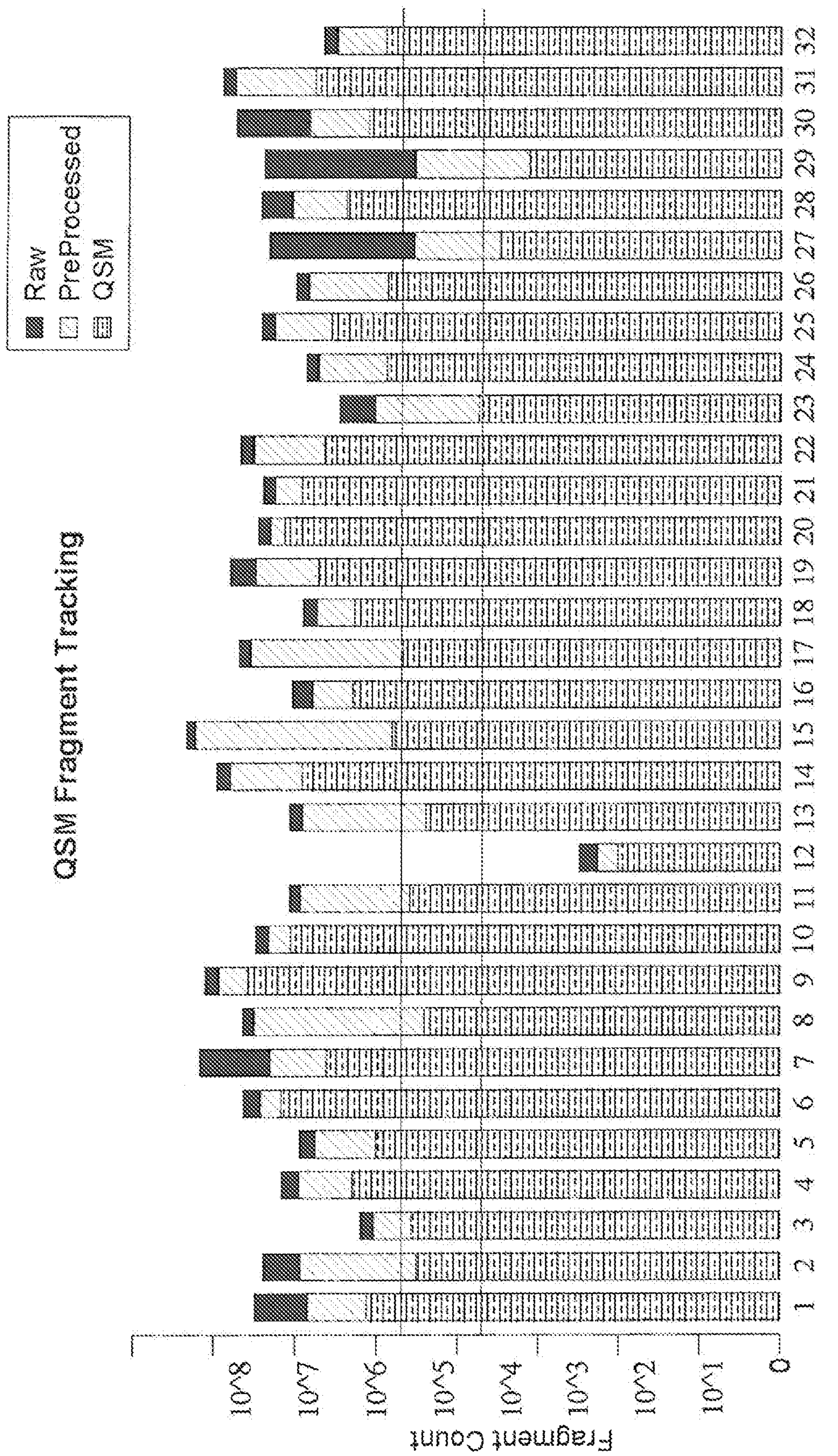
FIG. 11 shows internal quantification standard (also referred to herein as QSM) fragment count per sample in the pooled set of samples of FIG. 10.

Referring now to FIGS. 10 and 11, raw read numbers and QSM reads for a set of clinical samples are illustrated. The samples illustrated in FIGS. 10 and 11 are samples that were pooled for sequencing after being spiked with QSM; analysis then proceeded with sequencing library preparation and sequencing data collection. FIGS. 10 and 11 illustrate 32 samples that were pooled for sequencing. Each sample is spiked with its own QSM and each sample has its own unique tracking sequence (e.g., a DNA barcode) that is annealed, ligated or otherwise associated during sample preparation with all of the unknown nucleic acids in the sample and with each sample's QSM. These unique tracking sequences are associated with all nucleic acids in each different sample and are carried through all steps of sample preparation and sequencing, and the unique tracking sequences allow the data origination from the nucleic acids in each sample to be separated from the pooled sequencing data set for data analysis. While 32 samples are pooled and sequenced together in the examples illustrated in FIGS. 10 and 11, more or fewer samples could be pooled in practice. For example, 1000 or more samples may be pooled for one sequencing run assuming that there is sufficient distinguishing power of the barcodes and sufficient read depth for all of the samples. In one embodiment, 2-1000 samples may by pooled after preparing the samples and before the sequencing, preferably 2-500 samples may by pooled after preparing the samples and before the sequencing, more preferably 2-100 samples may by pooled after preparing the samples and before the sequencing, more preferably 2-50 samples may by pooled after preparing the samples and before the sequencing, or most preferably 2-32 samples may by pooled after preparing the samples and before the sequencing.

In FIGS. 10 and 11, the 32 samples were pooled and sequenced simultaneously. The QSM that was added to each sample and the unique tracking sequence associated with each sample allows the sequences originating from each individual sample to be segregated and analyzed separately. In FIG. 10 it is interesting to note the wide range of sequencing reads associated with each sample. For instance, sample 15 accounts for over ⅓ of all of the sequencing reads in the data set, while some samples (e.g., sample 13) have less than one tenth of the reads of sample 15. FIG. 11 shows the QSM reads. Three samples, 12, 27, and 29, had fewer than 5000 QSM reads and failed the initial QSM check. Sample 23 had barely enough QSM reads to pass, while samples like 6, 9, 10, and 14 were substantially over read for QSM. Interestingly, even though sample 15 had significant raw read numbers, its QSM read level was not unusually high. Nevertheless, because of the normalization described herein, all samples that pass are given equal weight. That is, a sample like 23 with only 5000 QSM reads is not significantly trimmed in the normalization process, but data from samples like 6, 9, 10, and 14 may be trimmed because the abundance of QSM reads in those samples indicates that the data from these samples is significantly overrepresented in the data set. Thus, it can be seen that the normalization process described here ensures that all samples are given equal weight and that the same LOD is applied to all samples.

In one embodiment, the unknown nucleic acid reads and the internal quantification standard reads may be each separately normalized by the same ratio ALPHA according to Equation 5:

ALPHA=*F*/Observed No. of Sequencing Reads Originating from the Internal Quantification Standard [Equation 5]

Figure 12:
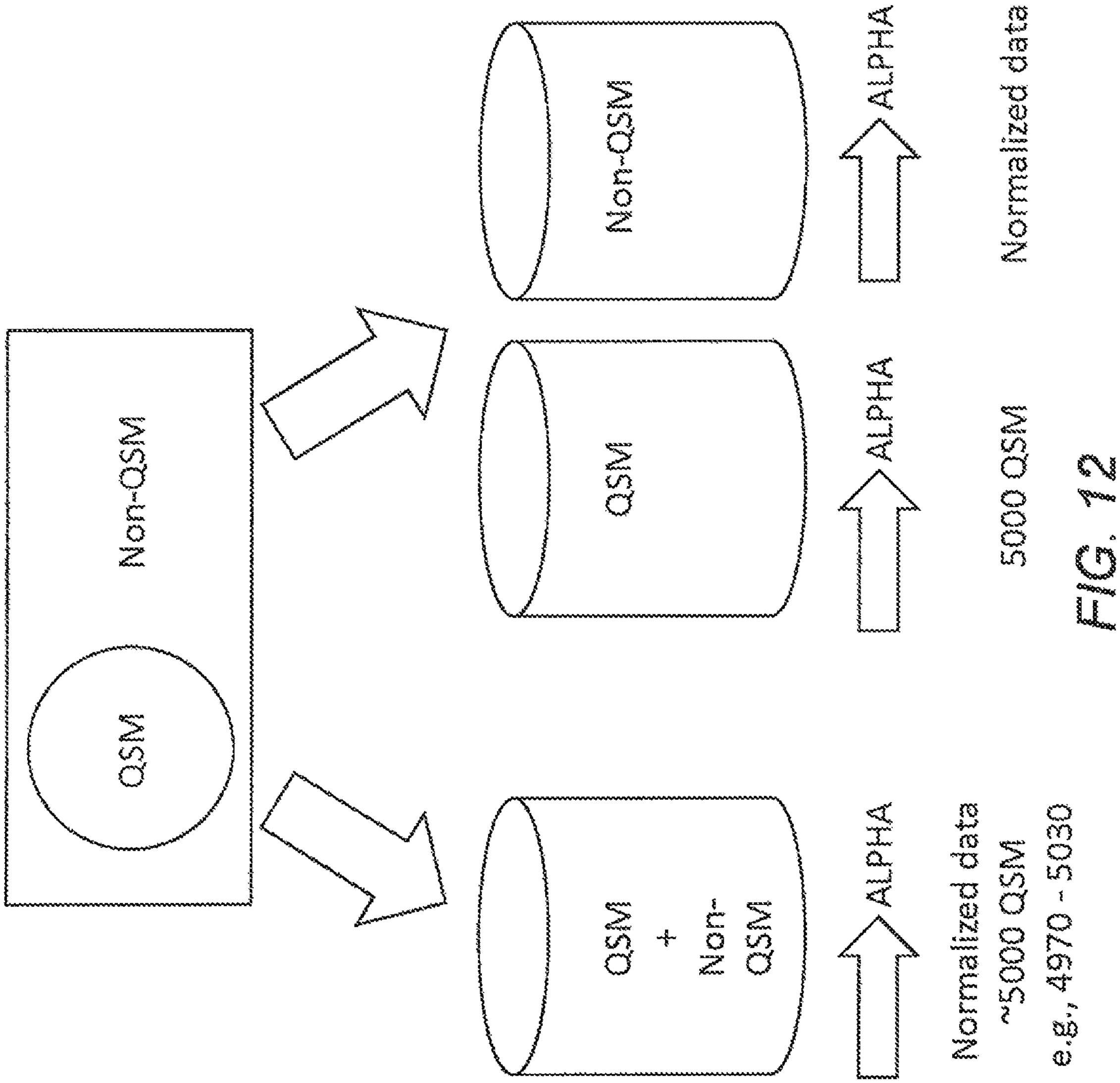
FIG. 12 illustrates two alternative methods for binning and normalizing a sequencing data set.

This is pictorially illustrated in FIG. 12. Data for a sample includes QSM reads and non-QSM reads. When these are normalized together (and down read together), the final number of QSM reads in the normalized data set may not be exactly (e.g., 5000)—instead there may be, for example, ~4970-5030 QSM reads in the binned data set. This is because the sampling process used to make the NORM data set is randomized, and the underlying probability model for a random sampling event predicts that the random seed may not pull exactly ‘F’ QSM reads out of the whole data set when making the NORM data set. Alternatively, the QSM and non-QSM data may be separated and binned and normalized with ALPHA, which yields exactly ‘F’ QSM reads (e.g., 5000) in the QSM bin and the appropriate number of reads in the non-QSM bin. Specifically, pseudorandom stratified subsampling may be used to retain the appropriate number of reads originating from QSM in each sample’s data set. This normalization ensures that sequencing depth and LOD are uniform across samples, and reduces the computational burden of subsequent analysis steps. To perform QSM alignment and normalization, QSM reads are separated from non-QSM reads by alignment according to well-established procedures known in the art. This separates read pairs into a set that originates from QSM and a set that does not originate from QSM. The count of QSM read pairs is used to calculate a subsampling fraction for each sample, with the subsampling fraction being given by Equation 5. The subsampling fraction and the count of non-QSM read pairs are used to calculate the number of non-QSM read pairs to subsample for each sample. Pseudorandom read subsampling randomly selects the specified number of non-QSM read pairs according to a seed. The seed ensures that while the subsampling is random, it is also reproducible.

In one embodiment, the known quantity of the internal quantification standard added to the sample can be used to calculate the input quantity (IQT) of the unknown nucleic acid(s) in the sample after normalization by Equation 6.

IQT=Normalized No. of unknown nucleic acid sequencing reads attributed to the unknown nucleic acid*(Input Quantity of internal quantification standard/*F*) [Equation 6]

For instance, referring back to sample B of FIG. 9, Equation 6 can be used to calculate the IQT of unknown nucleic acid X as follows: There were 500 reads attributed to X after normalization and ‘F’ was set at 5000, thus IQT=500*(10/5000)=1. Many samples will have more than one unknown nucleic acid. Thus, the input quantity (IQTi, IQTj, IQTk IQTn) of multiple unknown nucleic acids in the sample may be calculated after normalization by Equation 7.

IQTn=Normalized No. of unknown “*n*” nucleic acid sequencing reads attributed to the “*n*th” unknown nucleic acid*(Input Quantity of internal quantification standard/*F*) [Equation 7]

After counting the normalized number of reads attributed to each of the different unknown nucleic acids (e.g., by alignment, pseudo-alignment, or assembly methods), these normalized numbers of reads can be used to determine the input concentration of each of the unknown nucleic acids.

The same principal also applies to pooled samples. Each pooled sample has its own QSM and its own unique set of sample-specific identification sequences such that the sequencing data from each sample in the pool can be distinguished and separated. Thus, the normalization can be separately applied to the sequencing data originating from each sample in the pool. Thus, each sample in a pool of samples has its own (1) data acceptance/rejection criteria and (2) substantially the same limit of detection (LOD) is applied to all unknown nucleic acids in each sample. This is important because, as was illustrated in FIGS. 10 and 11, some samples may be very concentrated and some may have only nucleic acids at or near the LOD and some samples may be over or under read for QSM, while some samples may be read for QSM at or near the acceptance criteria. For instance, as was illustrated with respect to samples 6, 9, 10, and 14, QSM for some samples may be over represented in the pooled data set, while others like 15, 17, 26, and 32 have QSM values at or near the acceptance criteria. Separately assessing QSM and applying the normalization to each sample is powerful because (1) it ensures that each sample has sufficient read depth (some individual samples can be rejected without having to reject the whole data set), (2) it ensures that very concentrated samples do not swamp out the low concentration samples, (3) it ensures that the same LOD is being applied to all samples, and (4) it ensures that an objectively fair amount of data are being assessed from each sample for normalization and quantification. Thus, Equation 7 can be used for calculating the input quantity of multiple nucleic acids in multiple samples in a pool.

Figure 13:
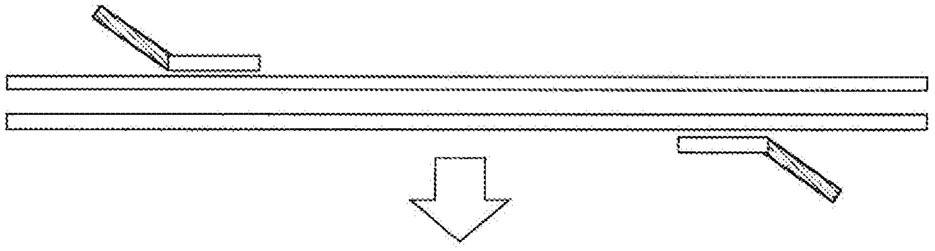
FIG. 13 illustrates an example of a sequencing sample preparation workflow.
Figure 13:
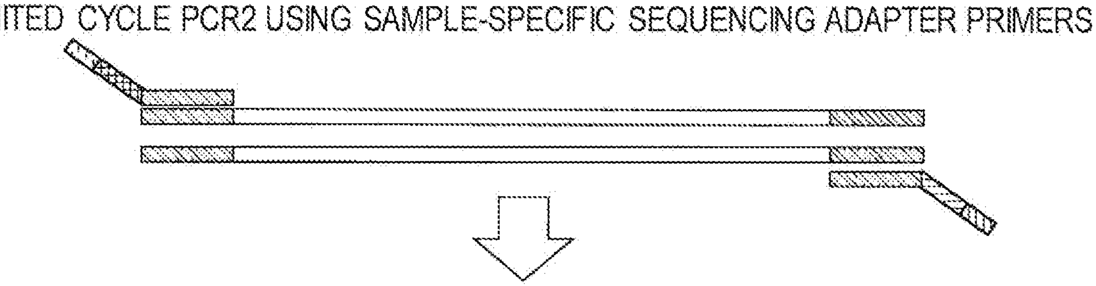

In some embodiments, preparing samples for sequencing may include specific procedures. In one embodiment, preparing a sample for sequencing may include sample lysis, recovery of nucleic acids from the lysate and optionally purifying the recovered nucleic acids, and introducing sequencing adapter sites and sample-specific identification sequences into regions of the nucleic acids to be sequenced. In one embodiment, the sequencing adapter sites may include regions for attaching the nucleic acids to the platform (e.g., a flow cell) for sequencing and sequencing primer binding sites. An example of a sample preparation workflow is illustrated in FIG. 13. In some embodiments, the internal quantification standard/QSM may be added before or after lysis, for example, depending on the likelihood that the QSM may be damaged or fragmented by the lysis protocol. For example, if sample lysis involves bead beating or sonication, the QSM may be added after lysis but before recovery and purification of the nucleic acids. If chemical lysis or gentle mechanical lysis is employed, then the QSM may be added prior to lysis.

In an illustrative example, it is believed that the internal quantification standard can be used to estimate true input concentration of the unknown nucleic acids in the original sample by factoring in the loss during sample preparation and sequencing. I.e., the internal quantification standard is carried through all steps of the analysis. Thus, any loss is systematic and the sequenced concentration may be used for back-calculating true input concentrations by making the loss due to sample extraction, sequencing, etc. the same for each sample throughout the process.

In one embodiment, introducing sequencing adapter sites and sample-specific identification sequences may include one of: (1) amplifying the nucleic acids to be sequenced in a amplification reaction using target-specific primers that include sequencing primer binding sites and sample-specific identification sequences, or (2) fragmenting the nucleic acids to be sequenced and ligating to the fragmented nucleic acids sequencing-specific adapters that include sequencing primer binding sites and sample-specific identification sequences.

Figure 14:
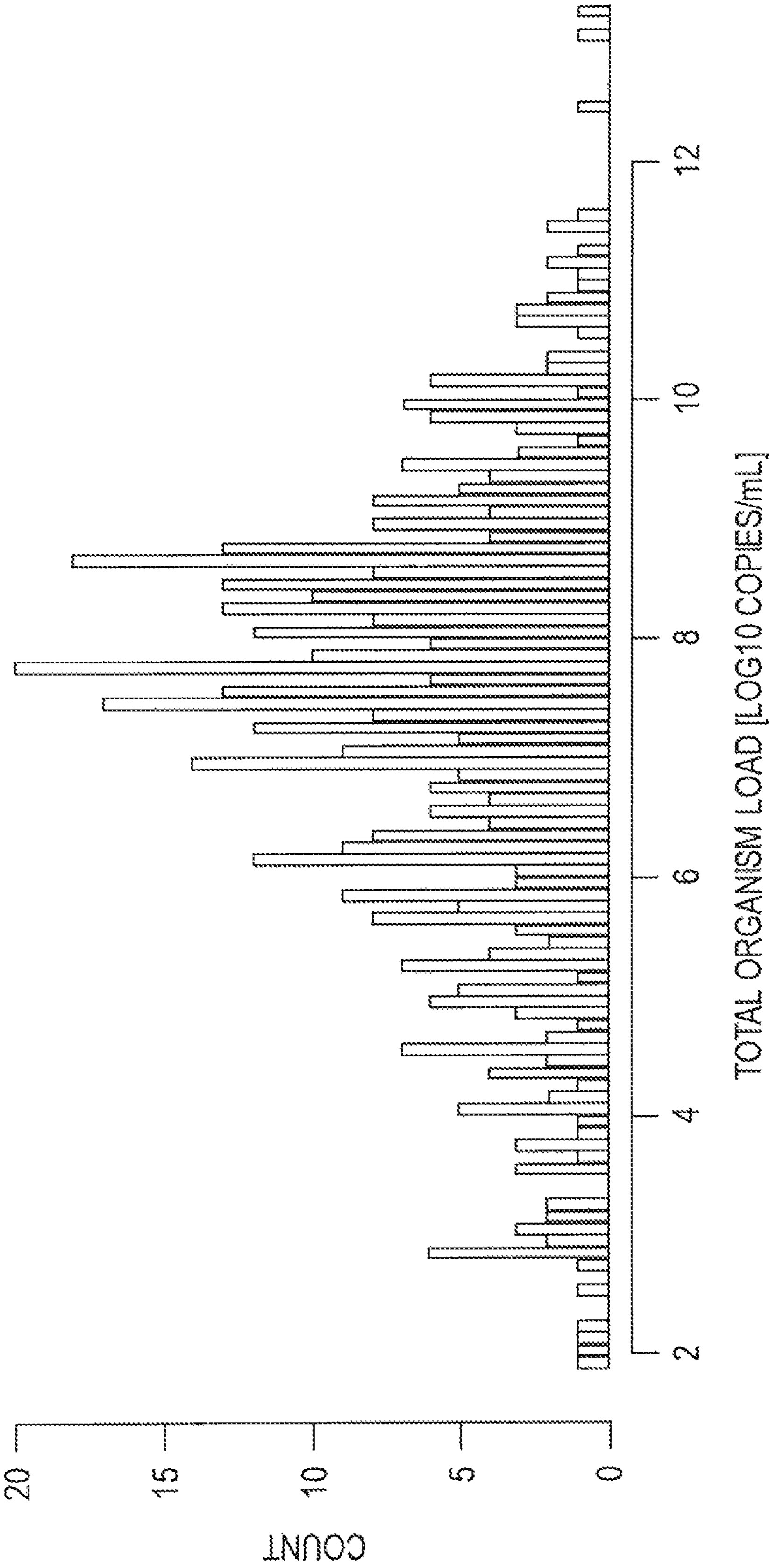
FIG. 14 shows the bacterial and/or viral load distribution in a population of sputum samples.
Figure 15:
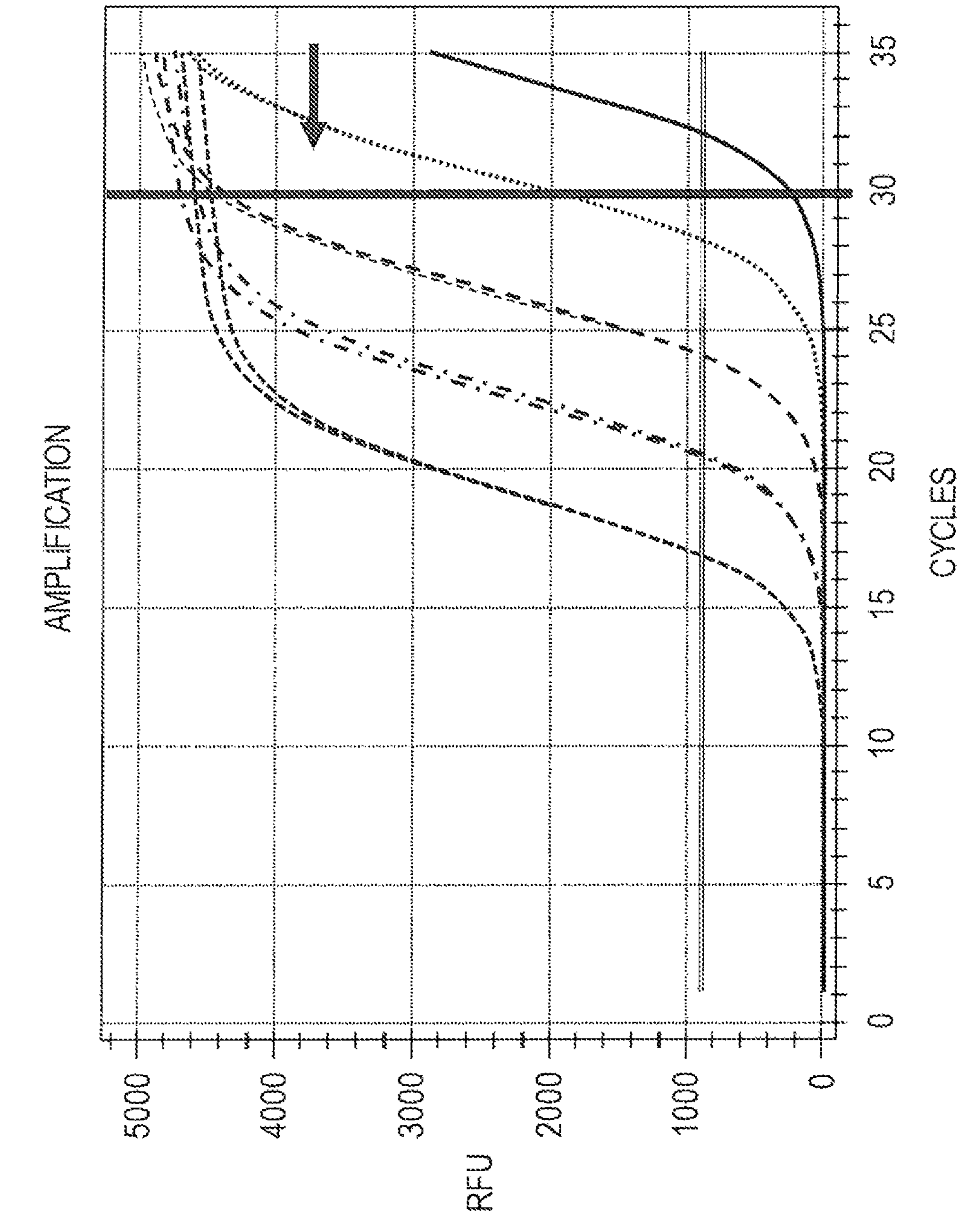
FIG. 15 shows PCR amplification curves illustrating a method for preserving the dynamic range of a sequencing reaction wherein the reaction is set up and stopped such that high-copy targets are in the plateau phase and lower-copy targets are in the exponential amplification phase.

In one embodiment, amplifying the nucleic acids to be sequenced may include: performing a first multiplex PCR reaction using target-specific primers having custom overhangs, performing a first nucleic acid purification, performing a second PCR reaction using sequencing adapter primers that anneal or ligate to the custom overhangs introduced in the first PCR, and performing a second nucleic acid purification. In one embodiment, the sequencing adapter primers are target-independent and include sequencing primer adapter sites and sample-specific identification sequences As illustrated in FIG. 14, the total organism load in typical samples can vary widely—between about 0 and $10^{13}$ organisms/ml (typically about $10^2$-$10^7$). This can lead to a very broad range of nucleic acid copies/ml input into the sequencing reaction. In one embodiment, the amplification reaction can be used to suppress the upper range of the reaction so that the samples submitted for sequencing effectively have nucleic acid numbers in a more narrow relative dynamic range, as an example about $10^2$-$10^7$. In one embodiment, the methods described herein may include limiting one or more of concentration of the target-specific primers or cycle number in the first multiplex PCR reaction to plateau amplification of nucleic acids present at concentration greater than about $10^7$ copies/ml and to preserve nucleic acids less than about $10^7$ copies/ml in the exponential amplification phase. This is illustrated in FIG. 15. For instance, the upper LOD of the sequencing assay may be linear in a range of about $10^2$-$10^7$ copies of each nucleic acid. Above about $10^7$ nucleic acid copies/ml it is desirable to avoid having to oversequence such concentrated nucleic acids outside the linear range of the assay and such nucleic acids may be reported as having an input concentration reported as $>10^7$ nucleic acid copies/ml, while all of the nucleic acids from about $10^2$-$10^7$ are preserved in the linear range of the assay and reported at their true input quantity by a corresponding number of normalized sequencing reads. In some embodiments, it may be desirable to suppress the lower end of the dynamic concentration range by restricting the number of amplification cycles. In one embodiment, the LOD of the assay may dictate a lower reporting range and nucleic acids below the LOD may be reported as 'not detected.'

In one embodiment, the input quantities of the nucleic acids in the samples may instead be reported semi-quantitatively or in 'binned' ranges. In many embodiments, absolute quantification is not necessary, and semi-quantitative results may be sufficient. Moreover, reporting binned ranges may be simpler and may allow the reporting to account for target-specific errors in the data. Results may be reported as absolute concentrations (with or without system error (illustratively 95% prediction interval)), or may be binned into one of a plurality of ranges, illustratively reporting a "high," "medium," or "low" concentration, each covering one or more orders of magnitude.

Likewise, the input quantities of the nucleic acids in the samples may be reported in numerical bins. An example is shown below in Table 2.

TABLE 2

| Bin | Semi-quantitative reporting level |
|---|---|
| 10^3 | <10^3.5 |
| 10^4 | 10^3.5-≤10^4.5 |
| 10^5 | 10^4.5-≤10^5.5 |
| 10^6 | 10^5.5-≤10^6.5 |
| >10^7 | ≥10^6.5 |

Each bin encompasses values that span one log; bins are defined as a range with 0.5 log on either side of the bin label (i.e. the 10^5 bin contains quantities from 10^4.5 to 10^5.5, etc.). The extra 0.5 log on either side of the bin range is to account for the measurement variability seen near bin boundaries. The exceptions illustrated in Table 2 are the lowest bin in which any value below 10^3.5 may be reported as "Not Detected" and the highest bin where any value equal to or greater than 10^6.5 may be reported as >10^7. It is understood, however, that these lower and upper reporting values are illustrative only and that different lower and upper reporting value ranges may be used depending on factors such as, but not limited to, the LOD and the dynamic range of a given assay. Two standard deviations, or 0.5 log from the bin boundary, is the theoretical range to capture 95% of data points not centered on the bin boundary. It is understood that the number of bins may vary, as is appropriate with a specific assay, and any number of bins may be used. Also, the range of binning (orders of magnitude or other measures) for semi-quantitative results may be adjusted, as is appropriate for the specific example.

Example 5: A Method for Performing a Comparator Study

When a diagnostics test provider (e.g., BioFire Diagnostics) develops a new commercial diagnostic test, the test provider is often required by the FDA to perform comparator studies to provide confirmation that the new commercial test delivers the results that the provider claims it does. Typically, the comparator assay uses independent and well-accepted gold standard technologies such as standard of care (SOC) culture methods to check the results of the new assay. However, current SOC culture methods may not provide highly accurate or consistent detection and quantification of bacterial targets in clinical samples. This is due to many factors, including the often heightened sensitivity of molecular assays over culture, the fact that culture can only detect living organisms, and the challenge of working up unique colony morphologies from complex, organism-rich specimen types.

For molecular assays like the FilmArray system described herein that detect the presence of organisms in a sample using PCR and fluorescent detection, Sanger sequencing is an accepted alternative comparator to SOC culture methods. However, as molecular assays become more complex, the sequencing burden with traditional Sanger sequencing becomes greater. Likewise, where quantification is claimed by the commercial test, the comparator sequencing assay may also need to provide quantitative or semi-quantitative results.

Described herein is a high-throughput alternative to conventional PCR and bi-directional sequencing comparator methods that have previously been used in the field. Preferably, the sequencing method employed in the comparator study is Next-Generation Sequencing (NGS) or a similar massively parallel sequencing technology. For targets (e.g., bacteria, viruses, fungi, etc.) on diagnostic panels requiring semi-quantitative organism load reporting, or the antibiotic resistance markers associated with some bacteria, a quantitative or semi-quantitative molecular reference method for use as a comparator during clinical trials was developed as a preferred embodiment. The novel molecular reference method described herein leverages the inherently digital and massively parallel nature of NGS. While Illumina NGS was used in the specific embodiments discussed herein, the principles described herein can be adapted to other sequencing platforms with minimal modification.

In one embodiment, methods for performing a comparator study are described. The method for performing a comparator study may include providing a first assay comprising multiplex amplification and detection of one or more target nucleic acids, the first assay having a limit of detection (LOD) and providing a second assay different than the first assay for confirming the detections and LOD of the first assay. The second assay may include: preparing the sample including at least one internal quantification standard for sequencing, sequencing to generate a sequencing data set for the sample, wherein the sequencing data set includes sequencing reads observed from the target nucleic acid(s) and from the internal quantification standard, counting the number of sequencing reads in the sequencing data set originating from the target nucleic acid(s) and the internal quantification standard, and normalizing the sequencing data set, wherein the normalization (1) applies data acceptance/rejection criteria to the sequencing data set based on the presence of a minimum number of sequencing reads for the internal quantification standard for the sample and (2) ensures that substantially the same limit of detection (LOD) is applied to all unknown nucleic acids in the sequencing assay. The LOD of the second assay is preferably substantially the same as an LOD of the first assay.

The results of the second assay may be compared to the results of the first assay. Preferably, the organisms and quantities of the organisms detected in the first assay should agree with the detections and quantities reported by the second assay.

In one embodiment, the first assay may include adding one or more internal quantification standards to the sample, and performing quantitative two-step amplification on the sample. In one embodiment, the quantitative two-step amplification in the first assay includes: amplifying the sample in a first-stage multiplex amplification mixture, the amplification mixture comprising a plurality of target primers, each target primer configured to amplify a different target that may be present in the sample, and at least one quantification standard primer, the quantification standard primer configured to amplify internal quantification standard nucleic acids, dividing the first-stage amplification mixture into a plurality of second-stage individual reactions, a first group of the plurality of second-stage individual reactions each comprising at least one primer configured to further amplify one of the different targets that may be present in the sample, and a second group of the plurality of second-stage individual reactions each comprising at least one primer configured to further amplify one of the internal quantification standard nucleic acids, and subjecting the plurality of second-stage individual reactions to amplification conditions to generate one or more target amplicons and a plurality of quantification standard amplicons, each quantification standard amplicon having an associated quantification standard Cp. Each target nucleic acid has a crossing point (Cp) and each internal standard has a known concentration in the first assay and a known quantification standard Cp.

In one embodiment, it may be possible to determine the input concentration of the unknown nucleic acids in the first assay by comparison to the known input concentration of the quantification standards. In one embodiment, the method may further include generating a standard curve from the quantification standard Cps, and quantifying each of the one or more target nucleic acids using the standard curve. In one embodiment, each of the target nucleic acids is quantified using a standard curve generated using a least squares regression line fit to Equation 3.

$$\mathrm{Log}_{10}(\mathrm{Concentration})=(Cp-b)/a \qquad \text{[Equation 3]}$$

In Equation 3, Cp is the crossing point measured for each target, b, the intercept, represents the Cp value when the log 10(concentration) of the target is zero, and a is the slope which represents the degree to which Cp changes with a single unit change in concentration.

Referring again to the second assay, the data from the second assay may be normalized and the input quantity of the unknown nucleic acids may be determined as described above in Example 4. Importantly, a read depth threshold checkpoint based on a predetermined expected number of QSM reads precedes target-specific analysis. Samples with insufficient read depth are flagged for additional sequencing, while samples with sufficient read depth are normalized. This ensures that the quantitative value of a read is the same across every sample, and that target detection is independent from total target load.

The predetermined expected number of QSM reads, i.e., 'F', can be selected for different limits of detection to match the first assay. For instance, if QSM is spiked into samples at $5\times10^5$ copies/ml and 'F' is $5\times10^3$ then the LOD for detection of the target nucleic acid(s) in the second assay will be in the range of about $10^2$-$10^3$ copies/ml. Similarly, if is $5\times10^4$ then the LOD for detection of the target nucleic acid(s) in the second assay will be in the range of about $10^1$-$10^2$ copies/ml. In general, the greater the magnitude of 'F', the lower the LOD is for the sequencing assay. This follows because, as was explained in detail in Example 4, the greater the magnitude of 'F', the greater the sequencing depth of the assay. The relationship between QSM spike level (e.g., $5\times10^5$ copies/nil), 'F' (e.g., 'F'=5000), read count, and semi-quantitative, binned target reporting for representative post-normalization read counts at each reporting level is illustrated in Table 3.

TABLE 3

| Semi-quantitative reporting level | Read count |
|---|---|
| <10^3.5 | <32 |
| 10^3.5-10^4.5 | 32-≤420 |
| 10^4.5-10^5.5 | 420-≤5200 |
| 10^5.5-10^6.5 | 5200-≤62,000 |
| >10^6.5 | ≥62,000 |

Likewise, as was described above, multiple samples may be pooled for the sequencing assay. Pooling, while not required, is where massively parallel DNA sequencing shows its real power. For instance, the ability to pool and sequence in parallel significantly reduces the time and personnel needed to perform the comparator study. Samples may be pooled, normalized, and quantified as was described above in Example 4.

Example 6: Assay Specific Correction Factors

Ideally, Next-Generation Sequencing (NGS) should report exactly the same target quantification as any other quantitative molecular method, such as digital PCR. However, the reality is that variability in sampling and measurement may still be present in the respective reference methods, and such randomness often precludes achievement of this perfect agreement scenario. One possible solution is to report the data with appropriate error ranges, or to bin the data. However, if the errors are assay specific and not uniform/systematic across all sample types, then error ranges or binning may not account for all of the errors in the data On the other hand, it is possible to use assay specific correction factors to further account for repeatable and systematic factors like differences in nucleic acid amplification efficiency, differences in nucleic acid purification efficiency, differences in sequencing library preparation, and differences in sequencing efficiency. Since such differences are repeatable and systematic for a given sample, analyte, and/or assay, the differences can be measured and used to generate assay-specific correction factors to correct target quantification. The NGS methods described herein may use assay-specific correction factors to remove systematic differences in target quantification performance for a number of targets observed across many (e.g., over fifty) experimental measurements.

The assay-specific correction factors described in this example were derived by analyzing assay-specific positive control (PC) sequences in over fifty batch positive controls. The PC sequences may be added to test samples, or they may be included in each run as a separate sample. Prior to amplification, batch positive controls may be spiked with a mixture of PC sequences (e.g., engineered gBlocks) at a known concentration (e.g., 50 copies of each PC gBlock per reaction), as well as Quantification Standard Material (e.g., 500 copies of QSM per reaction). If the efficiency of PCR amplification is not perfect or if the efficiency of the target and internal standard is different, the correction factor can depend on the quantity of positive control input into the reaction. Thus, in one embodiment, the quantity of positive controls should be in the middle of the targeted dynamic range of the corresponding targets. In one embodiment, PC sequences may be designed to be amplified with the same target-specific primers with overhangs that are used in the test assays, such that sample-specific sequencing adapter primers can anneal to amplified PC sequences in the same manner as with the test assays. Naturally, the positive controls are designed to have their own unique, identifying sequence region between the conserved primer binding site regions. In this way, sequencing data derived from the positive controls can be identified and separately analyzed. The PC sequences may contain assay-specific targets, and are expected to be quantified at an equivalent level when each assay has the same performance (e.g., $10^{4.7}$ copies/mL).

Figure 16:
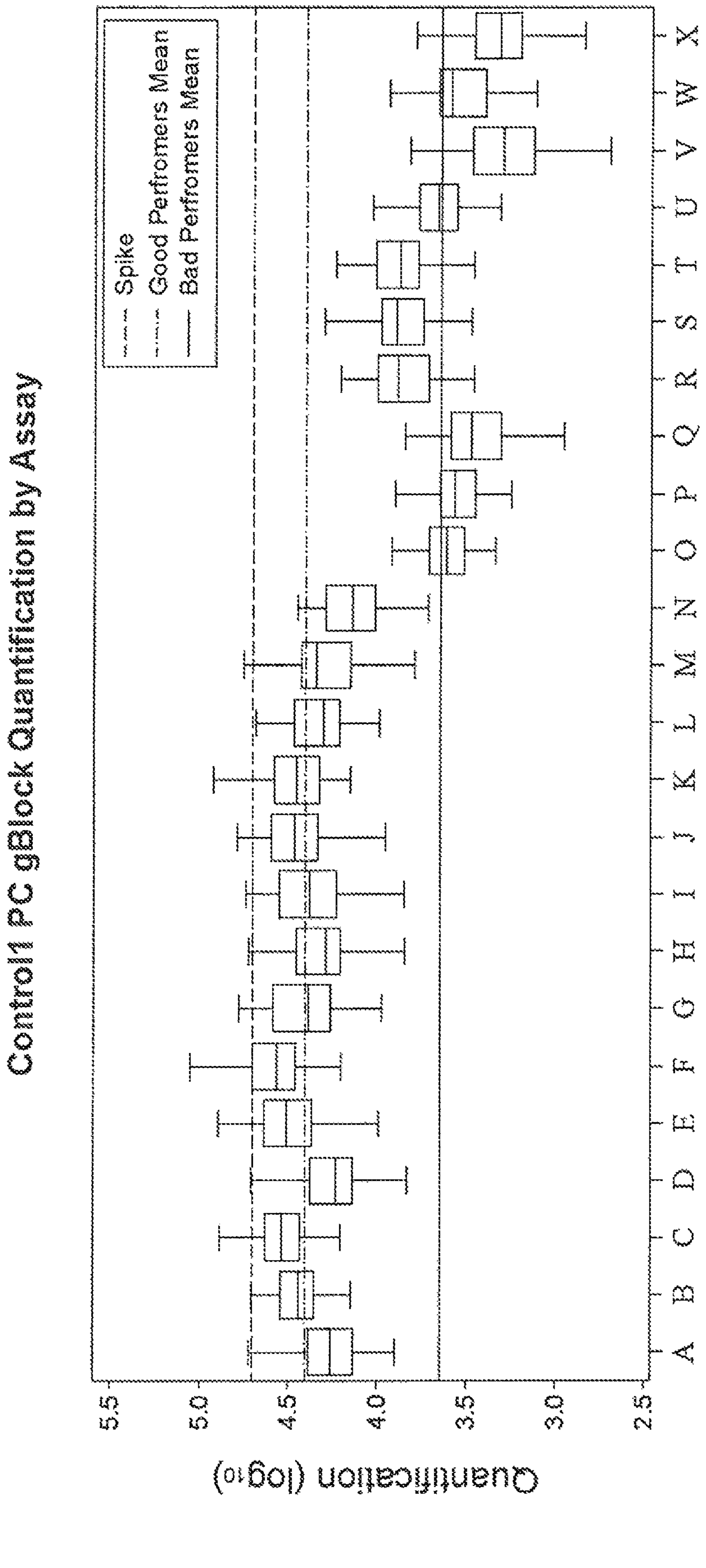
FIG. 16 shows Batch Positive Control (PC) Quantification by assay.

FIG. 16 shows, however, that two populations of assays were observed. For the purposes of this Example, the two populations of assays are referred to as good performers and bad performers. Assays referred to as good performers are seen on the left of the graph (A-M), and assays referred to as bad performers are seen on the right of the graph (O-X). Sample N is an intermediate performer. The average log 10 quantification of the good performers is consistently close to the expected quantification, while the average log 10 quantification of the bad performers is not. That is, the 'good performers' can be assumed to consistently quantify in the test assays at close to their expected performance, while the 'bad performers' can be assumed to consistently quantify in the test assays at values significantly worse than their expected performance. More specifically, the good performers are defined as assays with an average log 10 quantification within 0.5 log 10 of the expected quantification, while the bad performers are defined as assays with an average log 10 quantification that is ≥0.5 log 10 lower than the expected quantification. The average log 10 quantification of the good performers is 0.23 log 10 lower than the expected quantification, while the average log 10 quantification of the bad performers is 1.0 log 10 lower than the expected quantification. One assay with intermediate performance was observed (shown at N).

The assay-specific correction factors described in this Example were defined to be the difference between each assay's average log 10 quantification and the average log 10 quantification of the good performers ($10^{4.47}$ copies/mL), allowing for up to a 1.0 log 10 correction factor. In this Example, assay-specific correction factors were derived for the specific set of assays. Persons of ordinary skill will appreciate, however, that the principles described in this Example can be adapted and applied to other assays with only minimal, assay-specific modification.

Example 7: A Kit for Normalizing and Quantifying an Unknown Nucleic Acid in a Next-Generation Sequencing (Ngs) Assay In one embodiment, a kit for normalizing and quantifying an unknown nucleic acid in a Next-Generation Sequencing (NGS) assay is disclosed. The kit may include an internal quantification standard, wherein the internal quantification standard is a nucleic acid configured to be added in a known amount to a sample including an unknown nucleic acid to be sequenced, and instructions for using the internal quantification standard for normalizing and quantifying a sequencing data set and for calculating an input quantity of the unknown nucleic acid(s). In one embodiment, the kit may include a set of internal quantification standards to be added at different known concentrations for generating a standard curve for quantification of unknown nucleic acids. In one embodiment, the internal quantification standard may be configured to be added to the sample in the range of about $10^4$-$10^6$ copies/ml. In one embodiment, using the internal quantification standard, sequencing data may be normalized by Equation 5

NORM=No. of Sequencing Reads*(*F*/Observed No. of Sequencing Reads Originating from the Internal Quantification Standard) [Equation 5]

Where 'F' is a fixed minimum expected number of the internal quantification standard sequencing reads. In one embodiment, using the internal quantification standard, an input quantity (IQT) of the unknown nucleic acid may be calculated by Equation 6:

IQT=Normalized No. of unknown nucleic acid sequencing reads attributed to the unknown nucleic acid*(Input Quantity of internal quantification standard/*F*) [Equation 6]

In one embodiment, the kit may further include sequencing-specific adapters for at least the internal quantification standard that include sequencing primer binding sites and sample-specific identification sequences. In one embodiment, the kit may further include target-specific primers having custom overhangs configured for amplification of the internal quantification standard and for annealing or ligation to the sequencing-specific adapters.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. While certain embodiments and details have been included herein and in the attached invention disclosure for purposes of illustrating the invention, it will be apparent to those skilled in the art that various changes in the methods and apparatus disclosed herein may be made without departing from the scope of the invention, which is defined in the appended claims. All changes which come within the meaning and range of equivalency of the claims are to be embraced within their scope.

What is claimed is:

1. A method for read value normalization of a sequencing assay, comprising:

providing a sample including one or more unknown nucleic acid(s) to be sequenced, wherein each unknown nucleic acid in the sample has a concentration of about $10^2$-$10^7$ copies/ml;

adding to the sample a known quantity of an internal quantification standard in a range of $10^3$-$10^6$ copies/ml;

setting a minimum number of sequencing reads for the internal quantification standard, wherein the minimum number of sequencing reads set for the internal quantification standard is in a range of $10^2$-$10^5$;

preparing the sample including the internal quantification standard for sequencing, wherein the preparing includes introducing sequencing-specific adapter sites and sample-specific identification sequences into the one or more unknown nucleic acid(s) and the internal quantification standard in the sample;

sequencing the sample with a Next-Generation Sequencing (NGS) instrument to generate a sequencing data set for the sample, wherein the sequencing data set includes unknown nucleic acid reads, which are sequencing reads observed from the one or more unknown nucleic acid(s), and internal quantification standard reads, which are sequencing reads observed from the internal quantification standard;

counting the number of sequencing reads in the sequencing data set originating from the one or more unknown nucleic acid(s) and from the internal quantification standard;

determining whether the minimum number of sequencing reads for the internal quantification standard has been reached in the sequencing data set;

responsive to determining that the minimum number of sequencing reads for the internal quantification standard has been reached in the sequencing data set, determining that sufficient sequencing read depth of the sample has been reached in the sequencing data set to detect at least one of the one or more unknown nucleic acid(s) present in the sample at or above a limit of detection (LOD), wherein sufficient sequencing read depth of the sample is reached upon detecting the minimum number of sequencing reads for the internal quantification standard in the sequencing data set;

responsive to determining that sufficient sequencing read depth of the sample has been reached in the sequencing data set, normalizing the sequencing data set using the number of sequencing reads counted for the internal quantification standard to provide a normalized sequencing data set; and quantifying the at least one of the one or more unknown nucleic acid(s) present in the sample at a concentration greater than the LOD based on the normalized sequencing data set.

2. The method of claim 1, wherein the known quantity of the internal quantification standard added to the sample is in the range of about $10^4$-$10^6$ copies/ml and the minimum number of sequencing reads set for the internal quantification standard is in a range of $10^3$-$10^5$.

3. The method of claim 1, wherein normalizing the sequencing data set retains NORM sequencing reads, where NORM=No. of Sequencing Reads*(F/Observed No. of Sequencing Reads Originating from the Internal Quantification Standard), and wherein 'F' is the fixed minimum expected number of the internal quantification standard sequencing reads.

4. The method of claim 3, wherein the unknown nucleic acid reads and the internal quantification standard reads are each separately normalized by the same ratio ALPHA, where ALPHA=F/Observed No. of Sequencing Reads Originating from the Internal Quantification Standard.

5. The method of claim 1, further comprising calculating an input quantity (IQT) of the at least one of the one or more unknown nucleic acid in the sample after normalization, wherein because the input quantity of the internal quantification standard is known, the input quantity (IQT) of the at least one of the one or more unknown nucleic acid can be calculated by IQT=Normalized No. of unknown nucleic acid sequencing reads attributed to the unknown nucleic acid* (Input Quantity of internal quantification standard/F).

6. The method of claim 1, wherein preparing the sample includes sample lysis, recovery of nucleic acids from the lysate and optionally purifying the recovered nucleic acids, and introducing primer binding sites and sample-specific identification sequences into regions of the nucleic acids to be sequenced.

7. The method of claim 6, wherein preparing the sample includes one of:

amplifying the nucleic acids to be sequenced in an amplification reaction using target-specific primers having dual-indexed sequencing overhangs that include sequencing primer binding sites and sample-specific identification sequences, or fragmenting the nucleic acids to be sequenced and ligating to the fragmented nucleic acids sequencing-specific adapters that include sequencing primer binding sites and sample-specific identification sequences.

8. The method of claim 7, wherein amplifying the nucleic acids to be sequenced includes:

performing a first multiplex PCR reaction using target-specific primers having custom overhangs, performing a first nucleic acid purification, performing a second PCR reaction using dual-indexed sequencing adapter primers that anneal or ligate to the overhangs introduced in the first PCR, wherein the dual-indexed sequencing adapter primers are target-independent and include sequencing primer binding sites and sample-specific identification sequences, performing a second nucleic acid purification.

9. The method of claim 1, further comprising pooling two or more samples and subjecting them to sequencing simultaneously, wherein the two or more samples are pooled after the preparing and before the sequencing.

10. The method of claim 1, wherein the sequencing assay is a next-generation sequencing assay.

11. The method of claim 1, wherein the sequencing assay does not include performing a relative quantification, performing a quantification in a reaction separate from the sequencing assay, using an assay-or template-specific quantification standard, or using a competitive template as a quantification standard.

12. The method of claim 1, wherein quantifying the at least one of the one or more unknown nucleic acid(s) present in the sample at a concentration greater than the LOD based on the normalized sequencing data set comprises quantifying the concentration using the known quantity of the internal quantification standard added to the sample, the set minimum number of sequencing reads required for the internal quantification standard, the number of sequencing reads counted for the internal quantification standard, and the counted number of sequencing reads for the at least one of the one or more unknown nucleic acid(s).

13. The method of claim 12, wherein the normalized sequencing data are scaled by a ratio of the minimum number of sequencing reads for the internal quantification standard over the number of sequencing reads counted for the internal quantification standard.

14. The method of claim 1, wherein the LOD for the quantitative sequencing assay is calculated using the known quantity of the internal quantification standard added to the sample and the set minimum number of sequencing reads required for the internal quantification standard, wherein the known quantity of the internal quantification standard added to the sample is in the range of about $10^4$-$10^6$ copies/ml and the set minimum number of sequencing reads for the internal quantification standard is in the range of about $10^2$-$10^4$ sequencing reads.

15. The method of claim 1, wherein the normalized sequencing data set is calculated using the minimum number of sequencing reads for the internal quantification standard for the sample and applying substantially the same limit of detection (LOD) to all unknown nucleic acids in the sequencing assay, wherein the LOD can be raised or lowered by increasing or decreasing the minimum number of sequencing reads for the internal quantification standard.

16. A method for read value normalization of a sequencing assay, comprising:

providing a sample including one or more unknown nucleic acid(s) to be sequenced, wherein each unknown nucleic acid in the sample has a concentration of about 102-107 copies/ml;

adding to the sample a known quantity of an internal quantification standard;

setting a minimum number of sequencing reads for the internal quantification standard, wherein the minimum number of sequencing reads set for the internal quantification standard is greater than 1;

preparing the sample including the internal quantification standard for sequencing, wherein the preparing includes introducing sequencing-specific adapter sites and sample-specific identification sequences into the one or more unknown nucleic acid(s) and the internal quantification standard in the sample;

sequencing the sample with a Next-Generation Sequencing (NGS) instrument to generate a sequencing data set for the sample, wherein the sequencing data set includes unknown nucleic acid reads, which are sequencing reads observed from the one or more unknown nucleic acid(s), and internal quantification standard reads, which are sequencing reads observed from the internal quantification standard;

counting the number of sequencing reads in the sequencing data set originating from the one or more unknown nucleic acid(s) and from the internal quantification standard;

determining whether the minimum number of sequencing reads for the internal quantification standard has been reached in the sequencing data set;

responsive to determining that the minimum number of sequencing reads for the internal quantification standard has been reached in the sequencing data set, determining that sufficient sequencing read depth of the sample has been reached in the sequencing data set to detect at least one of the one or more unknown nucleic acid(s) present in the sample at or above a limit of detection (LOD), wherein sufficient sequencing read depth of the sample is reached upon detecting the minimum number of sequencing reads for the internal quantification standard in the sequencing data set;

responsive to determining that sufficient sequencing read depth of the sample has been reached in the sequencing data set, normalizing the sequencing data set to provide a normalized sequencing data set; and quantifying the at least one of the one or more unknown nucleic acid(s) present in the sample at a concentration greater than the LOD based on the normalized sequencing data set;

wherein normalizing the sequencing data set retains NORM sequencing reads, where NORM=No. of Sequencing Reads*(F/Observed No. of Sequencing Reads Originating from the Internal Quantification Standard), and wherein 'F' is a fixed minimum expected number of the internal quantification standard sequencing reads.

17. The method of claim 16, wherein the known quantity of the internal quantification standard added to the sample is in the range of about 103-106 copies/ml and the minimum number of sequencing reads set for the internal quantification standard is in a range of $10^2$-$10^5$.

18. The method of claim 17, wherein the known quantity of the internal quantification standard added to the sample is in the range of about 104-106 copies/ml and the minimum number of sequencing reads set for the internal quantification standard is in a range of $10^3$-$10^5$.

19. The method of claim 16, wherein the unknown nucleic acid reads and the internal quantification standard reads are each separately normalized by the same ratio ALPHA, where ALPHA=F/Observed No. of Sequencing Reads Originating from the Internal Quantification Standard.

20. The method of claim 16, further comprising calculating an input quantity (IQT) of the at least one of the one or more unknown nucleic acid in the sample after normalization, wherein because the input quantity of the internal quantification standard is known, the input quantity (IQT) of the at least one of the one or more unknown nucleic acid can be calculated by IQT=Normalized No. of unknown nucleic acid sequencing reads attributed to the unknown nucleic acid*(Input Quantity of internal quantification standard/F).

21. The method of claim 16, further comprising submitting the sample for additional sequencing with the NGS instrument if the minimum number of sequencing reads for the internal quantification standard has not been recorded.

22. A method for determining clinical relevance of an unknown nucleic acid detected in a sequencing assay, comprising:

providing a sample including one or more unknown nucleic acid(s) to be sequenced, wherein each unknown nucleic acid, if present in the sample, has a concentration of about $10^2$-$10^7$ copies/ml;

adding to the sample a known quantity of an internal quantification standard in a range of $10^3$-$10^6$ copies/ml;

setting a minimum number of sequencing reads for the internal quantification standard, wherein the minimum number of sequencing reads set for the internal quantification standard is in a range of $10^2$-$10^5$;

preparing the sample including the internal quantification standard for sequencing, wherein the preparing includes introducing sequencing-specific adapter sites and sample-specific identification sequences into the one or more unknown nucleic acid(s) and the internal quantification standard in the sample;

sequencing the sample with a Next-Generation Sequencing (NGS) instrument to generate a sequencing data set for the sample, wherein the sequencing data set includes unknown nucleic acid reads, which are sequencing reads observed from the one or more unknown nucleic acid(s), and internal quantification standard reads, which are sequencing reads observed from the internal quantification standard;

counting the number of sequencing reads in the sequencing data set originating from the one or more unknown nucleic acid(s) and from the internal quantification standard;

determining whether the minimum number of sequencing reads for the internal quantification standard has been reached in the sequencing data set;

responsive to determining that the minimum number of sequencing reads for the internal quantification standard has been reached in the sequencing data set, determining that sufficient sequencing read depth of the sample has been reached in the sequencing data set to detect at least one of the one or more unknown nucleic acid(s) present in the sample at or above a limit of detection (LOD), wherein sufficient sequencing read depth of the sample is reached upon detecting the minimum number of sequencing reads for the internal quantification standard in the sequencing data set;

responsive to determining that sufficient sequencing read depth of the sample has been reached in the sequencing data set, normalizing the sequencing data set to provide a normalized sequencing data set; and quantifying the at least one of the one or more unknown nucleic acid(s) present in the sample at a concentration greater than the LOD based on the normalized sequencing data set;

wherein normalizing the sequencing data set retains NORM sequencing reads, where NORM=No. of Sequencing Reads*(F/Observed No. of Sequencing Reads Originating from the Internal Quantification Standard), and wherein 'F' is a fixed minimum expected number of the internal quantification standard sequencing reads.

23. The method of claim 22, wherein the known quantity of the internal quantification standard added to the sample is in the range of about 104-106 copies/ml and the minimum number of sequencing reads set for the internal quantification standard is in a range of $10^3$-$10^5$.

24. The method of claim 22, wherein the unknown nucleic acid reads and the internal quantification standard reads are each separately normalized by the same ratio ALPHA, where ALPHA=F/Observed No. of Sequencing Reads Originating from the Internal Quantification Standard.

25. The method of claim 22, further comprising calculating an input quantity (IQT) of the at least one of the one or more unknown nucleic acid in the sample after normalization, wherein because the input quantity of the internal quantification standard is known, the input quantity (IQT) of the at least one of the one or more unknown nucleic acid can be calculated by IQT=Normalized No. of unknown nucleic acid sequencing reads attributed to the unknown nucleic acid*(Input Quantity of internal quantification standard/F).

26. The method of claim 1, further comprising submitting the sample for additional sequencing with the NGS instrument if the minimum number of sequencing reads for the internal quantification standard has not been recorded.

27. The method of claim 22, further comprising submitting the sample for additional sequencing with the NGS instrument if the minimum number of sequencing reads for the internal quantification standard has not been recorded.

* * * * *